United States Patent [19]
Pellegrino et al.

[11] Patent Number: 5,289,520
[45] Date of Patent: Feb. 22, 1994

[54] STEREOTACTIC MAMMOGRAPHY IMAGING SYSTEM WITH PRONE POSITION EXAMINATION TABLE AND CCD CAMERA

[75] Inventors: Anthony J. Pellegrino, New Fairfield; Milton Stoller, West Hartford, both of Conn.; Kenneth F. DeFreitas, Patterson, N.Y.; David D. Camarra, Fairfield; Anthony M. Scandura, Scotland, both of Conn.; Richard F. Schutz, Brewster, N.Y.; Jeffrey R. Storm, Springfield, Mass.

[73] Assignee: Lorad Corporation, Danbury, Conn.

[21] Appl. No.: 957,275

[22] Filed: Oct. 6, 1992

Related U.S. Application Data

[63] Continuation-in-part of Ser. No. 799,412, Nov. 27, 1991, abandoned.

[51] Int. Cl.⁵ .................................................. A61B 6/04
[52] U.S. Cl. ..................................... 378/37; 378/208; 378/98.2; 128/653.1; 128/662.05
[58] Field of Search ............... 378/37, 181, 62, 64, 378/98, 208, 21, 22, 99; 128/653.1, 662.05

[56] References Cited

U.S. PATENT DOCUMENTS

| | | | |
|---|---|---|---|
| 3,165,630 | 1/1965 | Bielat et al. | 378/37 |
| 3,556,081 | 1/1971 | Jones | 378/37 |
| 3,578,971 | 5/1971 | Lasky | 378/37 |
| 3,609,355 | 9/1971 | Schwarzer | 378/37 |
| 3,963,933 | 6/1976 | Henkes | 378/20 |
| 3,973,126 | 8/1976 | Redington | 378/17 |
| 4,051,380 | 9/1977 | Lasky | 378/37 |
| 4,099,880 | 7/1978 | Kano | 378/41 |
| 4,245,158 | 1/1981 | Burstein | 250/370.09 |
| 4,727,565 | 2/1988 | Ericson | 378/205 |
| 4,852,137 | 7/1989 | MacKay | 378/62 |
| 4,873,708 | 10/1989 | Cusano | 378/19 |
| 4,875,478 | 10/1989 | Chen | 378/20 |
| 4,878,234 | 10/1989 | Pfeiffer | 378/40 |
| 4,890,311 | 12/1989 | Saffer | 378/99 |
| 4,905,265 | 2/1990 | Cox | 378/99 |
| 4,926,452 | 5/1990 | Baker et al. | 378/99 |
| 4,930,143 | 5/1990 | Lundgren | 378/37 |
| 4,987,307 | 1/1991 | Rizzo | 378/191 |
| 5,050,197 | 1/1991 | Virta et al. | 378/37 |
| 5,056,523 | 10/1991 | Hotchkiss | 378/37 |
| 5,067,843 | 4/1992 | Harnio et al. | 128/662.05 |
| 5,078,142 | 1/1992 | Siczak | 378/37 |
| 5,142,557 | 8/1992 | Toker et al. | 378/37 |
| 5,199,054 | 3/1993 | Adams et al. | 378/21 |

OTHER PUBLICATIONS

Bolmgren, et al.; Stereotaxic Instrument for Needle Biopsy of the Mamma; Amer. Journal Roentgenology; 129:121-125, Jul., 1977.
Nordenstrom, Chapter 5, Breast Mammotest-Stereotactic Needle Biopsy System; Advanced Stereotactic Needle Biopsy system-the alternative to surgery; Fischer Imaging Corporation ad.

Primary Examiner—David P. Porta
Assistant Examiner—Kim-Kwok Chu
Attorney, Agent, or Firm—Ware, Fressola, Van Der Sluys & Adolphson

[57] ABSTRACT

An elongated prone patient-supporting examining table for X-ray mammography is centrally supported at variable heights by a rear pedestal. The table is provided with a central breast-receiving aperture through which the patient's pendulant breast is exposed to a horizontal beam of X-rays from a tubehead source mounted on an arm angularly movable through an arc of some 210° centered on the patient's breast. The patient's feet may be positioned at either end of the elongated table on an extensible footrest, permitting X-ray projection through more than 360° around the patient's body. Diagnosis of suspect lesions and fine needle biopsy are both facilitated by stereotactic examination. Digital imaging using a CCD camera and image enhancement software provides magnification, contrast enhancement, window and level manipulation and high resolution images, with low exposure levels, short exposure times, and greatly reduced imaging times.

32 Claims, 18 Drawing Sheets

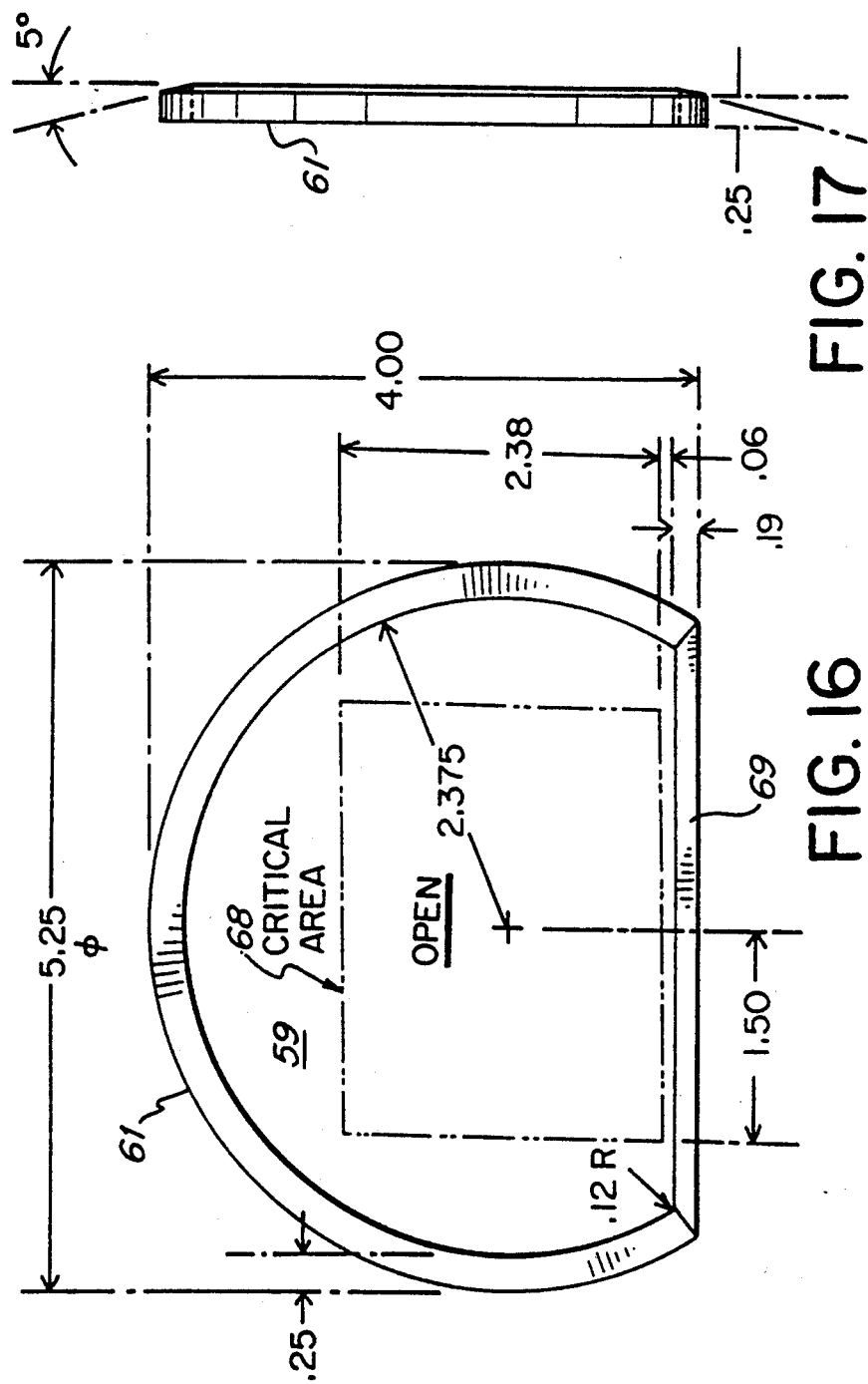

STEREOTACTIC MAMMOGRAPHY IMAGING SYSTEM WITH PRONE POSITION EXAMINATION TABLE AND CCD CAMERA

CROSS REFERENCE TO RELATED APPLICATION

This is a continuation-in-part of the same inventors, co-pending application, Ser. No. 07/799,412, filed Nov. 27, 1992 now abandoned.

This invention relates to a patient-supporting table and associated equipment for X-ray mammography and stereotactic needle biopsy of breast tissue suspected to contain lesions requiring radiographic evaluation.

RELATED ART

Since the publication of an article entitled "Stereotaxic Instrument for Needle Biopsy of the Mamma" by Jan Bolmgren et al, published in the American Journal of Roentgenology Vol. 129, page 121 in July 1977, needle biopsy of breast lesions to minimize unnecessary surgical invasion of the patient's tissue has achieved increasing acceptance. Guidance of the biopsy needle by stereotactic X-ray exposures traditionally required development of the two X-ray film images and their comparison to determine the X, Y and Z coordinates of the lesion in question. Insertion of the biopsy needle via a carefully placed needle guide directed toward the lesion site could be verified only by additional stereo X-ray film exposures.

Mammograms made while the patient sits erect before the X-ray equipment may introduce unavoidable patient movement and resulting inaccuracy, while conventional tables supporting the patient in the prone position with the breast depending through a suitable aperture in the table generally require a patient's arms to be raised, tensing arm muscles, straining or distorting the breast tissue and again introducing inaccuracies. In addition, relatively flat and rigid tables often impose undue stress and discomfort on the patient's joints and vertebra, inducing undesired restless movements.

SUMMARY OF THE INVENTION

The unique prone position mammography tables of the present invention provide comfortable support for the prone patient, with a front edge portion being removable, permitting the patient's arm and shoulder to be lowered to more normal positions and thus minimizing patient discomfort and involuntary movements, leaving the patient normally relaxed during the procedure. In addition, a central concave torso depression formed in these tables exposes the maximum volume of breast tissue for X-ray examination.

Furthermore, the central concave torso depression encircling the breast-receiving aperture is positioned at the center of a longer-than-normal table having an extensible footrest at each end, which is supported by a rear pedestal opposite the removable front edge portion. The X-ray tube and the biopsy needle guide are thus afforded access to the patient's pendulant breast from all possible angles, over a range of more than 360°.

With this invention, accurate placement of the biopsy needle is further achieved via electronic imaging of the tissue X-rayed utilizing charge coupled devices or CCDs, with computer enhancement software designed to increase the sharpness of contrast between portions of the image most indicative of particular lesion structures of possible interest. This CCD-based imaging system offers such advantages in visualization and differentiation of nonpalpable lesions that contrast resolution and system sensitivity exceed that available with conventional screen or film X-ray mammography, often permitting definitive diagnosis of equivocal findings without the need for biopsy. Visualization capabilities are further increased by electronic image processing techniques to enhance contrasts. Delays in film development and evaluation are eliminated by the systems of the present invention, providing virtually instant confirmation of proper biopsy needle placement, reducing patient discomfort during this critical phase of the procedure.

This virtually real time imaging of the stereotactic X-ray images, and their computer enhancement, are preferably facilitated by an optical system interposed in the position normally occupied by the X-ray film cassette. This preferred optical system employs a phosphor screen exposed to the arriving X-rays passing through the breast tissue, and the image created on the phosphor screen by the arriving X-rays is reflected by a mirror surface provided by a pellicle reflector, comprising an extremely thin sheet of select optical grade nitrocellulose, on the order of five to nine microns in thickness, stretched like a drumhead over a black anodized flat metal frame and bonded to the precision lapped edge of the frame. The X-radiation passes directly through this thin film to the phosphor screen, while the visible light image of the phosphor screen is reflected from the film's underside directly toward the camera lens, due to a reflective coating of metallic material such as aluminum silicate, deposited on the underside of the thin film. Suitable coatings produce up to nearly sixty percent reflectance, depending upon wavelength. In a preferred embodiment, a second flat mirror surface redirects the reflected image, thereby producing a compact folded optical system conveniently enclosed in a light-tight housing occupying very little more space than conventional X-ray film cassettes and associated film holder structures. The preferred camera is Peltier cooled, and incorporates a rectangular CCD format with one thousand or more pixels along each orthogonal edge.

The comfortable table for supporting the patient in the prone position with minimum distortion of normal breast configuration cooperates with the stereotactic X-ray projection system mounted directly under the table. When desired, the folded CCD imaging system replaces the normal X-ray film cassette, and the unique software enhances the contrast and sharpness of the resulting virtually real time image. Preferably the image-receptor and the X-ray tube are mounted on the same angularly movable C-arm, assuring that the X-ray image is always perpendicular to the optic axis of the arriving X-rays. This permits a bucky grid to have all of its grid planes permanently aligned with the X-ray source, minimizing lateral scatter radiation and producing X-ray images of maximum sharpness and clarity.

These aspects of the invention all combine to produce a highly useful prone patient-supporting table for X-ray mammography and an effective stereotactic mammography system serving to minimize patient discomfort and trauma while permitting highly precise location and needle biopsy of suspected breast lesions, avoiding invasive surgery in a large number of cases.

Thus, a principal object of the present invention is to provide highly precise mammography systems providing uniquely accurate images of the observed breast structures of the patient.

Another object of the invention is to provide such systems incorporating prone patient supporting tables designed to expose the breast for mammographic examination while also assuring its undistorted orientation and the optimum comfort and relaxation for the patient during the procedure.

Still another object of the invention is to provide such systems with the capability for accurate guidance of needle biopsy procedures employing virtually real time electronic imaging and needle placement verification, eliminating delays for film cassette loading, changing, unloading, developing and evaluation.

A further object of the invention is to provide such systems which are capable of stereotactic imaging of the maximum volume of the patient's breast tissue to provide three dimensional location of internal lesions or other internal sites requiring surgical examination.

A still further object of the invention is to provide folded CCD optical systems taking advantage of large CCD devices to provide extremely high resolution images of the patient tissue sites under study.

Another object of the invention is to provide digital X-ray image processing techniques using window and level manipulation, region of interest analysis, filters and edge enhancement, providing definitive X-ray diagnosis in many cases.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

THE DRAWINGS

For a fuller understanding of the nature and following detailed description taken in connection with the accompanying drawings in which:

FIG. 16 is a top plan view of the thin film pellicle mirror employed in the optical system of FIG. 15;

FIG. 17 is an edge elevation view of the same pellicle mirror;

BEST MODE FOR CARRYING OUT THE INVENTION

Three principal components or sub-assemblies are incorporated in the preferred embodiments of the present invention. These are the adjustable and versatile prone patient supporting table shown in FIGS. 1-7C, the novel CCD imaging folded optical system shown in FIGS. 11, 12 and 15-17, and the image enhancement and data display monitor systems providing high resolution and nearly real time image displays in the systems of the invention as illustrated schematically in FIG. 18.

Figure 1:
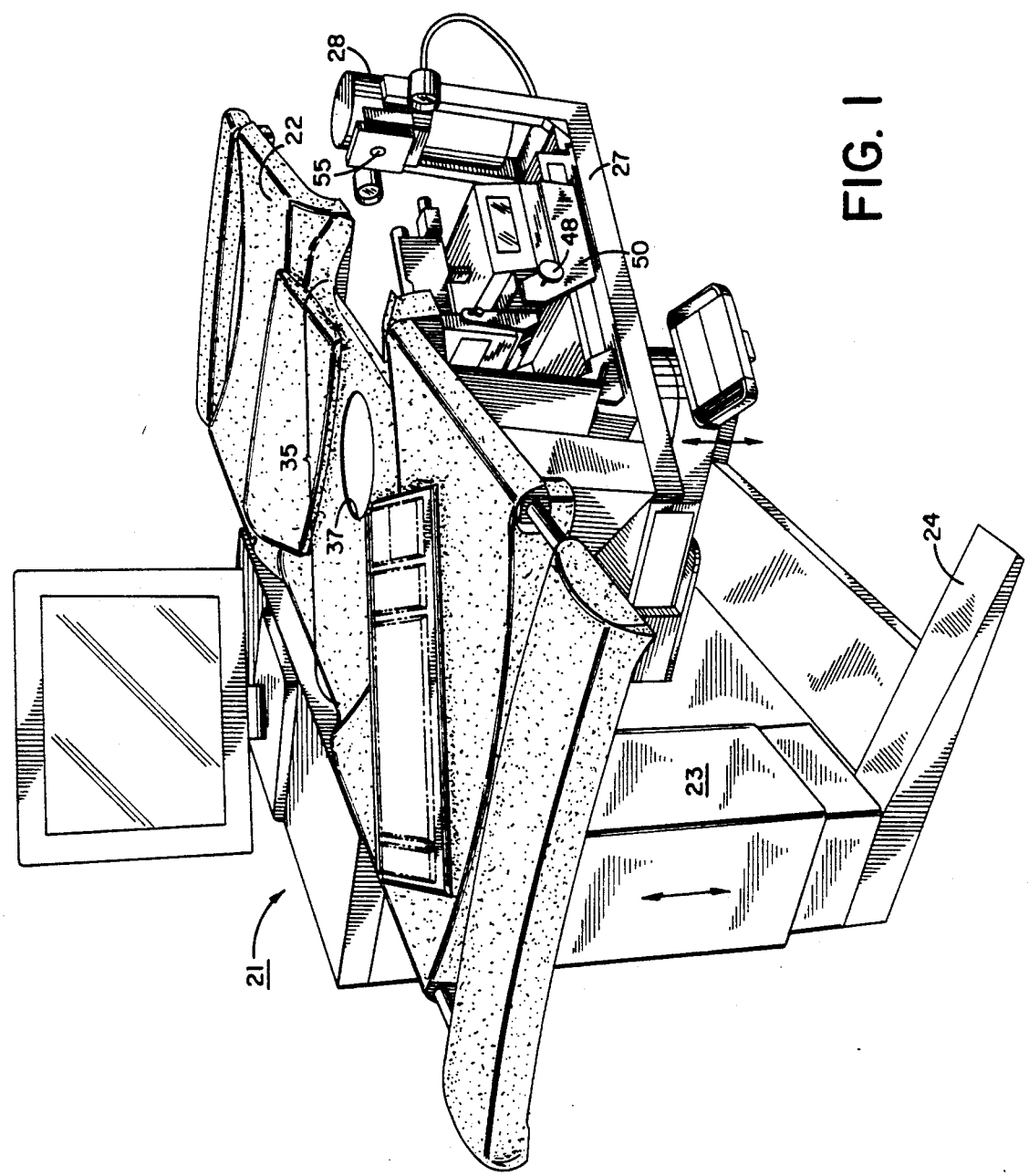
FIG. 1 is a top perspective view of the prone patient supporting mammography table of the present invention.

Patient supporting table 21 comprises platform 22 on which the patient rests in a prone position, supported by a rear pedestal 23 upstanding from the rear portion of a base 24, all as shown in FIG. 1. Pedestal 23 preferably incorporates table elevating means to raise and lower the table within limits for convenience of the patient and attending personnel.

Protruding forward over the lower part of base 24 from the front face of pedestal 23 is a ledge 26 sturdily constructed to provide underlying support for an angularly movable "C-arm" 27. Arm 27 is shaped like a letter C lying on its back, with one upstanding end mounting the X-ray source or mammography unit tube head 28. The pivot axis 29, about which C-arm 27 is mounted for angular rotation relative to ledge 26, is close to the opposite upstanding end of the C-arm 27, and this upstanding end incorporates either X-ray film cassette 31 or CCD sensor folded optical system 32 enclosed in a light-tight housing and shown schematically in FIGS. 11 and 12, and in the perspective top view of FIG. 15.

Figure 2:
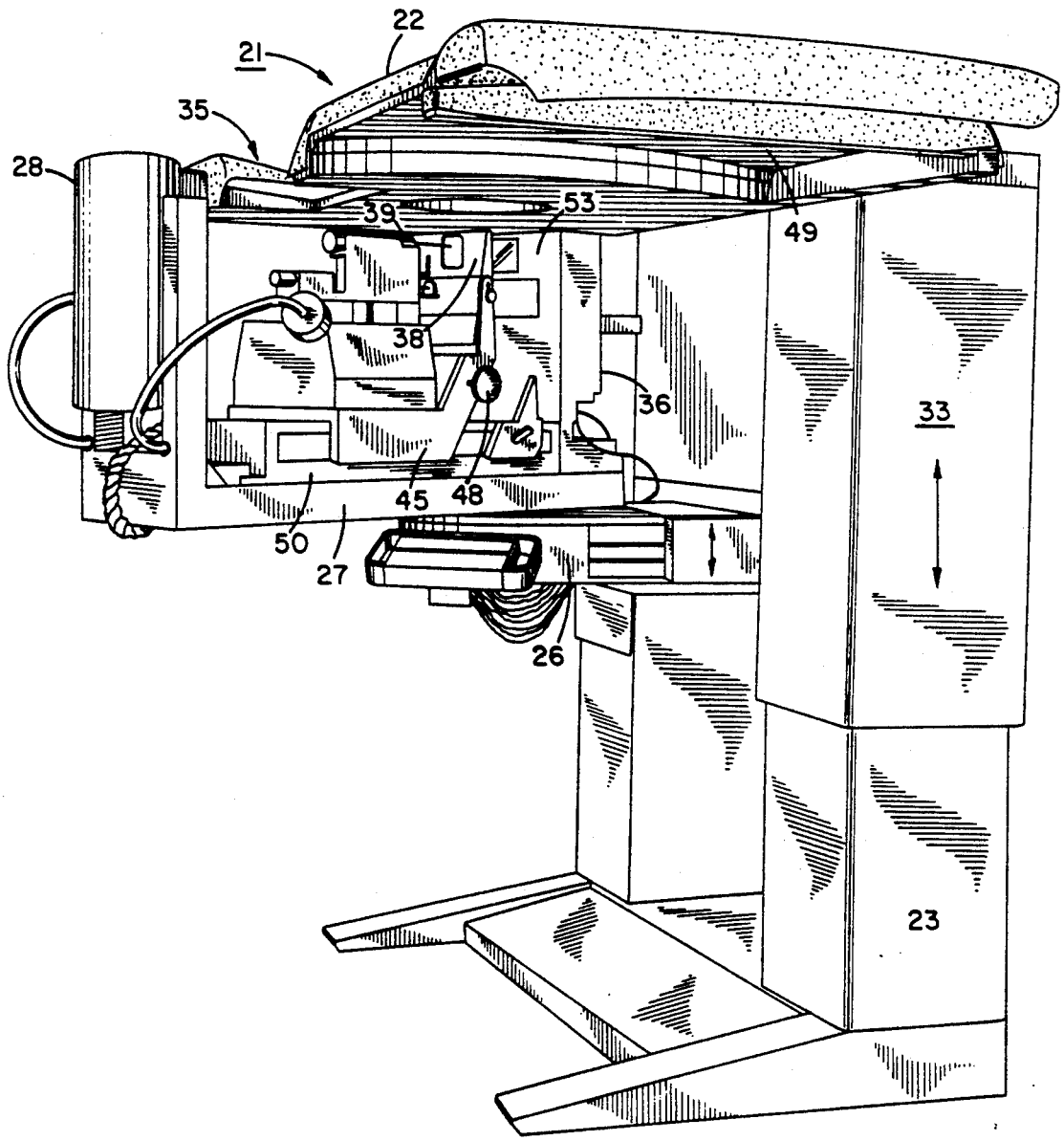
FIG. 2 is an end perspective view of the same table showing the base, pedestal and angularly movable C-arm carrying the X-ray tube and the image receptor, as well as the separate compression arm carrying compression plates and needle guide.
Figure 3:
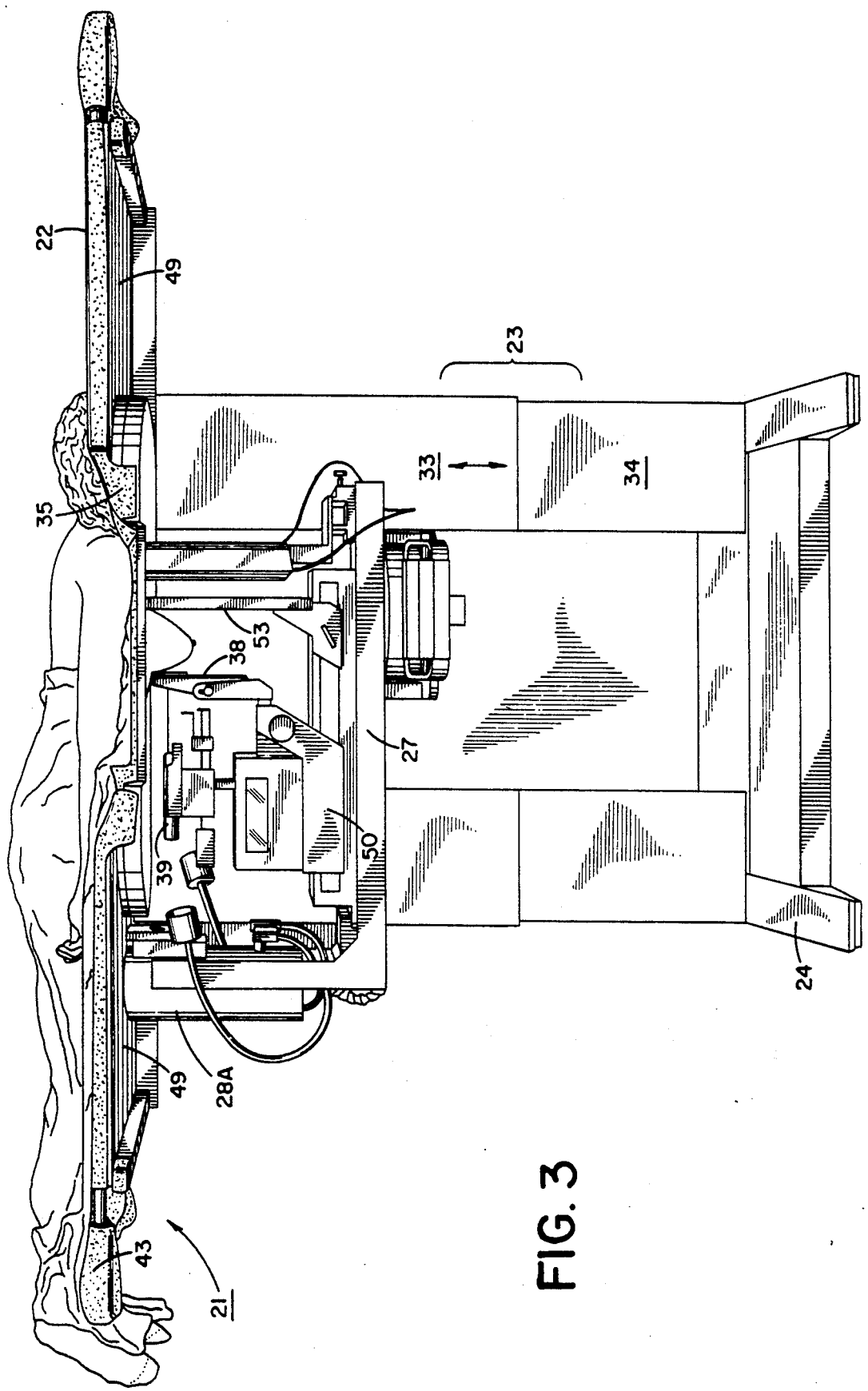
FIG. 3 is a front elevation view of the same table supporting a prone female patient at maximum elevation above the floor, delivering X-radiation to the underside of the breast, toward the table's right end.

As indicated in FIGS. 1-3, the upper portion 33 of pedestal 23 supporting the table platform 22 at its upper end and the ledge 26 at its lower end is capable of vertical downward movement from the raised position shown in FIG. 3 to a lowered position in which the ledge 26 is close to base 24, shown in FIG. 1. This vertical adjustment motion is provided by telescoping upper pedestal portion 33 over the underlying lower pedestal portion 34 shown in FIG. 3.

Further adjustability of the system is provided by separate vertical adjustment of ledge 26 relative to upper pedestal 33.

Ideally, the uppermost position 28A of tubehead 28 places it within the underside recess 49 formed in table platform 22 (FIG. 3) with the opposite end of the C-arm 27 comprising the image receptor 36, carrying either the X-ray film cassette 31 or the optical system 32, preferably being closely positioned adjacent the underside of table 22 as shown in FIG. 3, in order to bring the X-ray beam and the image receptor as close as possible to the chest wall of the patient lying prone, face down on platform 22.

Figure 4:
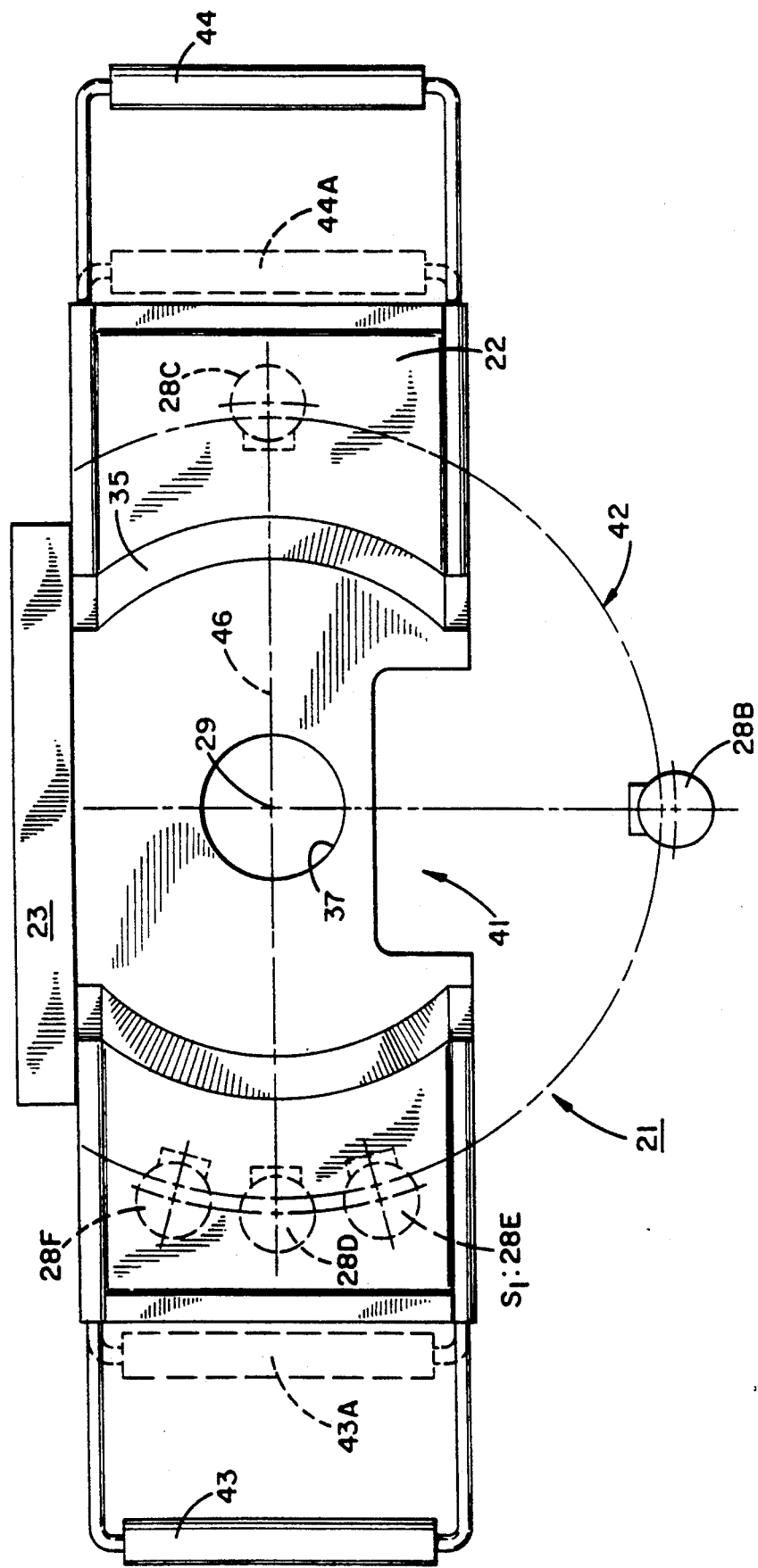
FIG. 4 is a schematic top plan view of the table showing the range of X-ray tube positions made possible by the rear pedestal construction of the unit.
Figure 5:
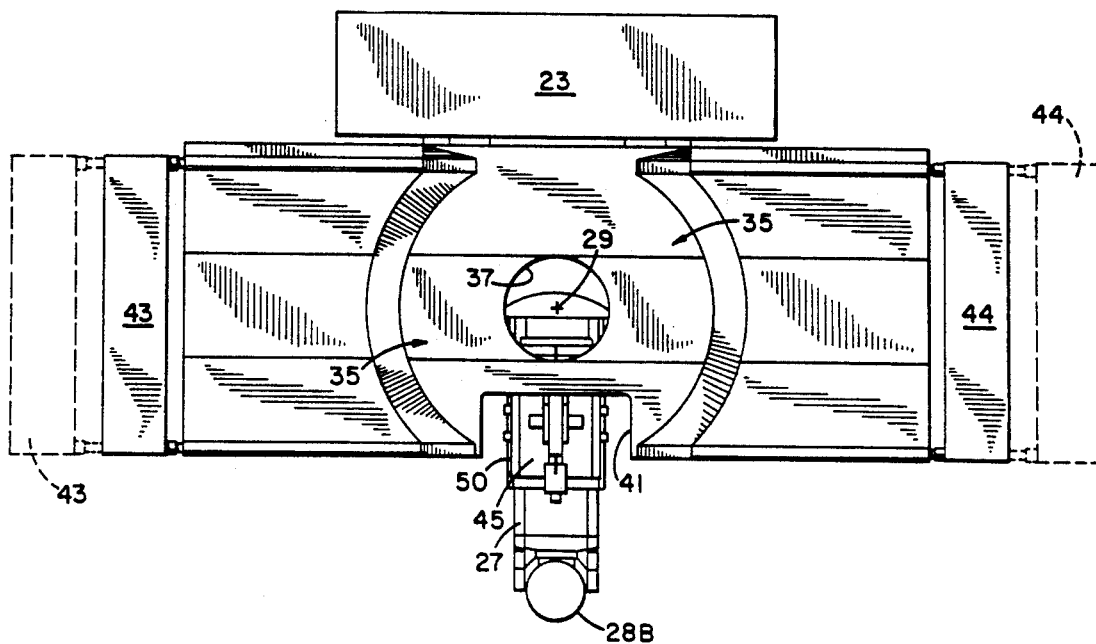
FIG. 5 is a top plan view of the table of FIGS. 1-3, with the C-arm positioned for delivering X-radiation from the side of the patient.

As shown in FIGS. 1, 4 and 5, a central aperture 37 is provided in the central portion of platform 22 accommodating one or both of the female patient's breasts depending therethrough as the patient lies face down on platform 22. Since image receptor 36 is relatively thin, as shown in FIGS. 3 and 5, and is positioned close to the pivot axis 29 about which the C-arm moves angularly, the pivoting movement of C-arm 27 about axis 29 allows the image receptor 36 to be positioned between the patient's breasts, or against the underside of either breast, by making minor adjustments in the position of axis 29 relative to ledge 26.

A fixed compression plate 53 and a compression paddle 38 movable toward and away from plate 53 are mounted above the C-arm 27 on an independently pivoted compression arm 50. Compression paddle 38 may be considered a biopsy compression device, since it incorporates both a transparent portion permitting X-rays to pass through it toward the patient's breast and image receptor 36, and a central needle access aperture. The compression arm 50 also incorporates mechanism for attaching a needle guide 39 for performing a needle biopsy without releasing the breast from the compression plate, thereby assuring that the target lesion coordinates determined by the original stereotactic measurements will be maintained upon insertion of the needle to reach the same target lesion coordinates.

The preferred form of table 22 shown in FIGS. 1 through 6 incorporates an additional useful feature, a central concave torso depression 35 surrounding the central aperture 37. Depression 35 provides comfortable support for the prone patient's head, shoulders and torso, with her hips and legs extending either to the right or to the left over the slightly higher end portions of table 22, which may also incorporate the footrests 43 and 44 if desired.

The central position of aperture 37, and the footrests 43 and 44 at both ends of the support tables 22 or 22A, provide double the 210° range of available X-ray projection angles indicated in FIG. 4, a range of some 420°. No conventional mammography tables are known to afford such a wide range of projection angles.

The slight elevation of the patient's hips by depression 35 maintains the normal relaxed curve of the patient's vertebra, while presenting the maximum possible volume of breast tissue through aperture 37 for X-ray examination. In addition, the slight elevation of the ends of table 22 outside of the central depression 35 provides the underside recess 49 encircling aperture 37, with vertical clearance for the upper end of X-ray tubehead 28 under table 22. This permits the focal point source FP of X-radiation to be elevated to a level nearly in tangent coincidence with the lower rim of aperture 37, providing desirable exposure of the maximum volume of the patient's pendulant breast tissue for examination.

The front edge of platform 22 beside aperture 37, opposite pedestal 23, is preferably formed as a removable panel 41, providing unimpeded access beneath platform 22 for the radiologist and technicians, and permitting the patient's arm to be lowered through the open space left by the removal of the panel 41 (FIG. 4) bringing her shoulder comfortably down toward the level of aperture 37 (FIG. 3) and minimizing any distortion or stretching of the breast pendulant through aperture 37.

Different positions of tubehead 28 produced by angular movement of C-arm 27 are illustrated in FIGS. 3-6, along the circular arcuate path 42 shown in FIG. 4. In the outermost tubehead position 28B, shown in FIG. 4 and FIG. 5, X-radiation projected toward axis 29 will approach a lesion from the lateral aspect of the right breast or the medial aspect of the left breast if the patient's head is positioned to the right on platform 22, as in FIG. 3. The footrest 43 at the left end of platform 22 is preferably extended to support the patient's legs in this position, while the footrest 44 at the right end of platform 22 is preferably retracted toward the table end to the dash line position 44A shown in FIG. 4. With the patient's head placed to the left of axis 29 in FIG. 4 and the footrest 44 being extended to its solid line position at the right end of platform 22, X-radiation from tubehead position 28B approaches the lateral aspect of the left breast or the medial aspect of the right breast. At either axial position, 28C near the right end of platform 22, or 28D near the left end of platform 22, the X-radiation approaches the breast from either above or below, with the image receptor 36 being positioned on the opposite side of the breast and the compression plate 53 and paddle 38 assuring that the patient is comfortably positioned with no risk of unexpected movement during the procedure.

In most cases, the tubehead 28 delivering X-rays to the patient will be positioned at the patient's head end of platform 22 with image receptor 36 and compression plate 53 being positioned on the underside of the pendulant breast and the compression paddle 38 being positioned on the upper side of the breast, both mounted on compression arm 50, which also provides support for needle guide 39 from this upperside when required. However, the presence of a lesion near the underside of the breast may indicate that the reverse orientation is preferred for minimum trauma, as indicated in FIG. 3, with the needle guide 39 and compression paddle 38 being positioned on the underside of the breast with the X-ray tubehead 28 being positioned beyond compression plate 53 on the upper side of the breast. In this position, the entry of the biopsy needle via needle guide 39 attached to compression paddle 38 into the underside of the breast tissue offers the minimum path length for access to the lesion, and this position may be preferred by many patients to assure that any needle scar will be on the underside of the breast where it is less easily observed.

Two additional tubehead positions 28E and 28F are also shown in FIG. 4, these being respectively displaced angularly by approximately 15 degrees counterclockwise and 15 degrees clockwise, which are typical angular displacements for stereotactic mammography. However, lesser angular amounts, of 10 degrees for example, on each side of the longitudinal axis 46 of platform 22 can be used if desired, to assure that the stereoscopically displaced images both fall on the desired portion of the image receptor, whether it be X-ray film in a film cassette 31 or the electronic imaging optical system 32 illustrated in the figures. Stereoscopic displacement of the lesion image may place it near the periphery of the total image plane in particular lesion orientations, and for this reason, a lesser stereo displacement of the positions 28E and 28F may be indicated.

Figure 7C:
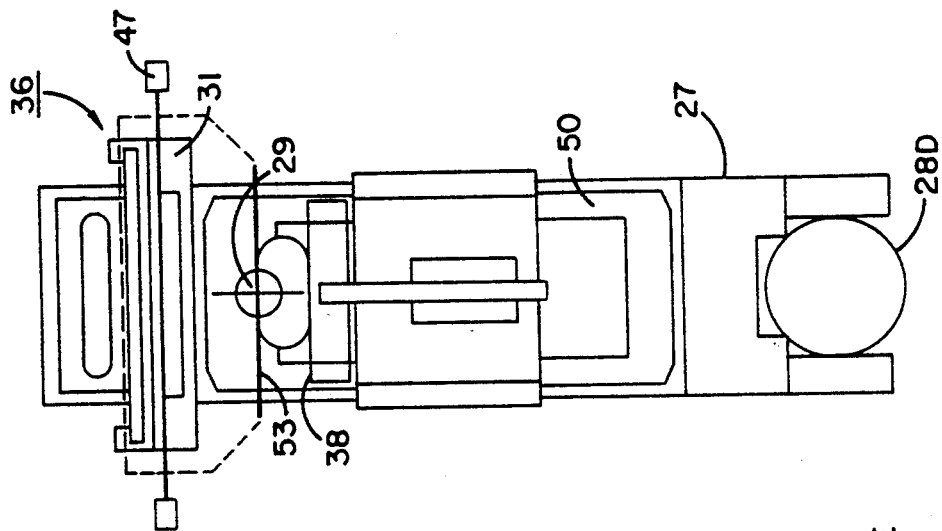
FIGS. 7A, 7B and 7C are corresponding successive fragmentary top plan schematic views showing the compression arm carrying the breast compression plates and needle guide in a fixed position beneath the table, while the underlying C-arm carrying the X-ray tube and image receptor is moved to different angular positions.
Figure 7B:
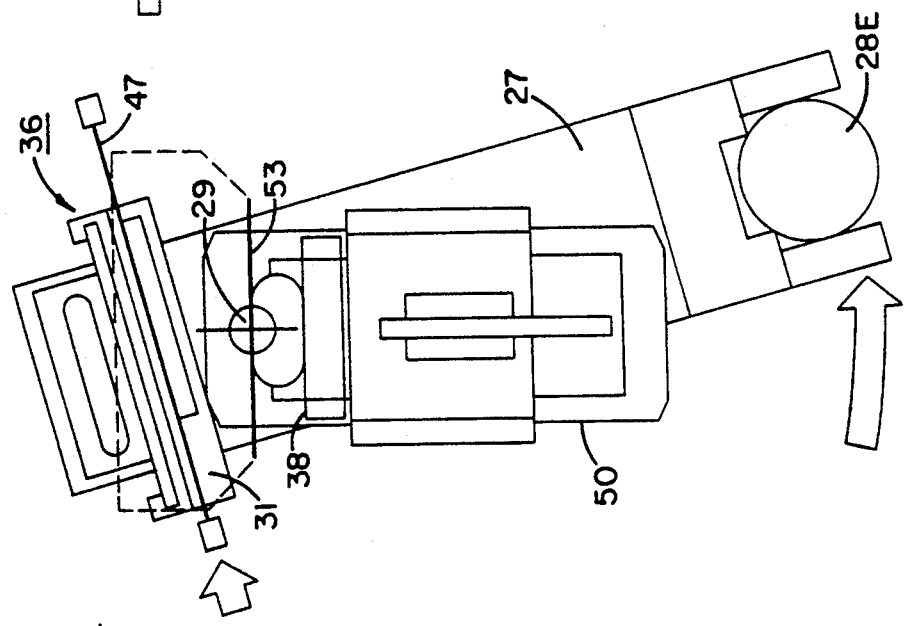
Figure 7A:
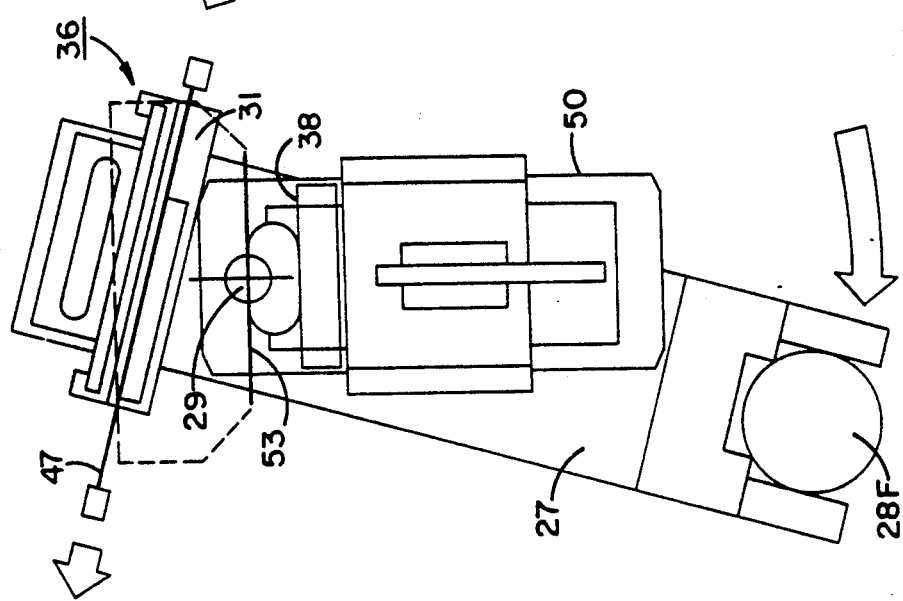

When the film cassette 31 is utilized at the image receptor 36 in stereotactic mammography, the cassette 31 may be provided with a film position shift lever 47, shown in FIGS. 7A-7C, and movement of this lever shifts the film cassette position so that stereo exposures at plus 15 degrees and minus 15 degrees angular displacement from axis 46 will be exposed side by side on the X-ray film. While the patient remains on platform 22 and the compression paddle 38 remains in position, the cassette may be removed and the film developed and examined to provide actual coordinates of the target lesion for needle biopsy. When the needle guide 39 is placed in position and the needle is inserted into the predetermined target tissue location, a new film cassette 31 may be placed in position on receptor 36 and two more stereo mammograms may be made to assure that the tip of the needle is at the desired location in the target lesion. Removal and development of this second cassette verifying the needle tip location thus permits any final adjustments required, and the needle biopsy may then be completed immediately.

X-, Y- and Z- axis indexing of needle guide 39 relative to the patient's breast tissue is provided by linear motorized adjustments mounted on an indexing carriage 45 movably mounted on linear bearings on the compression arm 50 pivoted on ledge 26 above pivoting tubehead C-arm 27. An indexing knob 48 cooperating with a timing belt or endless chain drive moves carriage 45 and compression paddle 38 into gentle compressive contact with the patient's breast 52, clamping it gently but firmly against the fixed breast compression plate 53. If fine needle biopsy is required, X, Y or Z control knobs on carriage 45 permit the operator to position the needle guide 39, adjusted for biopsy as required by the lesion coordinates found by stereotactic X-ray observations.

For convenience of notation, the X-axis is horizontal, extending toward pedestal 23; the Y-axis is vertical, extending upward toward the patient, and the Z-axis extends horizontally, parallel to table platform 22, toward X-ray tubehead source 28. The "pivot point" where pivot axis 29 intersects the X-Z plane passing through source focal point FP, is taken as the origin or zero-point for X, Y and Z values.

When the electronically enhanced CCD sensor optical system 32 is employed in place of the film cassette 31, a much shorter time is required for completion of the entire procedure. For example, the stereotactic procedure just described with two X-ray film cassettes customarily takes between 20 and 70 minutes during which time the patient must remain in the same position face down on the mammography table. With the electronic imaging systems incorporated in the preferred embodiments of the present invention, the digital image data received and processed in the system shown schematically in FIG. 18 ideally permits the mammography, the needle placement, the X-ray verification of needle location and the needle biopsy all to be completed within a period of one to two minutes, and certainly within a period far less than the 20 to 70 minutes normally experienced with customary X-ray film cassettes in stereotactic mammography. By minimizing the length of time a patient is required to remain in the same prone position, the patient's comfort and also the patient's relative immobility will be enhanced, minimizing inaccuracies which might be unavoidable if a patient were expected to lie still in the same position for a long period of time.

In addition to the very short time consumed by needle or core biopsy procedures when digital stereo CCD imaging is employed, there is a further important advantage achieved by the prone stereo mammography tables of this invention. As shown in FIG. 4, table 22 projects forward and is supported cantilever-fashion along its rear edge by rear pedestal 23. The wide clear open space under table 22 provides ample room for X-ray tubehead 28 to move pivotally through the infinite range of positions including those shown in the FIGURES: left longitudinal positions 28A or 28D (FIGS. 3, 4); stereo-offset positions 28E or 28F (FIG. 4); lateral position 28B (FIGS. 4, 5) and right longitudinal position 28C (FIGS. 4, 6).

Thus for a patient lying with her feet on left footrest 43, a range of 180°+15°+15° or 210° of right side tubehead positions are all available. If the same patient lies with her feet on right footrest 44, the full range of 210° of left side positions are equally available. Thus for the same patient, not just a 360° range but actually a 420° range of tubehead positions is readily available.

Figure 6:
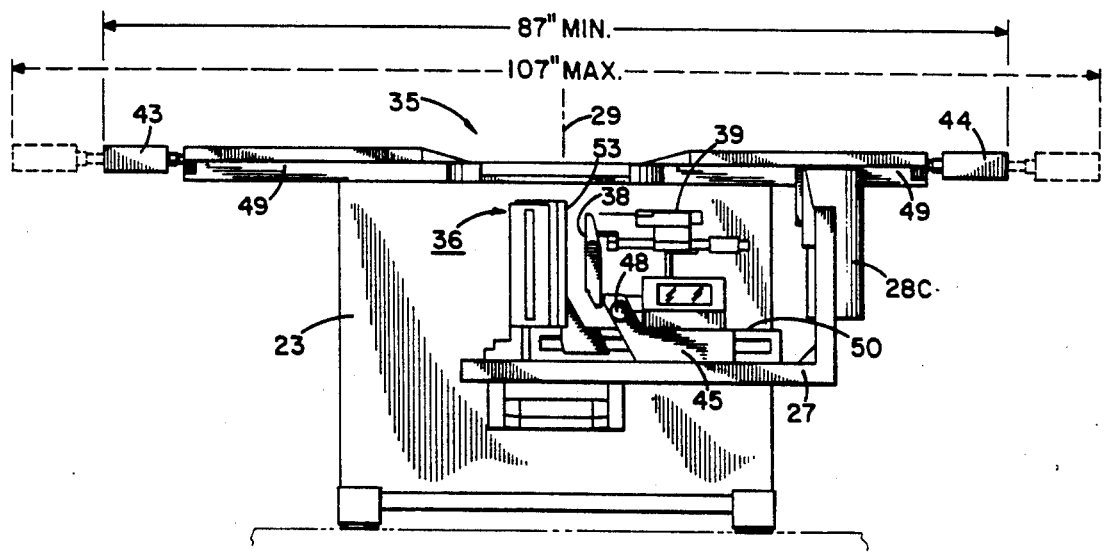
FIG. 6 is a schematic front elevation view of the same table, with the C-arm positioned for delivering X-radiation toward the table's left end.

The "gull-wing" longitudinal cross-section of table 22, best seen in FIGS. 3 and 6, with the shallow conical central depression 35 surrounding aperture 37, allows maximum patient comfort and excellent positioning of the pendulant breast to be examined, and also provides an added advantage over this entire 420° range. This is because both slightly raised "gull-wing" ends of table 22 create underside recesses 49 (FIGS. 2, 3 and 6), and X-ray tubehead 28 can thus be moved pivotally around the entire front 210° arcuate periphery of aperture 37 with its upper end projecting into recess 49. The tubehead's X-ray projection portal 55 (FIG. 1) positioned several inches below its uppermost end thus delivers its X-ray beam along a projection axis G=SID (FIG. 8) passing through a pivot axis 29 and perpendicular to image receptor 36, closely grazing the underside rim of aperture 37. This permits the maximum volume of breast tissue to be presented for mammographic examination over the infinite range of projection angles just described, with ample working space for radiologist and technicians beneath table 22, as indicated in FIGS. 2 and 3, for example.

Stereotactic Imaging System

Stereotactic imaging of breast tissue by projecting X-rays through the patient's compressed breast from two different source positions to produce two stereo images on an X-ray film is disclosed in detail in the Bolmgren article, supra, from the American Journal of Roentgenology for July 1977 and also in U.S. Pat. No. 4,727,565 to Ericson and 4,930,143 to Lundgren. Applicants' FIG. 13 shows a schematic diagram of such prior art two-source-position stereotactic X-ray mammography with a lesion 51 in the tissue of a patient's breast 52 compressed between a fixed compression plate 53 and an adjustable compression paddle 38, both of which are transparent to X-rays.

Figure 13:
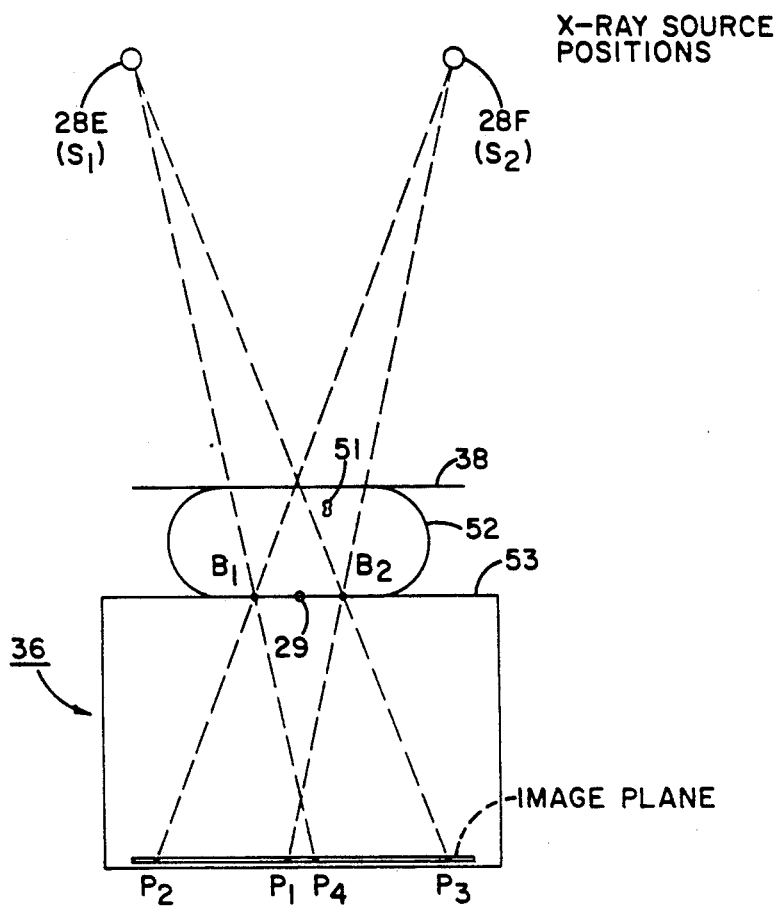
FIG. 13 is a top plan schematic view of the conventional stereotactic mammography procedure performed on prior art devices, showing the X-radiation arriving at significant angles of inclination from the perpendicular, introducing undesired image degradation, when the image receptor is stationary.

When image receptor 36 is stationary, the fixed compression plate 53 preferably coincides with the position of image receptor 36 shown in FIG. 13 and comprises the proximal surface of receptor 36.

When image receptor 36 of the present invention is mounted on the C-arm 27 for pivoting movement with the X-ray tubehead 28 source FP, as shown in FIGS. 2, 3 and 6-12, receptor 36 is spaced far enough behind pivot axis 29 to afford clearance for the desired angular pivoting motion.

An additional advantage of the mounting of the image receptor on the C-arm arises from the usefulness of bucky grids with divergingly slanted vanes to pass direct X-radiation from the source FP while blocking laterally scattered or secondary X-radiation which would otherwise reduce image sharpness. When the bucky grid is mounted on the image receptor 36 pivoting with the tubehead C-arm 27, its diverging vanes are aligned with source FP in all of its adjusted stereo positions shown in FIGS. 7A and 7B. By contrast, a stationary bucky mounted in front of the image plane in the prior art image receptor of FIG. 13 can have its vanes aligned with only one X-ray source point, interfering with some of the desired direct X-radiation projected from other, offset source points and seriously reducing the bucky's usefulness.

The determination of X-, Y- and Z- coordinates of suspect lesions is performed by calculating the equations of slope for the X-ray paths passing through the lesion and through a reference point 40 on the compression 38 to a first image plane for the first source position S1 or 28E (FIGS. 4, 8) and for the second source position S2 or 28F.

Figure 8:
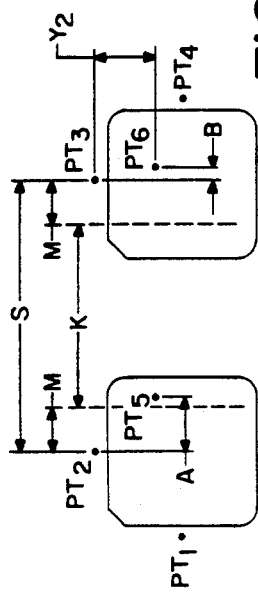
FIG. 8 is a schematic diagram of the stereotactic mammography procedure of this invention, comparing the X-radiation paths through a suspect lesion and a reference point on the compression plate for two angularly offset tubehead source positions, when the image receptor pivots with the tubehead on the C-arm.
Figure 9:
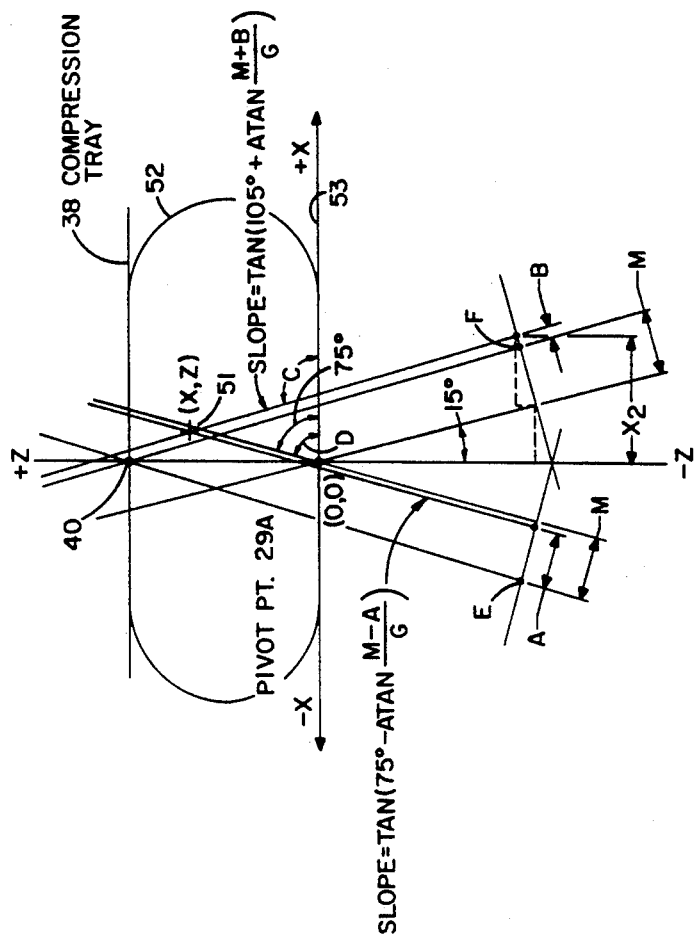
FIG. 9 is a fragmentary enlarged schematic diagram showing the lower end of FIG. 8 in more detail.
Figure 10:
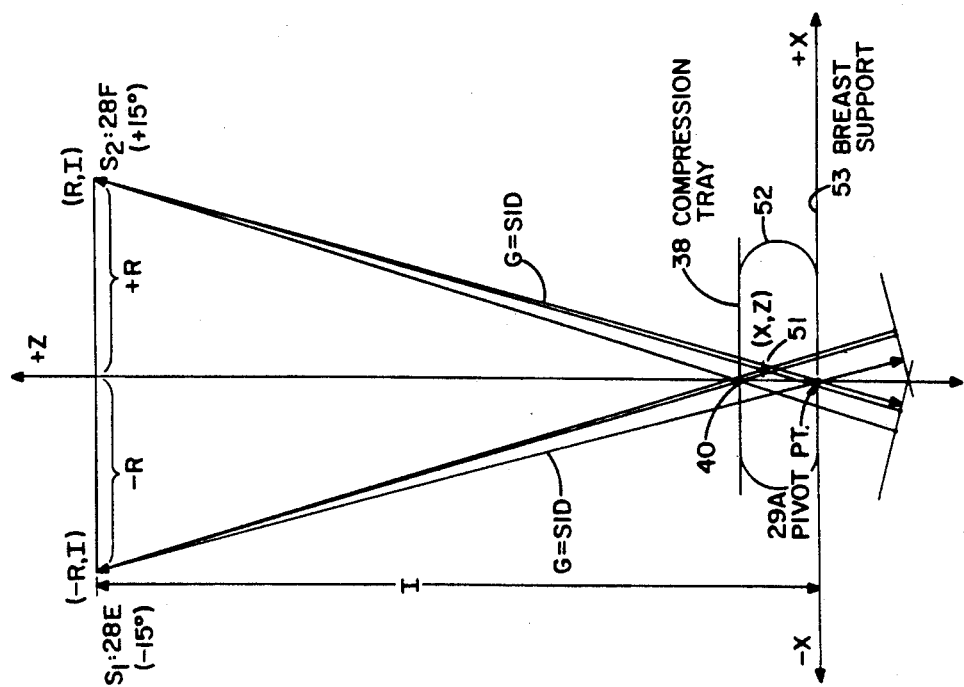
FIG. 10 is a schematic diagram of the two images produced at the image receptor by X-radiation from the same two source positions.

In FIGS. 8, 9 and 10, the coordinates of the suspect lesion 51 are X, Y and Z. Points 1 and 2 are the Y and X positions of the reference hole 40 image on the left image area in FIG. 10, produced when the source is at S2 or 28F. Points 3 and 4 are the X and Y positions of the hole 40 image on the right image area, produced when the source is at S1 or 28E. Points 5 and 6 are the images of the suspect lesion 51 in the two image areas of FIG. 10.

This method is based on finding the equations of the two source-to-image lines for the two lesion images. The intersection of the two lines provides the X, Y and Z coordinates, on the X-Y, Y-Z and X-Z planes.

Diagrammatic FIG. 8 shows the X-Z plane as viewed from below. The pivot point, where the pivot axis 29 passes through the X-Z plane, serves as the zero point for both X and Z values, for analytical purposes.

Diagrammatic FIG. 9 is an enlarged view of the portion of the same diagram around the pivot point.

The source-to-image lines for the image created when the tubehead source is in the left position (−15°), indicated by position S1 or 28E in the other figures is:

$$X - X1 = \frac{Z - Z1}{ML} \qquad [EQ. 1]$$

$X1 = -R; Z1 = I;$
$Z =$ distance from pivot point to lesion $$X = \frac{Z - I}{ML} - R$$

$$ML = \tan C = \tan\left(105° + \arctan\frac{M + B}{G}\right)$$

$$= \frac{\tan 105° + \frac{M + B}{G}}{1 - \tan 105° \times \frac{M + B}{G}}$$

where
G = SID, the source-to-image distance
M = distance from projected pivot point to compression reference hole 40 images E, F (see FIGS. 8, 9 and 10).
B = distance between reference image (point 3) and lesion image (point 6).

The source-to-image lines with the source in the right half (or +15°) position S2 or 28F is:

$$X - X1 = \frac{Z - Z1}{MR} \qquad [EQ. 2]$$

$X1 = -R; Z1 = I;$
$Z =$ pivot point to lesion $$X = \frac{Z - I}{MR} - R$$

$$MR = \tan D = \tan\left(75° + \arctan\frac{M - A}{G}\right)$$

$$= \frac{\tan 75° + \frac{M - A}{G}}{1 - \tan 75° \times \frac{M - A}{G}}$$

$A =$ distance between reference image (point 2) and lesion image (point 5).

Solving for Z:

[EQ. 1] = [EQ. 2]

$$\frac{Z - I}{ML} - R = \frac{Z - I}{MR} + R$$

-continued $$Z = \left( \frac{2R}{\frac{1}{ML} - \frac{1}{MR}} \right) + I$$

height (by similar methods using $-15°$ image)

$$Z() - Z1 = MT(X - X1)$$

$$MT = \tan\left(105° + \arctan\frac{M}{G}\right)$$

$$= \frac{\tan 105° + \frac{M}{G}}{1 - \tan 105° \times \frac{M}{G}}$$

$$Z() = R\frac{\tan 105° + \frac{M}{G}}{1 - \tan 105° \times \frac{M}{G}} + I$$

Lesion depth $= \left( \frac{2R}{\frac{1}{ML} - \frac{1}{MR}} + I \right) - (RMT + I)$ $$= \left( \frac{2R}{\frac{1}{ML} - \frac{1}{MR}} \right) - RMT$$

Finding $X$:

$$(X + R)ML + I = (X + R)MR + I$$

$$XML + RML + I = XMR + RMR + I$$

$$X = -R\left(\frac{ML + MR}{ML - MR}\right)$$

Then $Y$:

$$\frac{X - X1}{X2 - X1} = \frac{Y - Y1}{Y2 - Y1}$$

$$Y1 = Y(\text{source}) = 0$$

$Y2$ is measured on film $PT3 - PT6$ (FIG. 10)

$$Y = (Y2 - Y1)\left(\frac{X - X1}{X2 - X1}\right) + Y1 \quad X1 = -R$$

$$= Y2\left(\frac{X - X1}{X2 - X1}\right)$$

$$= Y2\left(\frac{X + R}{X2 + R}\right)$$

$$X2 = (SID - FPD)\sin 15° + (M + B)\cos 15°$$

See FIG. 10

In FIGS. 8, 9 and 10, $$M = \frac{1}{2}(S - K)$$

| | |
|---|---|
| $K$ = FILM SHIFT | (74.5 mm) |
| $G$ = SID | (743.0 mm) |
| $FPD$ = FOCAL PT. − PIVOT POINT | (661.5 mm) |
| $R$ = FOCAL SHIFT = $FPD \sin 15°$ | (171.2 mm) |
| $I$ = $FPD \cos 15°$ | |

Digital Imaging System

Figure 12:
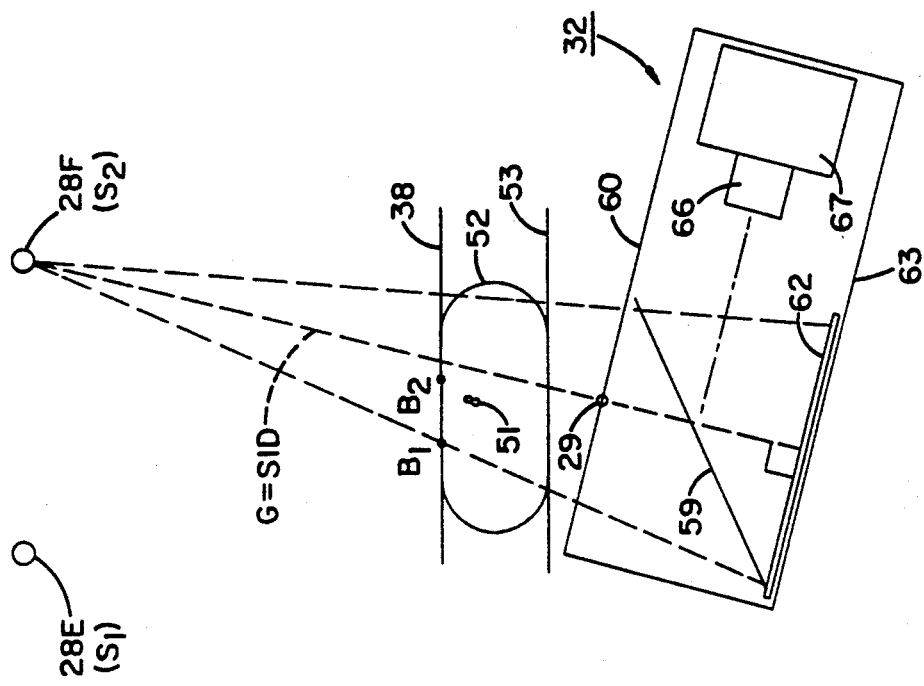
FIGS. 11 and 12 are schematic diagrams of the X-radiation paths for two angularly offset stereo tubehead source positions utilizing a folded CCD optical imaging system inserted in the position occupied by the X-ray film cassette in film mammography but with the digital CCD optical imaging system of FIGS. 13-17 pivoting with the tubehead.
Figure 11:
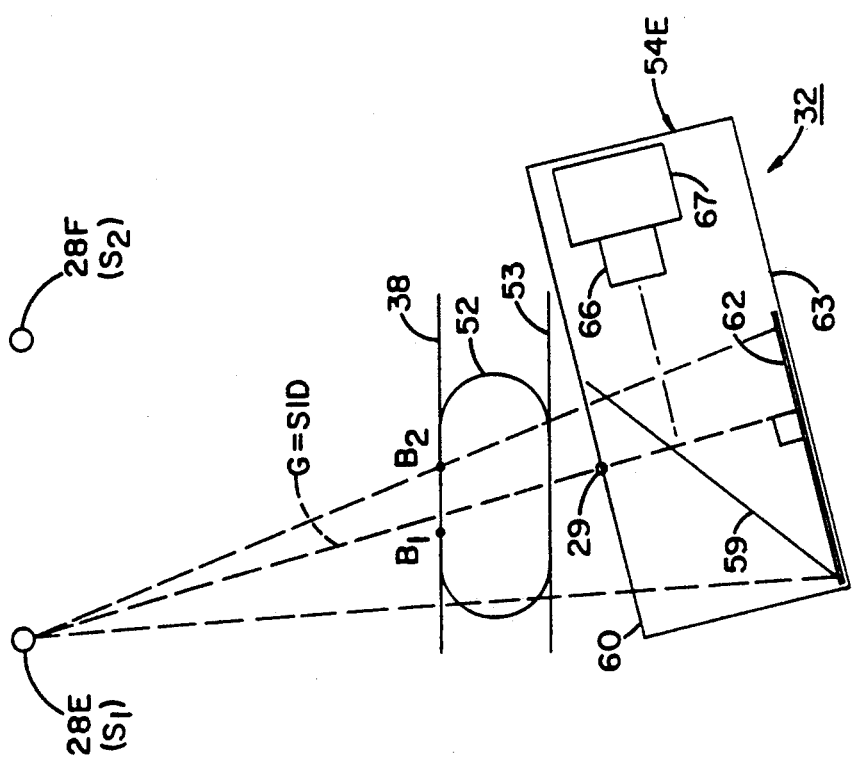
Figure 15:
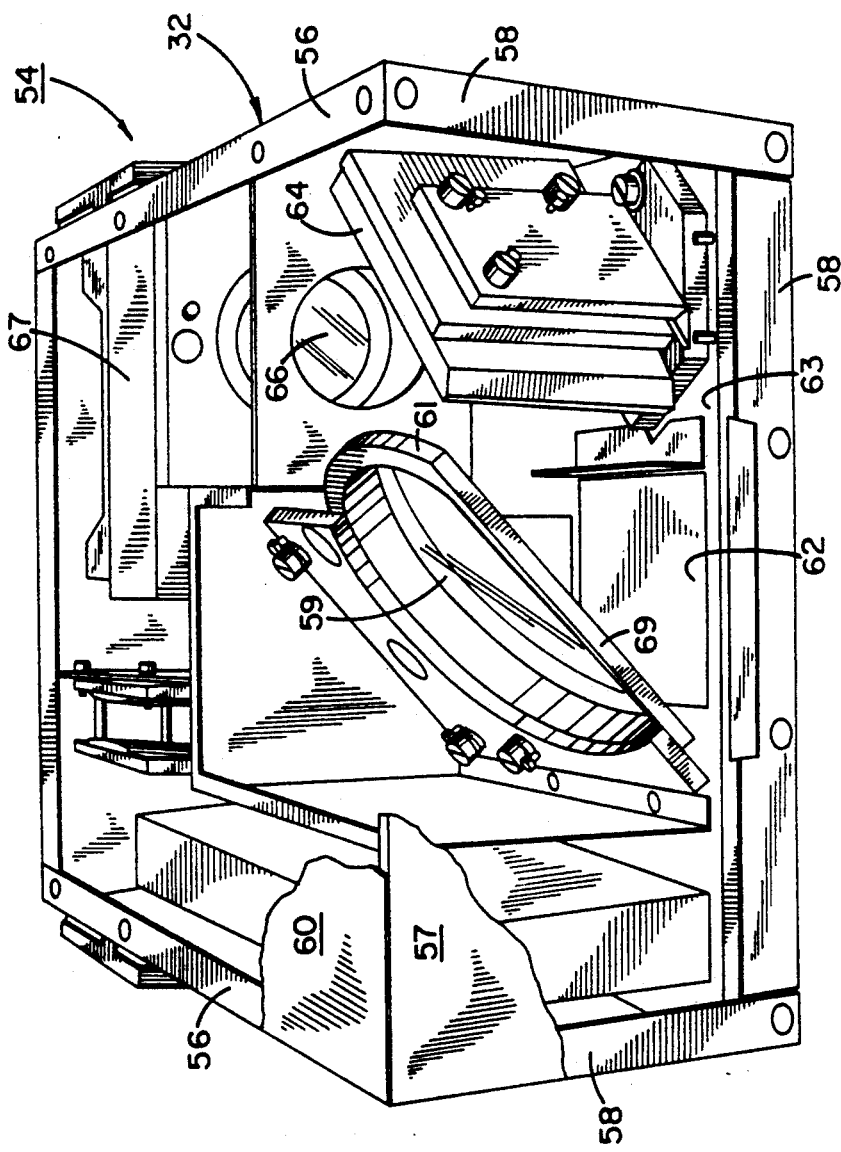
FIG. 15 is a perspective top view of the folded optical system employed in the stereotactic CCD imaging system of FIGS. 11 and 12, with a portion of the light-tight housing removed to reveal the location of the various components of the optical system.

The principal internal components of the folded optical system 32 are shown schematically in FIGS. 11 and 12, and in the cutaway top perspective view of FIG. 15, where the X-ray transparent cover plate 60 forming the proximal or front wall of housing 54 has been removed from its supporting proximal flanges 56, to reveal the internal structures inside housing 54. In the same manner, an upper housing panel 57 has been removed from its upper supporting flanges 58, thus revealing the internal structure of the optical system 32. Fragmentary broken away portions of panel 57 and cover plate 60 are shown at the left side of FIG. 15.

As indicated in FIGS. 11 and 12, radiation from the X-ray tubehead 28 passes successively through the X-ray transparent adjustable compression paddle 38, the patient's breast 52, the fixed compression plate 53, and then through a thin film pellicle mirror 59. This is a film of high tensile strength elastic membrane material such as nitrocellulose having a thickness ranging between 5 and 9 microns (micrometers), for example, stretched like a drumhead over a flat metal frame 61 (FIG. 15) and bonded to the precision lapped edge of this frame. The thin pellicle film is virtually transparent to X-radiation which passes directly through it to impinge upon the underlying phosphor screen 62 mounted on the image plane at the rear wall 63 of the housing 54.

Figure 14:
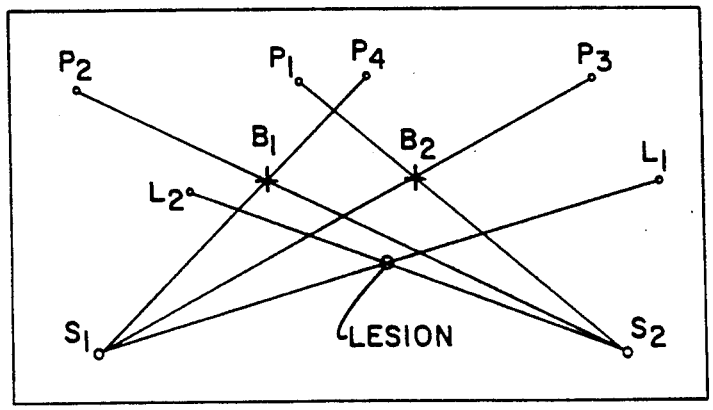
FIG. 14 is a schematic diagram illustrating the stereotactic images employed to identify the coordinates of the target lesion with the imaging system of FIG. 13.

Positioned at points B1 and B2 on the X-ray transparent fixed compression plate 53, in the prior art fixed image receptor of FIG. 13, are X-ray opaque index marks which may take the form of cross hairs as indicated in FIG. 14. These index marks are imaged as shown by the orosses B1 and B2 in FIG. 14, which comprises a vertical projection of the various points along the path of the X-rays proceeding through the system shown schematically in FIG. 13. Thus the point S1 in FIG. 14 corresponds to the vertical projection on the image plane of the source position 28E at which the tubehead 28 is first angularly offset, as indicated in FIGS. 4 and 13. In the same manner, point S2 on the image plane is the vertical projection of the second tubehead source position 28F shown in FIGS. 4 and 13.

The X-ray path from point 28E through X-ray opaque index B1 is imaged at point P4 on the image plane, while at the second source position 28F the X-ray passing through index point B1 is imaged at point P2 as indicated in the vertical projection diagram of FIG. 14, and these two X-ray paths projected on the image plane cross at the index point B1 shown in FIG. 14. In the same manner, index point B2 is determined by the crossing of the vertical projections of the X-ray paths S2P1 and S1P3

As also indicated in FIG. 14, the X-ray path from source S1 through lesion 51 creates the vertical projection X-ray path S1L1 on the image plane and the crossing of this projected line with line S2L2 indicates the position at which the lesion appears in the stereo projection of FIG. 14. When the coordinates of these points S1, S2, B1, B2 and L1 and L2 are determined on the image plane, this data may be recorded digitally and manipulated to provide highly accurate X, Y and Z coordinates for the actual position of the lesion.

This digital data handling operation is facilitated by the optical system 32, shown in FIGS. 11, 12 and 15–18. These include the coated underside of the pellicle mirror 59 which serves as a mirror reflecting the image of the image plane phosphor plate 62 toward a second mirror 64, which delivers the reflected image of the phosphor plate 62 to lens 66 of the CCD equipped camera 67.

Thus, as viewed from above looking down in FIG. 15, the image of the phosphor screen 62 is reflected from the underside of pellicle film 59 to the right toward the angularly positioned mirror 64 which then directs it downward toward the lens 66, clearly shown in FIG. 15 overlying the CCD camera 67.

Advantageously the pellicle film's reflective undersurface reflects the visible light image toward the CCD camera, avoiding any diffusion or losses from transmission through the phosphor plate 62. Also, the diagonal positioning of film 59 necessarily requires spacing plate 62 away from X-ray transparent cover plate 60. Phosphor plate 62 thus receives the direct X-rays passing from the tubehead through the target, but most secondary or scattered X-rays produced within the target are lost, leaving a clean, sharp resulting image on plate 62.

The camera, operating in the snapshot mode, integrates the image from the phosphor plate 62 and at the end of the exposure, the image is stored in computer memory. This operation is performed for the image produced by X-ray source position 1 at tubehead position 28E, and it is then repeated for source position 2 at tubehead position 28F and another exposure is made. Thus in a few seconds, two stereo pair images are obtained and stored in the computer. The operator then brings the images to the monitor and using a track ball, places cursor locators on the calibration marks B1 and B2 and on the lesion.

Based on the position of these cursors on the monitor screen, the computer then calculates the X, Y and Z location of the lesion relative to the breast compression paddle 38 and plate 53.

These X, Y and Z coordinates may be used immediately for fine needle or core biopsy, using the needle guide to direct the biopsy needle to the site of the lesion, where two more stereo images are recorded to confirm the accurate positioning of the needle tip at the lesion site. Alternatively, these images may also be employed to guide surgery if desired.

The pellicle film thickness preferably falls between five and nine micrometers, and most desirably falls within the range of six to seven micrometers, with the thickness uniformity being accurate and the faces of the film being parallel within two wavelengths of X-radiation per inch. A coating of aluminum and silicon dioxide on the underside of the pellicle film provides a reflectance greater than 8%, with no pinholes being visible to the unaided eye, thus assuring the uniformity of the resulting CCD image. While normal pellicle mirror frames 61 are ring shaped, the unique "D-shaped" configuration of the pellicle mirror 59 and frame 61 in the optical systems of the preferred embodiments of the invention provide a unique advantage: the rectangular area 68 corresponding to the pellicle film reflection of the phosphor plate 62 is uniformly smooth and flat over its entire surface and it will be noted that the circular sector of frame 61 subtends approximately 250 degrees, while the straight chord 69 closing the D-shaped frame 61 subtends the remaining angle of about 110 degrees. This D-shaped frame 61 thus brings the critical area 68 very close to the adjacent chord segment 69 of frame 61, as shown in FIG. 16. Chord segment 69 is positioned closely adjacent to upper housing panel 57, as can be observed in FIG. 15, thus bringing the critical area for imaging X-radiation passing through the patient's breast 52 close to table platform 22, and producing a visible image on the phosphor plate 62 in close juxtaposition with upper housing panel 57, which is positioned vertically as close as possible to the patient's chest wall. By this means, the maximum volume of the patient's breast 52 is exposed to the mammographic examination using the X-radiation passing through the D-shaped pellicle mirror 59.

FIGS. 7A–7C, 11 and 12 show the preferred embodiment of the invention in which the light-tight housing 54 is independent of fixed compression plate 53 and is mounted for pivoting movement on the C-arm with tubehead 28 about a pivot axis 29 spaced slightly away from fixed compression plate 53. Tubehead 28 and housing 54 thus pivot together as a unit, from position 28E–54E in FIG. 18 to position 28F–54F in FIG. 19. A substantial portion of the patient's breast 52 can then be viewed in each position, in a wide image utilizing virtually the full width of phosphor plate 62, as shown in these figures. As soon as CCD camera 67 has recorded the image produced by tubehead 28E, X-ray source S1, the C-arm 27 can be swung to tubehead position 28F, source S2, and the entire width of phosphor plate 62 is again available to receive the second stereo image.

FIGS. 11 and 12 show a second feature characterizing this embodiment: the X-ray opaque index marks B1 and B2, like reference hole 40, are positioned on movable compression paddle 38, rather than on fixed compression plate 53, to assure that diverging radiation paths from either source position passing through the index marks will fall within the useful image area of phosphor plate 62.

CCD Digital Imaging Optical System

Figure 19:
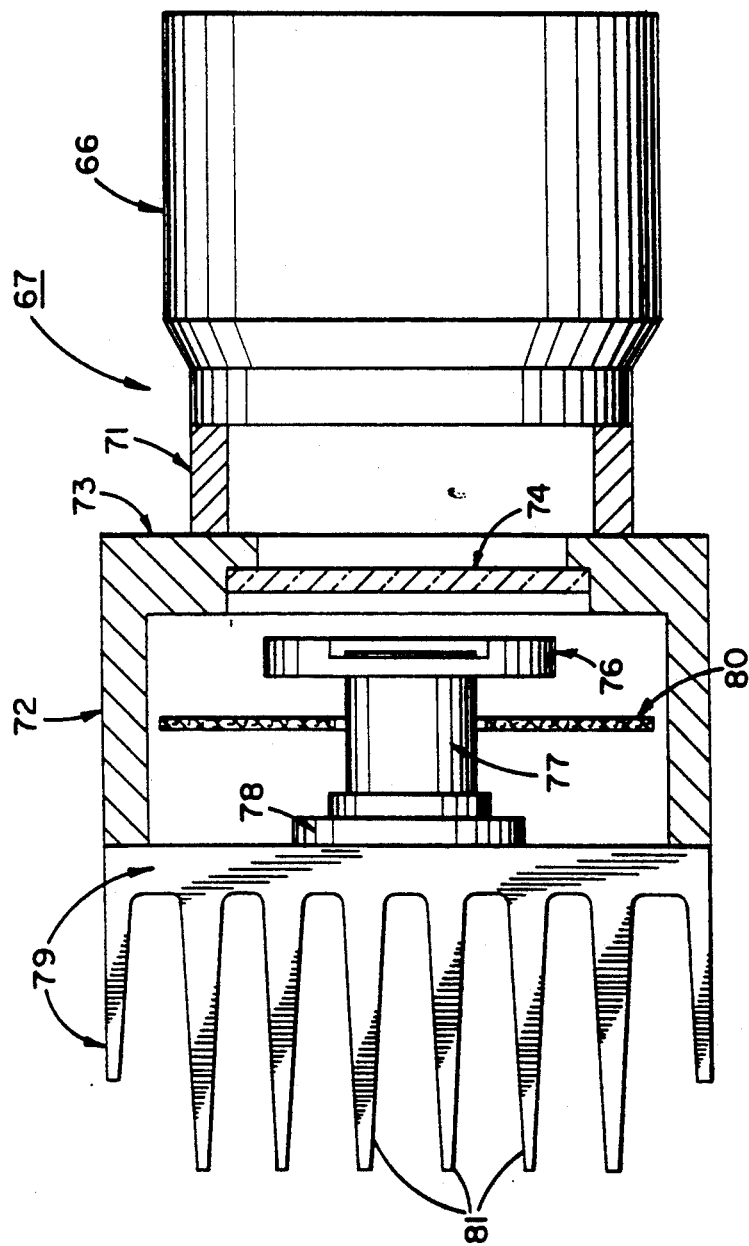
FIG. 19 is a detailed schematic diagram of a preferred form of CCD camera employed in the optical system of FIG. 15.

The preferred form of CCD Camera 67 is shown schematically in more detail in FIG. 19. In this diagram, lens 66 is supported on a lens mount 71 positioned on the front face 73 of camera body 72. Face 73 incorporates a light-transparent window 74 behind which CCD array 76 is positioned. Light focused by lens 66 is delivered through window 74 to a focal plane corresponding to the face of CCD array 76.

Array 76 is mounted on the front end of a "cold finger" pedestal 77 whose rear end is anchored to a Peltier thermoelectric cooler 78 mounted on the camera body's rear face 79 with heat-transfer fins 81 extending into the ambient atmosphere. A ring-shaped printed circuit board 80 closely encircles "cold finger" pedestal 77, minimizing resistance losses in the conductors (not shown in FIG. 19), connecting CCD array 76 to board 80.

CCD array 76, positioned at the focal plane of lens 66, receives a focused image of the light produced by phosphor plate 62 via mirrors 59 and 64, and the array is quickly scanned, facilitating the storing of the image in memory for manipulation, enhancement and future study as desired, without any delays such as those required for processing of X-ray film.

Figure 18:
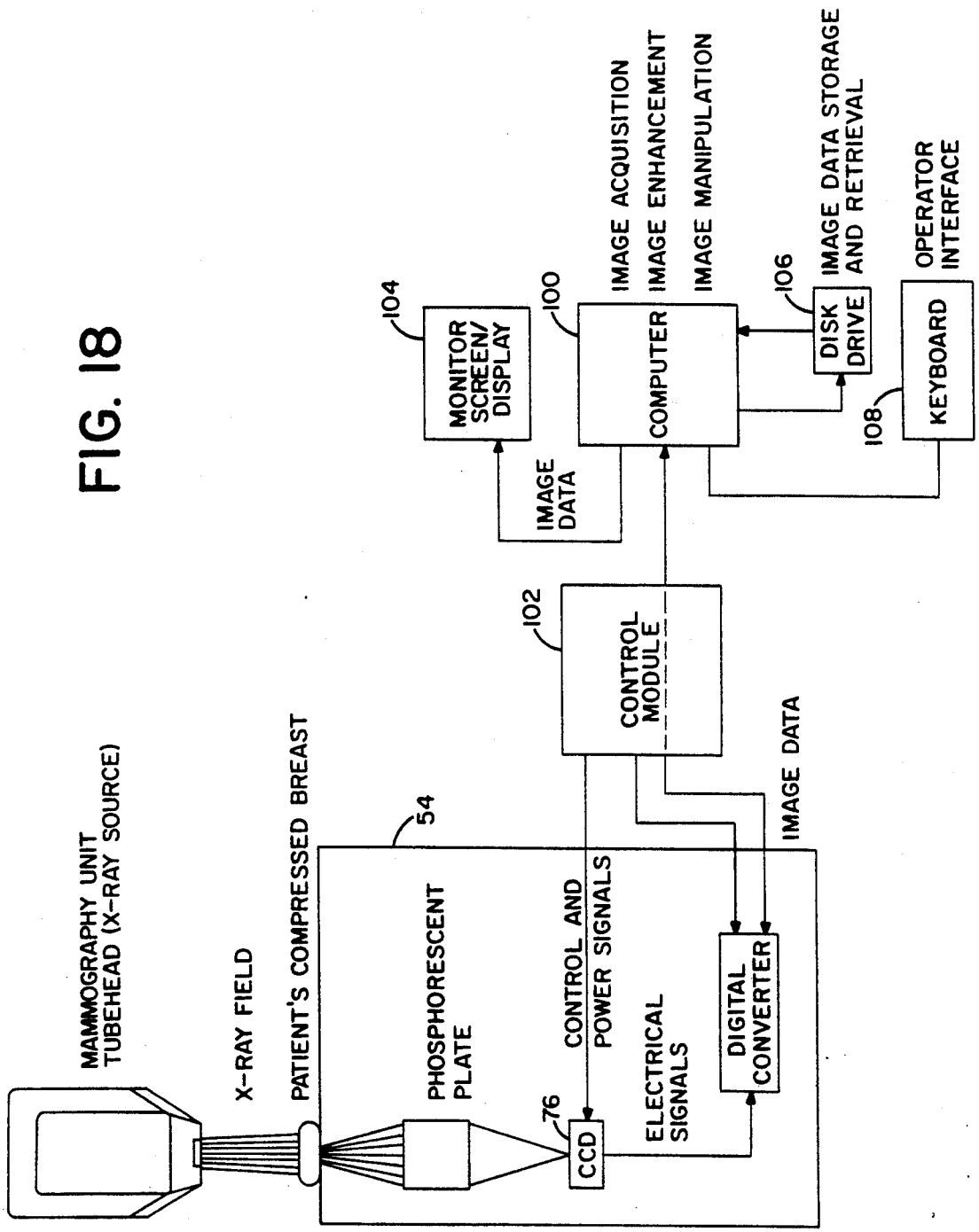
FIG. 18 is a schematic diagram showing the imaging of the patient's compressed breast on a phosphor plate in the optical system delivering a focussed image to the CCD sensor and the processing of the CCD output signals through the image enhancement computer to the monitor screen display.
Figure 20:
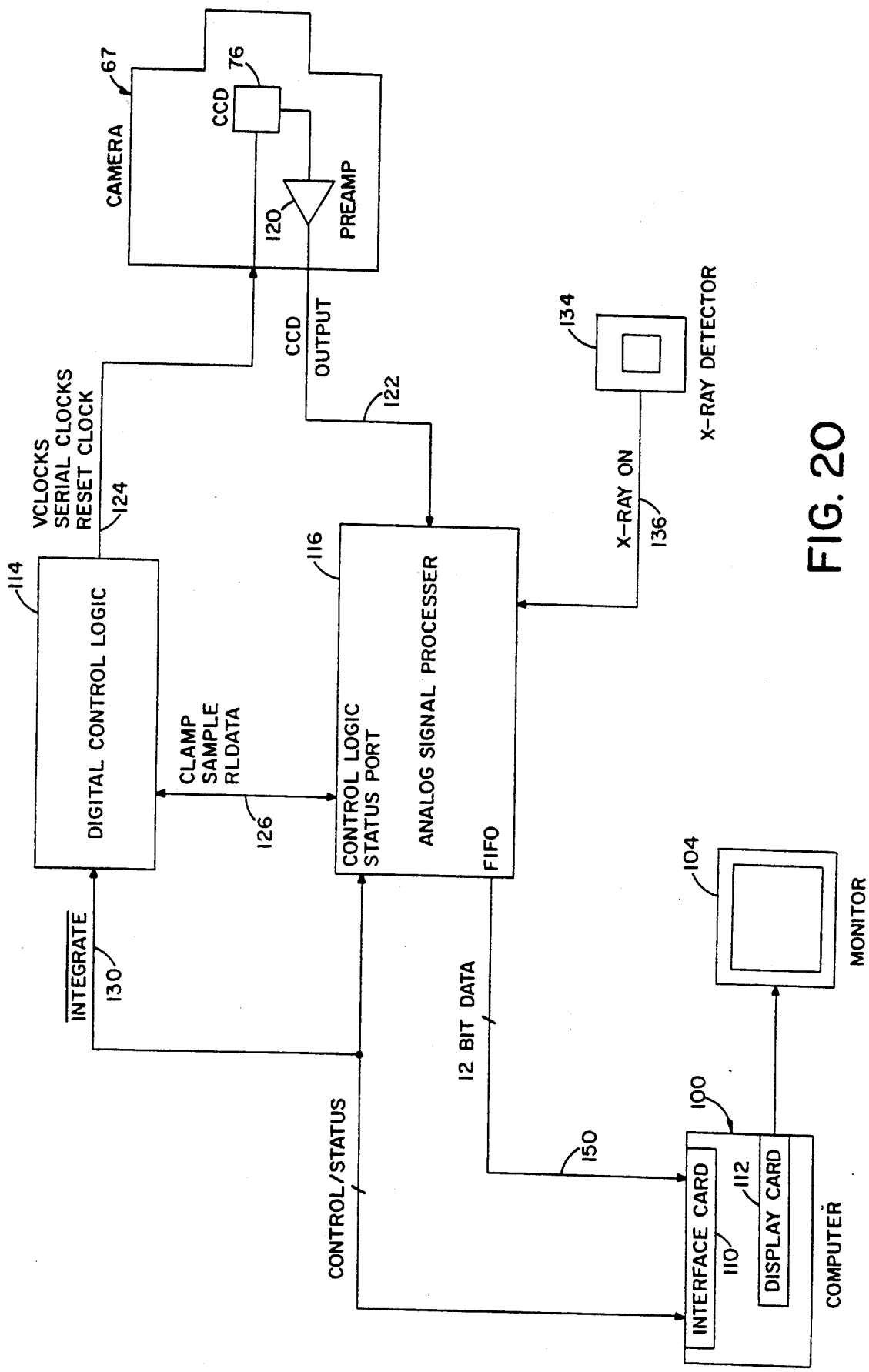
FIG. 20 is an overall block diagram of the system electronics used to convert the digital information from the CCD camera into mammographic display information as presented on the monitor driven by an associated computer.

As best seen in FIGS. 18 and 20, the computer and associated system electronics forming part of the overall digital mammography system comprises computer 100, a control module 102, a module 104 for presentation of mammography information, disc drive 106 and keyboard 108 associated with computer 100. As best seen in FIG. 20, the system electronics include an interface card 110 and a video display card 112 which reside within computer 100.

Details concerning the computer, video card and monitor used in the preferred embodiment of the present invention are presented in Table 1.

TABLE 1

| | |
|---|---|
| Computer 100 | IBM compatible personal computer with an Intel type 80386 ™ or 80486 ™ processor and 12 to 16 Mb RAM, and 200 MB hard disk storage |
| Video display card 112 | Trident Impact 3 ™ video display card with 1024 × 768 pixel resolution and 8 bit luminance resolution per pixel |
| Monitor 104 | Dotronix M2400 ™ 20 inch monochrome monitor with P104 phosphor, set to vertical and horizontal scan rate of video card; analog input. |

A digital control logic module 114 and an analog signal processor 116 form the overall control module 102. The digital control logic module generates various clocking signals for transfer to the camera 67 for use by CCDs 76. The output of the CCDs are applied through a preamplifier 120 so as to generate a CCD output signal on bus a 122 for presentation to the analog signal processor 116.

Figure 21:
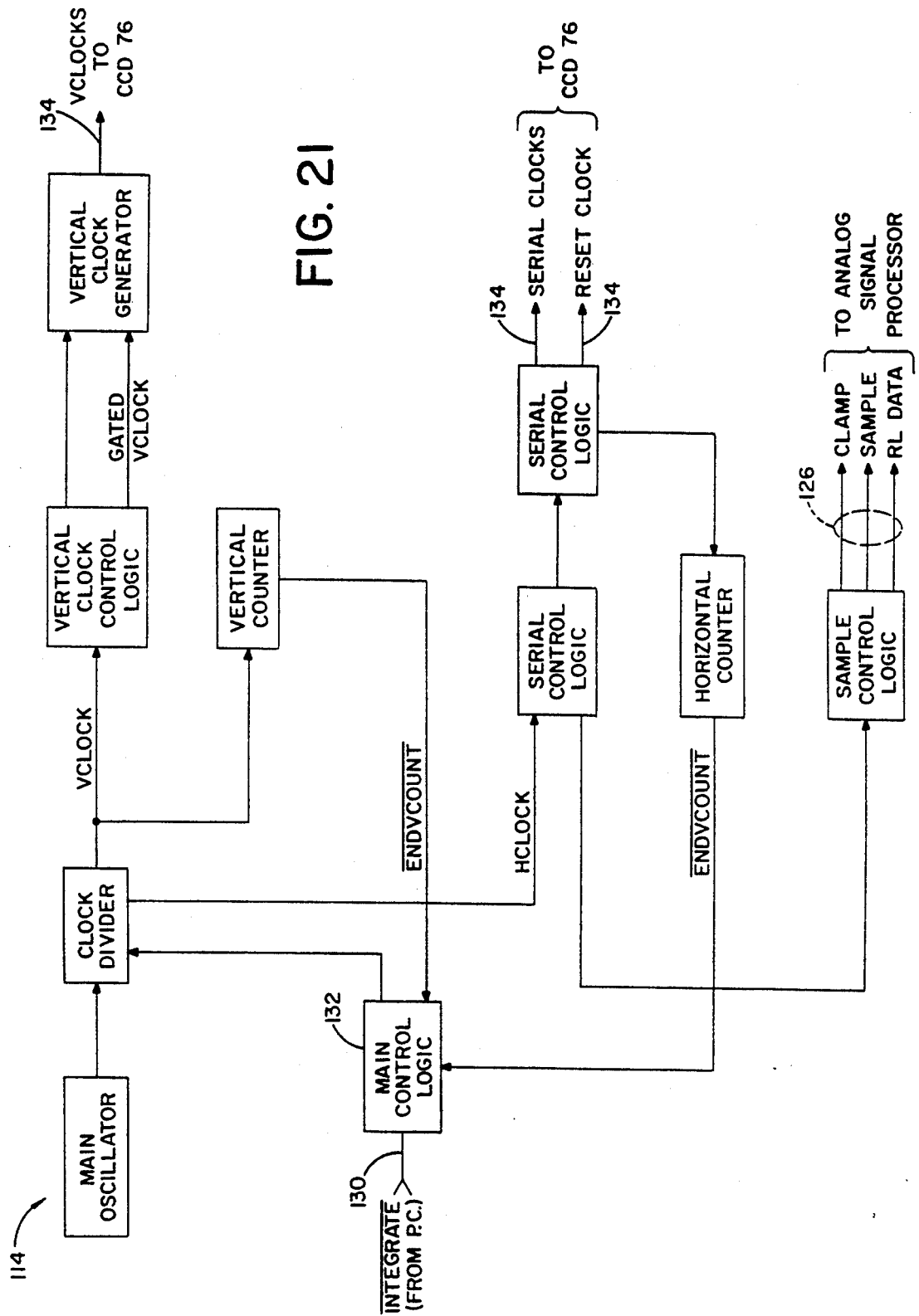
FIG. 21 is a detail block diagram of the digital control logic module shown in FIG. 20.

FIG. 21 is a detailed block diagram of the digital control logic module 114 and illustrates the specific clock signals generated on output bus 124 as well as the clamped sample and data transferred between this module and the analog signal processor module 116 on output bus 126 An integrate control signal from the computer is also shown received on line 130 to the main control logic module 132.

Figure 22:
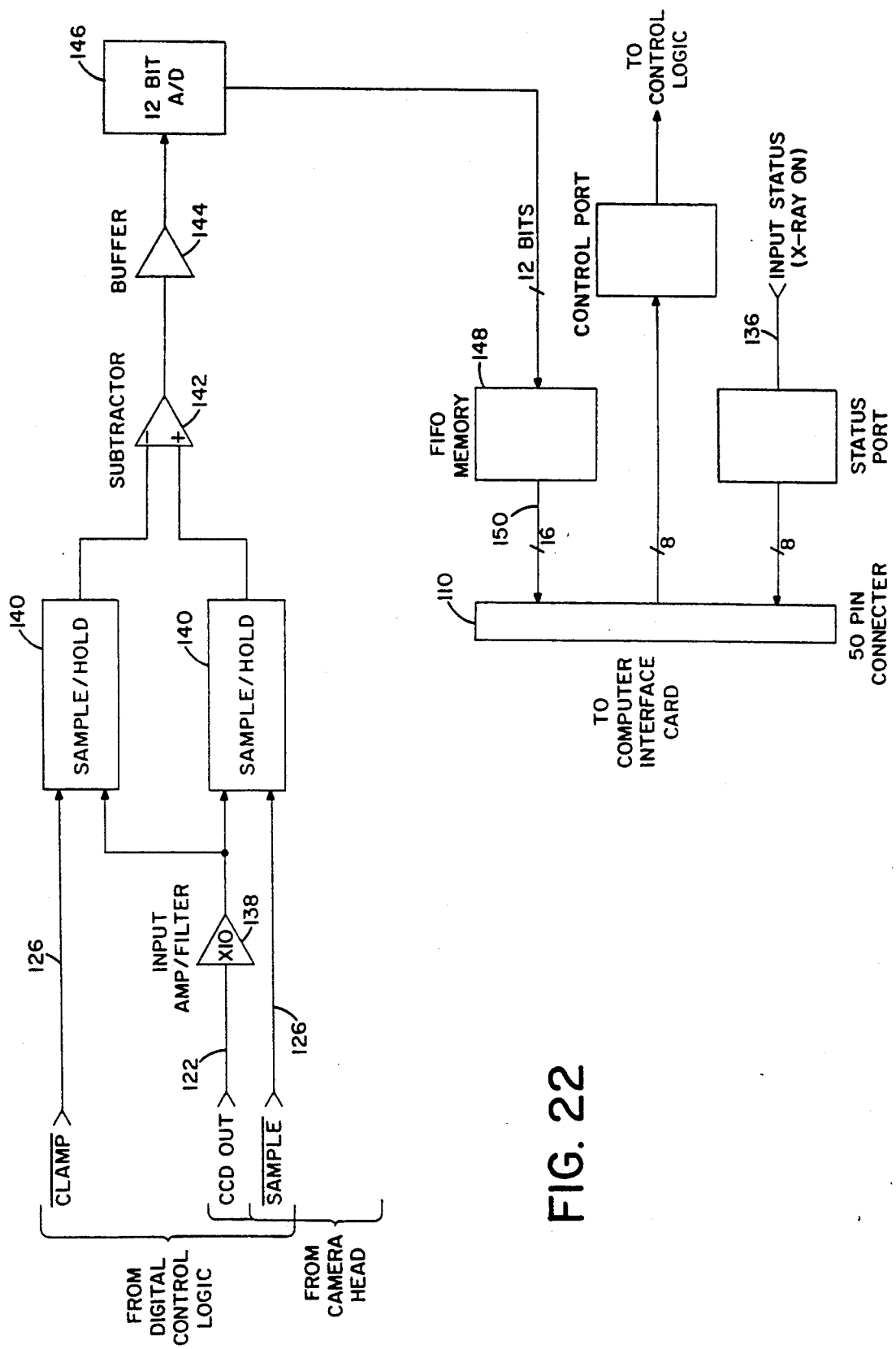
FIG. 22 is a detail block diagram of the analog signal processor module shown in FIG. 20.

Details of the analog signal processor module 116 are shown in the detail block diagram of FIG. 22. As seen in FIGS. 20 and 22 an X-ray status signal indicating the presence of X-rays from X-ray detector 134 is presented on input status line 136.

As can generally be seen in FIG. 22, the CCD output signal received on line 122 is presented to an input amplifier 138 and from there presented under control of the clamp and sample signals to two sample and hold modules 140 and from there to differential amplifier 142 and buffer 144 so as to be presented to a 12 bit analog digital converter 146 so as to present the digital output of the CCD image to a first in first out (FIFO) memory 148. The output of the FIFO memory is connected to the computer interface card 110 for display and image processing by the computer so as to present via display card 112 an output image onto monitor 104. (See FIGS. 18-20).

Figure 23:
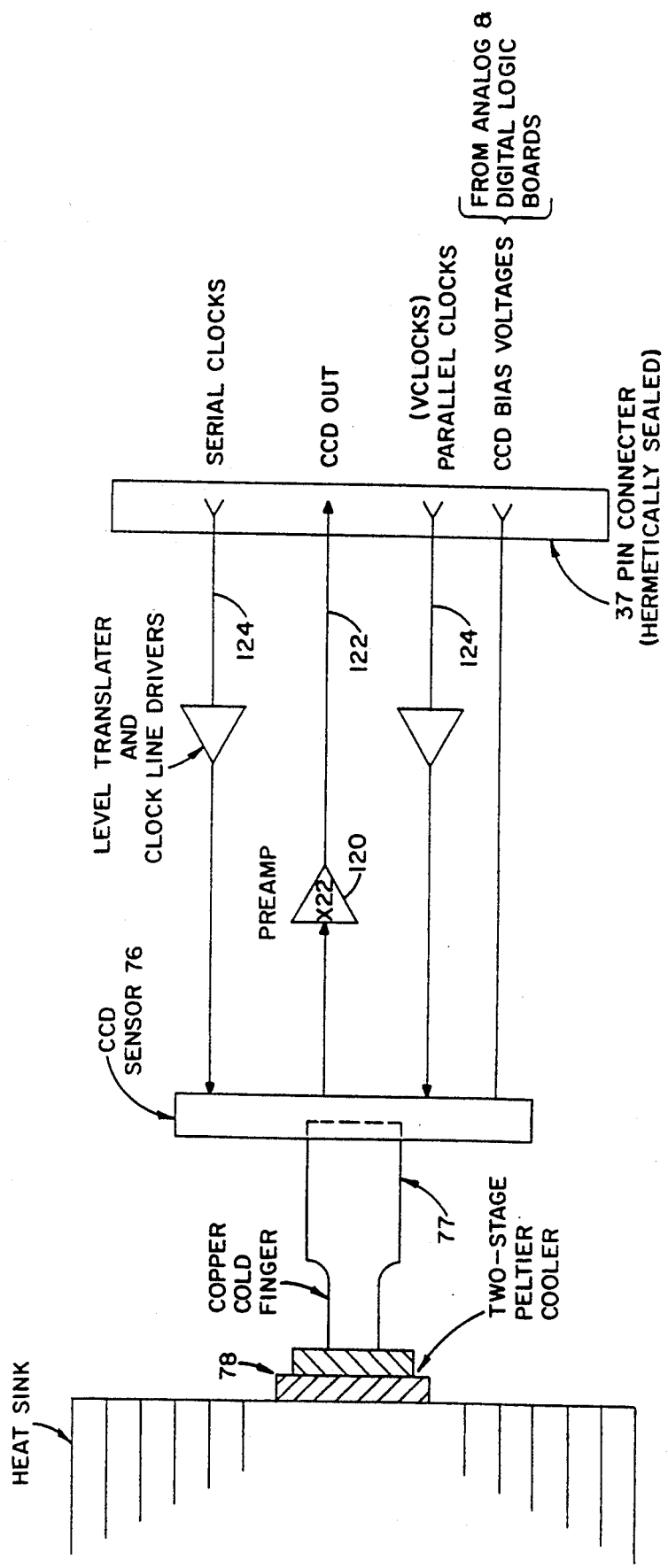
FIG. 23 is an overall diagrammatic view of the CCD camera and its associated electronics.

FIG. 23 is a detailed diagrammatic view of the camera 67 and its associated electronics illustrating the serial clock inputs from the digital control logic module 114 via bus 124; the output of CCD digital data via bus 122; the input of V clocks (parallel clock) information on bus 24; as well as bias voltages from the analog and digital control logic modules 114 and 116.

Digital Image Processing

The overall imaging system shown in FIG. 20 provides an image of the mammographic information on display monitor 104. In order to accomplish this task, the digitized CCD data received on bus 150 from FIFO memory 148 (see FIG. 22) is under the control of computer 100 via execution of a computer program as set forth in a program listing Table 2. As seen in Table 2, the program for achieving mammographic display as well as digital image processing of the mammographic information is written in Microsoft Corporation assembly language as well as Microsoft "C" high level language.

In general, the image presented on monitor 104 comprises 512×512 pixels of mammographic information on a video display of 1024×768 pixels, with each pixel having a luminance resolution of 8 bits or 256 luminance values. The present invention can also support a pixel size display up to 1,024×1,024 pixels. The value of the luminance from the CCD camera has a resolution of 12 bits or 4,096 luminance values. Of course, the 12-bit luminance information from the CCD camera could be displayed with use of a video display card and monitor having such higher luminance imaging capability.

The CCD camera can output data in a 512×512 pixel array or in a 1024×1024 pixel array. If the higher resolution array is used, monitor 104 displays a 1024×768 portion of the CCD data with 128 rows at the top and bottom of the CCD image typically masked; although the viewed image can be scrolled throughout the CCD image.

Overall Operation of Digital Image Processing

The computer program listing set forth in table 1 basically performs the following steps in its display of mammographic information: (1) generates 12 bit luminance information for each pixel in the overall display area via subtracting a dark field and removing fixed pattern noise associated with the particular CCD imaging device, (2) divides the dark field by a white field sometimes referred to as "flat fielding" so as to even out any unevenness in the luminance X-ray information as a result of non-uniform X-ray beam illumination, and (3) produces a luminance histogram of the displayed data.

In addition, the digital image processing of the present invention allows for increasing the contrast which effectively narrows the luminance window as well as providing movement of the luminance window with regard to the luminance range of values for which proportional gray-scaling is implemented; that is to move the window with respect to the CCD luminance values of 0 to 4,095. This function is sometimes referred to as "windowing". More particularly, the contrast displayed on monitor 104 can be increased by reducing the luminance values that are displayed. For example, the luminance values from 1,000 to 1,511 could be displayed out of all luminance values from 0 to 4,095. Then, the 512 different luminance values (1,511−1,000 =512) could be mapped into the 256 brightness values displayable on monitor 104 from white for luminance value equal to 1,000 to black for luminance value equal to 1,511. All luminance values equal to or below 1,000 would be displayed as white and all those equal to or above 1511 would be displayed as black. Of course, the luminance values from the CCD camera could be inversely displayed on the monitor. For the example above, all luminance values equal to or less than 1,000 could be displayed as black, and vice versa for luminance values equal to or greater than 1511. It should also be noted that rapidly inverting the displayed data can help the operator to see features of the image than otherwise possible if only one video polarity is displayable.

Windowing is the ability to slide the range of values to be displayed up or down the luminance 4,096 values from the CCD camera. In the example above, the 512 different luminance values displayable on monitor 104 could be slid down so as, for example, to include pixel luminance values from 70 to 581, or slid upward, to include pixel luminance values from 4,020 to 4,531, for example. This combination of constant control and windowing provide significant diagnostic imaging improvement for the original CCD imaging data received from the camera.

Figure 24:
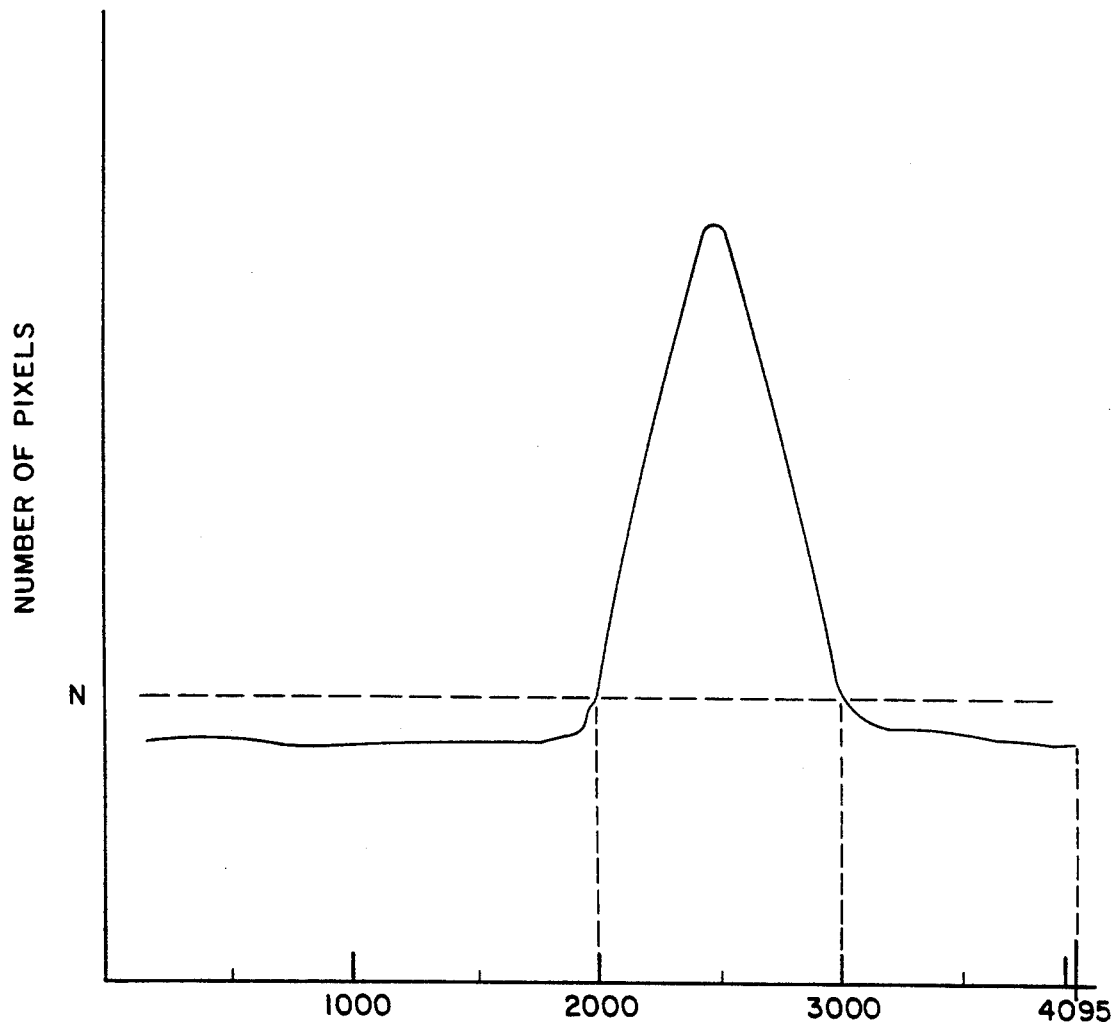
FIG. 24 is a diagram illustrating the number of pixels of an overall typical image which have particular luminance values.

Furthermore, a luminance histogram can be produced by the imaging system. This luminance histogram is then used in a process sometimes referred to as auto-gray scaling. In essence, this process analyzes the CCD imaging data to determine what luminance values are predominantly obtained for a particular image. For example, an image might have most pixels at luminance values in a range of 2,000 to 3,000. Typically, the number of pixels at particular luminance values would have a characteristic bell-shape curve such as shown in FIG. 24. The system then determines that the majority of pixel luminance values predominantly lie between 2,000 and 3,000 and thus would display only those values as gray scale on the monitor. Those pixels with luminance values equal to or less than 2,000 would be displayed as white while pixel values equal to or greater than 3,000 would be displayed as black. The process is therefore similar to selecting the luminance values to be displayed for contrast enhancement.

The present invention also incorporates convolution filtering and edge enhancement which can operate on all or a subset of the displayed image. For convolution filtering a kernel having a matrix size of 3×3 pixels or 5×5 pixels can be used around each pixel for which such convolution filtering is desired.

Furthermore, the implementation uses a lookup table technique for the gray scale associated with the screen luminance and thus provides a luminance to gray scale image mapping as described above.

Additional features also include a high pass filtering so as to sharpen details as well as low pass filtering so as to remove high spatial noise which effectively provides for edge enhancement for rapidly changing data.

Furthermore, the present invention can perform "histogram equalization" and "contrast stretching". Similar to the convolution filtering described above, these functions can operate on all or a subset of the displayed image, sometimes referred to as the region of interest. "Contrast stretching" effectively stretches the grayscale over the region of interest, thereby using the entire available range of displayable grayscale only in this region of interest.

In "histogram equalization", the system remaps the data in the region of interest so that the resulting data has an equal number of occurrences for each histogram bin. In other words, if one looked at the luminance histogram in the region of interest after doing histogram equalization, each bar of the histogram would have the same height rather than the bell shape curve as shown in FIG. 24. Histogram equalization helps to enhance the grayscale rendition for certain image making visualization of abnormalities easier.

Finally, the stereotactic imaging explained above uses cursor marking of the displayed image and is implemented in the program listings forming Table 2. Positioned information in digital form interfaces with the X, Y or Z control knobs on the needleguide stage or carriage 45 (FIGS. 6, 7) actuated manually or servodriven, and a null indication signals matching of calculated with actual coordinates. This interfacing corresponds to the manual calculation of coordinates using a "digitizing pad" with a film grid system like those used with computer pads, to produce the same matching with the actual coordinates of the needle guide stage.

The overall operation of the various program modules are explained via the comments associated with those modules in program listing Table 2. The overall result is not only to present the digitized information but to provide for overall enhancement of the information including zooming of specific regions of interest, edge enhancement, contrast enhancement as well as artifact removal associated with the CCD imaging sensors. In general, the digital image processing provides much greater information to the examining physician than that available using radiographic imaging.

It will thus be seen that the objects set forth above, and those made apparent from the preceding descriptions, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

TABLE 2

```
;****************************************************************\
;FUNCTION:
;    xchg_array(source address, count)
;
;ARGUMENTS:
;    int *source;         Memory address of integer array
;    unsigned int count;  Number of words in array
;
;DESCRIPTION:
;    Inverts a video line left to right, starting at source address.
;****************************************************************/
;
;
     TITLE   Invert video line left to right
     SUBTTL  TONY SCANDURA     08/27/91
     NAME    _BINNING
;
.286c
INCLUDE MEMMODEL.MAC
INCLUDE TRIDENT.ASM
```

```
;
;
    IF   LPROG
X   EQU  6
    ELSE
X   EQU  4
    ENDIF
;
    PSEG
    PUBLIC  _XCHG_ARRAY
    IF   LPROG
_XCHG_ARRAY PROC    FAR
    ELSE
_XCHG_ARRAY PROC    NEAR
    ENDIF
    CLI
    PUSH    BP
    MOV BP,SP
    PUSH    SI
;
;SET UP REGISTERS FOR XCHG
;
    MOV BX,[BP+X]    ;SET UP POINTER TO ARRAY
    MOV SI,[BP+X+2]  ;GET ARRAY LENGTH
    MOV CX,SI        ;COMPUTE NUMBER OF WORDS TO XCHG
    SHR CX,1
    DEC SI           ;COMPUTE ADDRESS OF LAST ELEMENT
    SHL SI,1
    ADD SI,BX
L10:    MOV AX,[SI]  ;GET A WORD
    XCHG    AX,[BX]  ;XCHANGE 1ST & LAST ELEMENT
    MOV [SI],AX
    INC BX           ;INCREMENT POINTER TO ARRAY
    INC BX
    DEC SI           ;DECREMENT POINTER TO ARRAY
    DEC SI
    LOOP    L10
;
    POP SI
    POP BP
    STI
    RET
;
_XCHG_ARRAY ENDP
;**********************************************************\
;FUNCTION:
;   squeeze(source address, count)
;
;ARGUMENTS:
;   int *source;            Memory address of integer array
;   unsigned int count;  Number of words in array
;
;DESCRIPTION:
;   Gets rid of holes in the data stream caused by reading binned.
;**********************************************************/
;
;
;   TITLE   Squeeze video line left
;   SUBTTL  TONY SCANDURA    09/13/91
;   NAME    _SQUEEZE
;
    PUBLIC  _SQUEEZE
    IF   LPROG
_SQUEEZE    PROC    FAR
    ELSE
_SQUEEZE    PROC    NEAR
    ENDIF
    CLI
    PUSH    BP
    MOV BP,SP
    PUSH    SI
    PUSH    DI
;
```

```
;SET UP REGISTERS FOR XCHG
;
    MOV DI,[BP+X]      ;SET UP POINTER TO ARRAY
    MOV CX,[BP+X+2]    ;GET ARRAY LENGTH
    SHR CX,1           ;COMPUTE # OF WORDS TO MOVE
    MOV BX,02H         ;INCREMENT VALUE
    MOV SI,DI          ;COMPUTE ADDRESS OF FIRST REAL ELEMENT
L100:   ADD SI,BX
    LODSW              ;GET A WORD
    STOSW              ;STORE IT IN NEW LOCATION
    LOOP    L100
;
    POP DI
    POP SI
    POP BP

STI
    RET
;
_SQUEEZE    ENDF
    ENDPS
    END
;****************************************************************\
;FUNCTION:
;   inp_to_crt(xpos, ypos, count)   inp a series of bytes to crt
;
;ARGUMENTS:
;   int xpos, ypos; X, Y coordinate of pixel to write
;   unsigned int count; Number of bytes to input
;
;DESCRIPTION:
;   Inputs a series of bytes from an input port to consecutive crt
;   memory locations.  This function handles converting the X, Y
;   coordinate to the linear address space of the Trident memory map.
;
;****************************************************************/
;
;
    TITLE   Input a series of bytes to memory
    SUBTTL  TONY SCANDURA    10/25/90
    NAME    _INTOCRT
;
.286c
INCLUDE MEMMODEL.MAC
INCLUDE TRIDENT.ASM
;
;
    IF  LPROG
X   EQU 6
    ELSE
X   EQU 4
    ENDIF
;
    PSEG
    PUBLIC  _INP_TO_CRT
    IF  LPROG
_INP_TO_CRT PROC    FAR
    ELSE
_INP_TO_CRT PROC    NEAR
    ENDIF
    PUSH    BP
    MOV BP,SP
    PUSH    DI
;
;COMPUTE REAL ADDRESS USING Y * 1024 + X
;COMPUTE SEGMENT PART OF ADDRESS
;
    MOV BX,[BP+X+2]  ;GET Y VALUE
    SHL BX,1         ;Y * 4
    SHL BX,1
    MOV AH,BH        ;GET SEGMENT VALUE
    XOR AH,02H       ;ADJUST PAGE BIT
    MOV AL,0EH       ;MODE CONTROL REGISTER 1
```

```
        MOV DX,SEQAP      ;SEQUENCER ADDRESS PORT
        OUT DX,AX         ;SET TRIDENT SEGMENT REGISTER
;
;COMPUTE OFFSET PART OF ADDRESS
;
        XOR BH,BH         ;GET RID OF SEGMENT BITS
        XCHG    BH,BL     ;Y * 256
        MOV AX,[BP+X]     ;GET X VALUE
        ADD AX,BX         ;ADD IN X OFFSET
;
;UPDATE THE SCREEN
;
        LES DI,DWORD PTR SCR_BASE    ; SET UP POINTER TO SCREEN BASE
        ADD DI,AX         ;POINT TO PIX LOCATION USING ES:DI
        MOV DX,DATA_PORT  ;INPUT PORT TO DX
        MOV CX,[BP+X+4]   ;NUMBER OF BYTES TO INPUT
        REP INSB
        POP DI
        POP BP
        RET
;
_INP_TO_CRT ENDP
        ENDPS
;
        DSEG
SCR_BASE    DD  MBASE_DWORD
        ENDDS
        END
;
;MACRO PARAMETERS FOR TRIDENT VIDEO CARD
;
GCIP            EQU 03CEH
SEQAP           EQU 03C4H
SEQDP           EQU 03C5H
OUT_PORT        EQU 0310H
DATA_PORT       EQU 0310H
DACWRAD         EQU 03C8H
MBASE_SEG       EQU 0A000H
MBASE_DWORD     EQU 0A0000000H
CGEN8X8TBL      EQU 0BB2458CH
CGEN8X16TBL     EQU 0BB25CBAH
BYTESPERLINE    EQU 1024
;********************************************************************
****
;FUNCTION:
;    invert_video(xpos, ypos, xlen, ylen)Invert the video image
;
;
;ARGUMENTS:
;    int xpos, ypos; X, Y coordinate of starting pixel
;    int xlen, ylen; x and y length of block in pixels
;
;DESCRIPTION:
;    This function inverts the video image (black on white to/from
;    white on black) for the specified block of pixels.
;********************************************************************
***
;
;
        TITLE   Invert video image
        SUBTTL  TONY SCANDURA    11/15/90
        NAME    _INVIDEO
;
.286c
INCLUDE MEMMODEL.MAC
INCLUDE TRIDENT.ASM
;
;
        IF  LPROG
X       EQU 6
        ELSE
X       EQU 4
        ENDIF
```

```
;
XPOS    EQU [BP+X]
YPOS    EQU [BP+X+2]
XLEN    EQU [BP+X+4]
YLEN    EQU [BP+X+6]
;
    PSEG
    PUBLIC  _INVERT_VIDEO
    IF  LPROG
_INVERT_VIDEO   PROC    FAR
    ELSE
_INVERT_VIDEO   PROC    NEAR
    ENDIF
    PUSH    BP
    MOV BP,SP
    PUSH    SI
    PUSH    DI
    PUSH    DS
;
;COMPUTE REAL ADDRESS USING Y * 1024 + X
;COMPUTE SEGMENT PART OF ADDRESS
;
    MOV BX,YPOS     ;GET Y VALUE

SHL BX,1        ;Y * 4
    SHL BX,1
    MOV AH,BH       ;GET SEGMENT VALUE
    XOR AH,02H      ;ADJUST PAGE BIT
    MOV AL,0EH      ;MODE CONTROL REGISTER 1
    MOV DX,SEQAP    ;SEQUENCER ADDRESS PORT
    OUT DX,AX       ;SET TRIDENT SEGMENT REGISTER
;
;COMPUTE OFFSET PART OF ADDRESS
;
    XOR BH,BH       ;GET RID OF SEGMENT BITS
    XCHG    BH,BL   ;Y * 256
    MOV AX,XPOS     ;GET X VALUE
    ADD AX,BX       ;ADD IN X OFFSET
    LES DI,DWORD PTR SCR_BASE   ; SET UP POINTER TO SCREEN BASE
    ADD DI,AX       ;POINT TO PIX LOCATION USING ES:DI
    LDS SI,DWORD PTR SCR_BASE   ; SET UP POINTER TO SCREEN BASE
    ADD SI,AX       ;POINT TO PIX LOCATION USING DS:SI
;
;UPDATE THE SCREEN
;
    MOV BX,BYTESPERLINE ;COMPUTE INCREMENT FROM END OF
    SUB BX,XLEN     ;LINE TO BEGINING OF NEXT LINE
    MOV CX,YLEN     ;NUMBER OF ROWS IN LINE
L10:    PUSH    CX      ;SAVE COUNTER FOR NUMBER OF REMAINING ROWS
    MOV CX,XLEN     ;COUNTER FOR WIDTH OF BLOCK
L20:    LODSB           ;GET A PIXEL
    NOT AL      ;INVERT THE BITS
    STOSB           ;UPDATE ONE PIXEL ON CRT
    LOOP    L20     ;LOOP 'TIL LINE DONE
    ADD DI,BX       ;INCREMENT POINTER TO NEXT ROW OF PIXELS
    ADD SI,BX       ;INCREMENT POINTER TO NEXT ROW OF PIXELS
    JA  L30     ;IF CARRY, OR 0, NEED TO UPDATE SEGMENT
    CALL    CHKBANK     ;UPDATE SEGMENT REGISTER
L30:    POP CX
    LOOP    L10     ;LOOP DOWN THE ROWS
;
DONE:   POP DS
    POP DI
    POP SI
    POP BP
    RET
;
_INVERT_VIDEO   ENDP
;
;SUBROUTINE TO UPDATE THE SEGMENT REGISTER
;
    IF  LPROG
CHKBANK PROC    FAR
    ELSE
```

```
CHKBANK PROC    NEAR
    ENDIF
    MOV DX,SEQAP    ;SEQUENCER ADDRESS PORT
    MOV AL,0EH      ;MODE CONTROL REGISTER 1
    OUT DX,AL
    INC DX          ;SEQUENCER DATA PORT
    IN  AL,DX       ;GET OLD BANK
    INC AL          ;INCREMENT THE BANK
    XOR AL,02       ;INVERT PAGE BIT
    OUT DX,AL
    RET
;
CHKBANK ENDP
    ENDPS
;
    DSEG
SCR_BASE    DD  MBASE_DWORD
    ENDDS
    END
;******************************************************************
******\
;FUNCTION:
;   inpw_to_mem(address, port, count); Input a series of words to memory
;
;ARGUMENTS:
;   char far *address;  Memory address of starting pixel to write
;   int port;           Port to input from
;   unsigned int count; Number of bytes to input
;
;DESCRIPTION:
;   Inputs a series of words from an input port to consecutive
;   memory locations starting at address.
;******************************************************************
******/
;
;
    TITLE   Input a series of words to memory
    SUBTTL  TONY SCANDURA    11/06/90
    NAME    _INWTMEM
;
.286c
INCLUDE MEMMODEL.MAC
INCLUDE TRIDENT.ASM
;
;
    IF  LPROG
X   EQU 6
    ELSE
X   EQU 4
    ENDIF
;
    PSEG
    PUBLIC  _INPW_TO_MEM
    IF  LPROG
_INPW_TO_MEM    PROC    FAR
    ELSE
_INPW_TO_MEM    PROC    NEAR
    ENDIF
    CLI
    PUSH    BP
    MOV BP,SP
    PUSH    DI
;
;SET UP REGISTERS FOR REP INSB
;
    LES DI,[BP+X]   ;SET UP POINTER TO DESTINATION
    MOV DX,[BP+X+4] ;INPUT PORT TO DX
    MOV CX,[BP+X+6] ;NUMBER OF WORDS TO INPUT
    REP INSW
;
    POP DI
    POP BP
```

```
        STI
        RET
;
_INPW_TO_MEM    ENDP
        ENDPS
        END
;*****************************************************************
******\
;FUNCTION:
;    load_grayscale(address); Load the video DAC LUTs
;
;ARGUMENTS:
;    char far *address;  Memory address of table of R, G, B values
;
;DESCRIPTION:
;    Load the video DAC lookup tables from table pointed to by address
;*****************************************************************
******/
;
;
        TITLE   Load LUTs
        SUBTTL  TONY SCANDURA   11/05/90
        NAME    _LOADGRY
.286c
INCLUDE MEMMODEL.MAC
INCLUDE TRIDENT.ASM
;
;
        IF  LPROG
X       EQU 6
        ELSE
X       EQU 4
        ENDIF
;
TABLE   EQU [BP+X]
;
        PSEG
        PUBLIC  _LOAD_GRAYSCALE
        IF  LPROG
_LOAD_GRAYSCALE PROC    FAR
        ELSE
_LOAD_GRAYSCALE PROC    NEAR
        ENDIF
        CLI
        PUSH    BP
        MOV BP,SP
        PUSH    SI
        PUSH    DS
;
;SET UP REGISTERS FOR REP OUTSB
;
        LDS SI,TABLE      ;SET UP POINTER TO TABLE OF VALUES
        MOV DX,DACWRAD    ;OUTUT PORT FOR DAC WRITE ADDRESS
        MOV CX,768        ;NUMBER OF BYTES TO OUTPUT
        XOR AL,AL         ;LOAD STARTING ADDRESS
        OUT DX,AL
        INC DX            ;PORT FOR DAC LUT DATA
        REP OUTSB
;
        POP DS
        POP SI
        POP BP
        STI
        RET
;
_LOAD_GRAYSCALE ENDP
        ENDPS
        END
;****************************************************************\
;FUNCTION:
;    mem_to_mem(source address, dest address, count)
;
;ARGUMENTS:
```

```
;   char far *source, *dest; Memory addresses of source and destination
;   unsigned int count;   Number of bytes to move
;
;DESCRIPTION:
;   Moves a series of bytes from consecutive memory locations
;   starting at source address to dest address.
;*****************************************************************/
;
;
    TITLE   Move a series of bytes from memory to memory
    SUBTTL  TONY SCANDURA    03/01/90
    NAME    _MEMTMEM
;
.286c
INCLUDE MEMMODEL.MAC
INCLUDE TRIDENT.ASM
;
;
    IF  LPROG
X   EQU 6
    ELSE
X   EQU 4
    ENDIF
;
    PSEG
    PUBLIC  _MEM_TO_MEM
    IF  LPROG
_MEM_TO_MEM PROC    .FAR
    ELSE
_MEM_TO_MEM PROC    NEAR
    ENDIF
    CLI
    PUSH    BP
    MOV BP,SP
    PUSH    DI
    PUSH    SI
    PUSH    DS
;
;SET UP REGISTERS FOR REP MOVSB
;
    CLD
    LDS SI,[BP+X]    ;SET UP POINTER TO SOURCE
    LES DI,[BP+X+4]  ;SET UP POINTER TO DESTINATION
    MOV CX,[BP+X+8]  ;NUMBER OF BYTES TO INPUT
    REP MOVSB
;
    POP DS
    POP SI
    POP DI
    POP BP
    STI
    RET
;
_MEM_TO_MEM ENDP
    ENDPS
    END
;*****************************************************************\
;FUNCTION:
;   print_8x8(char, xpos, ypos, fgd, bkgd)   Display a character
;                       In Graphics Mode
;
;ARGUMENTS:
;   char *char; Pointer to character string to print
;   int xpos, ypos; X, Y coordinate of pixel to write
;   int fgd, bkgd;  foreground and background pixel values
;
;DESCRIPTION:
;   This function is a complete software character generator.
;   It writes a single character to the specified X, Y coordinate.
;   Both the foreground and background pixel values must be given.
;*****************************************************************/
;
;
```

```
        TITLE   Display character using X,Y coordinates
        SUBTTL  TONY SCANDURA   10/25/90
        NAME    _PR_8X8
;
.286c
INCLUDE MEMMODEL.MAC
INCLUDE TRIDENT.ASM
;
;
        IF  LPROG
X       EQU 6
        ELSE
X       EQU 4
        ENDIF
;
CHAR    EQU [BP+X]
XPOS    EQU [BP+X+2]
YPOS    EQU [BP+X+4]
FGD EQU [BP+X+6]
BKGD    EQU [BP+X+8]
;
BYTESPERLINE    EQU 1024
CHAR_WIDTH  EQU 8
CHAR_HEIGHT8    EQU 8
INCREMENT   EQU BYTESPERLINE-CHAR_WIDTH
NEXT_CHAR8  EQU BYTESPERLINE*CHAR_HEIGHT8-CHAR_WIDTH
;
        PSEG
        PUBLIC  _PRINT_8X8
        IF  LPROG
_PRINT_8X8  PROC    FAR
        ELSE
_PRINT_8X8  PROC    NEAR
        ENDIF
        PUSH    BP
        MOV BP,SP
        PUSH    SI
        PUSH    DI
;
;COMPUTE REAL ADDRESS USING Y * 1024 + X
;COMPUTE SEGMENT PART OF ADDRESS
;
    MOV BX,YPOS         ;GET Y VALUE
    SHL BX,1            ;Y * 4
    SHL BX,1
    MOV AH,BH           ;GET SEGMENT VALUE
    XOR AH,02H          ;ADJUST PAGE BIT
    MOV AL,0EH          ;MODE CONTROL REGISTER 1
    MOV DX,SEQAP        ;SEQUENCER ADDRESS PORT
    OUT DX,AX           ;SET TRIDENT SEGMENT REGISTER
;
;COMPUTE OFFSET PART OF ADDRESS
;
    XOR BH,BH           ;GET RID OF SEGMENT BITS
    XCHG    BH,BL       ;Y * 256
    MOV AX,XPOS         ;GET X VALUE
    ADD AX,BX           ;ADD IN X OFFSET
    LES DI,DWORD PTR SCR_BASE   ;SET UP POINTER TO SCREEN BASE
    ADD DI,AX           ;POINT TO PIX LOCATION USING ES:DI
;
;SET UP CHARACTER DEFINITION TABLE ADDRESSING
;
    MOV BX,CHAR         ;GET POINTER TO CHARACTER
NX_CHR: MOV AL,[BX]     ;THEN MULTIPLY BY NUMBER OF
    XOR AH,AH
    SHL AX,3            ;POINTS TO GET OFFSET INTO TABLE
    JZ  DONE            ;DONE IF CHARACTER WAS ZERO
    PUSH    DS          ;SAVE DATA SEGMENT POINTER TO SOURCE
    LDS SI,DWORD PTR CHAR_ADR8  ;START OF CHARACTER DEF TABLE
    ADD SI,AX           ;DS:SI POINTS TO ADDRESS OF CHAR DEF
```

;
;UPDATE THE SCREEN
;
    MOV CX,CHAR_HEIGHT8 ;NUMBER OF ROWS IN CHARACTER
    MOV DH,FGD      ;GET FOREGROUND PIXEL VALUE
    MOV DL,BKGD     ;GET BACKGROUND PIXEL VALUE
L10:    PUSH    CX      ;SAVE COUNTER FOR NUMBER OF REMAINING ROWS
    MOV CX,CHAR_WIDTH   ;COUNTER FOR CHARACTER WIDTH
    LODSB
    MOV AH,AL       ;PUT CHARACTER CODE IN AH
L11:    MOV AL,DH       ;AL = FOREGROUND PIXEL VALUE
    SHL AH,1        ;TEST EACH BIT IN AH
    JC  L12         ;JUMP IF FOREGROUND PIXEL ELSE
    MOV AL,DL       ;LOAD BACKGROUND PIXEL VALUE
L12:    STOSB           ;UPDATE ONE PIXEL ON CRT
    LOOP    L11
    ADD DI,INCREMENT    ;INCREMENT BUFFER TO NEXT ROW OF PIXELS
    MOV AH,1        ;VALUE TO ADD TO SEGMENT IF NEEDED

CALL    CHKBANK     ;UPDATE SEGMENT IF NEEDED
    POP CX
    LOOP    L10     ;LOOP DOWN THE CHARACTER
;
    INC BX          ;INCREMENT POINTER TO CHAR STRING
    SUB DI,NEXT_CHAR8   ;COMPUTE NEXT SCREEN ADDRESS
    MOV AH,-1       ;VALUE TO ADD TO SEGMENT IF NEEDED
    CALL    CHKBANK     ;UPDATE SEGMENT IF NEEDED
    POP DS          ;GET DATA SEGMENT POINTER TO SOURCE
    JMP SHORT NX_CHR    ;LOOP 'TIL ENTIRE STRING IS PROCESSED
;
DONE:   POP DI
    POP SI
    POP BP
    RET
;
_PRINT_8X8  ENDP
;****************************************************************\
;FUNCTION:
;   print_8x16(char, xpos, ypos, fgd, bkgd) Display a character
;                   In Graphics Mode
;
;ARGUMENTS:
;   char *char; Pointer to character string to print
;   int xpos, ypos; X, Y coordinate of pixel to write
;   int fgd, bkgd;  foreground and background pixel values
;
;DESCRIPTION:
;   This function is a complete software character generator.
;   It writes a single character to the specified X, Y coordinate.
;   Both the foreground and background pixel values must be given.
;****************************************************************/
;
;
;   TITLE   Display  character using X,Y coordinates
;   SUBTTL  TONY SCANDURA   10/23/90
;   NAME    _PR_8X16
;
CHAR_HEIGHT6    EQU 16
NEXT_CHAR6  EQU BYTESPERLINE*CHAR_HEIGHT6-CHAR_WIDTH
;
    PUBLIC  _PRINT_8X16
    IF  LPROG
_PRINT_8X16 PROC    FAR
    ELSE
_PRINT_8X16 PROC    NEAR
    ENDIF
    PUSH    BP
    MOV BP,SP
    PUSH    SI
    PUSH    DI

```
;
;COMPUTE REAL ADDRESS USING Y * 1024 + X
;COMPUTE SEGMENT PART OF ADDRESS
;
    MOV BX,YPOS      ;GET Y VALUE
    SHL BX,1         ;Y * 4
    SHL BX,1
    MOV AH,BH        ;GET SEGMENT VALUE
    XOR AH,02H       ;ADJUST PAGE BIT
    MOV AL,0EH       ;MODE CONTROL REGISTER 1
    MOV DX,SEQAP     ;SEQUENCER ADDRESS PORT
    OUT DX,AX        ;SET TRIDENT SEGMENT REGISTER
;
;COMPUTE OFFSET PART OF ADDRESS
;
    XOR BH,BH        ;GET RID OF SEGMENT BITS
    XCHG    BH,BL    ;Y * 256
    MOV AX,XPOS      ;GET X VALUE
    ADD AX,BX        ;ADD IN X OFFSET
    LES DI,DWORD PTR SCR_BASE   ; SET UP POINTER TO SCREEN BASE
    ADD DI,AX        ;POINT TO PIX LOCATION USING ES:DI
;
;SET UP CHARACTER DEFINITION TABLE ADDRESSING
;
    MOV BX,CHAR          ;GET POINTER TO CHARACTER
NXXCHR: MOV AL,[BX]      ;THEN MULTIPLY BY NUMBER OF
    XOR AH,AH
    SHL AX,4         ;POINTS TO GET OFFSET INTO TABLE
    JZ  DONE1        ;DONE IF CHARACTER WAS ZERO
    PUSH    DS       ;SAVE DATA SEGMENT POINTER TO SOURCE
    LDS SI,DWORD PTR CHAR_ADR6   ;START OF CHARACTER DEF TABLE
    ADD SI,AX        ;DS:SI POINTS TO ADDRESS OF CHAR DEF

;
;UPDATE THE SCREEN
;
    MOV CX,CHAR_HEIGHT6 ;NUMBER OF ROWS IN CHARACTER
    MOV DH,FGD       ;GET FOREGROUND PIXEL VALUE
    MOV DL,BKGD      ;GET BACKGROUND PIXEL VALUE
L100:   PUSH    CX   ;SAVE COUNTER FOR NUMBER OF REMAINING ROWS
    MOV CX,CHAR_WIDTH    ;COUNTER FOR CHARACTER WIDTH
    LODSB
    MOV AH,AL        ;PUT CHARACTER CODE IN AH
L110:   MOV AL,DH    ;AL = FOREGROUND PIXEL VALUE
    SHL AH,1         ;TEST EACH BIT IN AH
    JC  L120         ;JUMP IF FOREGROUND PIXEL ELSE
    MOV AL,DL        ;LOAD BACKGROUND PIXEL VALUE
L120:   STOSB        ;UPDATE ONE PIXEL ON CRT
    LOOP    L110
    ADD DI,INCREMENT     ;INCREMENT BUFFER TO NEXT ROW OF PIXELS
    MOV AH,1         ;VALUE TO ADD TO SEGMENT IF NEEDED
    CALL    CHKBANK  ;UPDATE SEGMENT IF NEEDED
    POP CX
    LOOP    L100     ;LOOP DOWN THE CHARACTER
;
    INC BX       ;INCREMENT POINTER TO CHAR STRING
    SUB DI,NEXT_CHAR6    ;COMPUTE NEXT SCREEN ADDRESS
    MOV AH,-1        ;VALUE TO ADD TO SEGMENT IF NEEDED
    CALL    CHKBANK  ;UPDATE SEGMENT IF NEEDED
    POP DS       ;GET DATA SEGMENT POINTER TO SOURCE
    JMP SHORT NXXCHR     ;LOOP 'TIL ENTIRE STRING IS PROCESSED
;
DONE1:  POP DI
    POP SI
    POP BP
    RET
;
_PRINT_8X16 ENDP
;
;SUBROUTINE TO UPDATE THE SEGMENT REGISTER
;
```

```
        IF  LPROG
CHKBANK PROC    FAR
        ELSE
CHKBANK PROC    NEAR
        ENDIF
        JC  NEWBNK      ;IF CARRY, NEED TO UPDATE SEGMENT
        RET
NEWBNK: PUSH    DX
        MOV DX,SEQAP    ;SEQUENCER ADDRESS PORT
        MOV AL,0EH      ;MODE CONTROL REGISTER 1
        OUT DX,AL
        INC DX          ;SEQUENCER DATA PORT
        IN  AL,DX       ;GET OLD BANK
        ADD AL,AH       ;INCREMENT OR DECREMENT THE BANK
        XOR AL,02       ;INVERT PAGE BIT
        OUT DX,AL
        POP DX
        RET
;
CHKBANK ENDP
;****************************************************************\
;FUNCTION:
;   set_char_adr();     set character pointers to
;                   character definition tables
;
;ARGUMENTS:
;   None
;
;DESCRIPTION:
;   This function sets far character pointers to the
;   character definition tables for 8x8 and 8x16 characters.
;   This function only needs to be called once.
;****************************************************************/
;
;
        PUBLIC  _SET_CHAR_ADR
        IF  LPROG
_SET_CHAR_ADR   PROC    FAR
        ELSE
_SET_CHAR_ADR   PROC    NEAR
        ENDIF

PUSH    BP
        MOV BP,SP

MOV AX,1130H    ;SET UP FOR VIDEO BIOS INTERRUPT
        MOV BH,3        ;LOAD TABLE NUMBER FOR 8x8 CHARACTERS
        INT 10H
        MOV WORD PTR CHAR_ADR8+2,ES ;SAVE DD POINTER IN CHAR_ADR8
        MOV WORD PTR CHAR_ADR8,BP   ;BP = OFFSET, ES = SEGMENT

MOV AX,1130H    ;SET UP FOR VIDEO BIOS INTERRUPT
        MOV BH,6        ;LOAD TABLE NUMBER FOR 8x16 CHARACTERS
        INT 10H
        MOV WORD PTR CHAR_ADR6+2,ES ;SAVE DD POINTER IN CHAR_ADR6
        MOV WORD PTR CHAR_ADR6,BP   ;BP = OFFSET, ES = SEGMENT

POP BP
        RET

_SET_CHAR_ADR   ENDP
        ENDPS
;
        DSEG
CHAR_ADR8   DD  ?
CHAR_ADR6   DD  ?
SCR_BASE    DD  MBASE_DWORD
        ENDDS
        END
;****************************************************************\
```

```
;FUNCTION:
;   rec_window(source address, dest address, width, height)
;
;ARGUMENTS:
;   char far *source, far *dest;  Memory addr of source and destination
;   int width, height;            Width and height of rectangle
;
;DESCRIPTION:
;   Recalls a window from a memory buffer to the CRT.
;****************************************************************/
;
;
    TITLE   Recalls a window.
    SUBTTL  TONY SCANDURA    11/02/90
    NAME    _REC_WIN
;
.286c
INCLUDE MEMMODEL.MAC
INCLUDE TRIDENT.ASM
;
;
    IF  LPROG
X   EQU 6
    ELSE
X   EQU 4
    ENDIF
;
SOURCE  EQU [BP+X]
DEST    EQU [BP+X+4]
XLEN    EQU [BP+X+8]
YLEN    EQU [BP+X+10]
;
    PSEG
    PUBLIC  _REC_WINDOW
    IF  LPROG
_REC_WINDOW PROC    FAR
    ELSE
_REC_WINDOW PROC    NEAR
    ENDIF
;
    CLI
    PUSH    BP
    MOV BP,SP
    PUSH    DI
    PUSH    SI
    PUSH    DS
;
    CLD
    LDS SI,SOURCE    ;SET UP POINTER TO SOURCE
    LES DI,DEST      ;SET UP POINTER TO DESTINATION
    MOV CX,YLEN      ;NUMBER OF BYTES IN HEIGHT (Y)
    MOV AX,BYTESPERLINE ;COMPUTE INCREMENT VALUE FROM END OF ONE
    SUB AX,XLEN      ;LINE TO BEGINNING OF NEXT LINE - SAVE IN AX
L10:    MOV BX,CX        ;SAVE COUNTER FOR NUMBER OF ROWS REMAINING
    MOV CX,XLEN      ;NUMBER OF BYTES IN WIDTH (X)
    REP MOVSB
    OR  DI,DI        ;IF ZERO, NEED TO UPDATE SEGMENT
    JNZ L15
    CALL    INCBANK
L15:    ADD DI,AX        ;DESTINATION POINTS TO ADDRESS OF NEXT LINE
    JNC L20      ;IF CARRY, NEED TO UPDATE SEGMENT
    CALL    INCBANK      ;UPDATE SEGMENT REGISTER
L20:    MOV CX,BX        ;GET LOOP COUNTER
    LOOP    L10      ;LOOP TIL ALL ROWS DONE
;
    POP DS
    POP SI
    POP DI
    POP BP
    STI
    RET
```

```
;
_REC_WINDOW ENDP
;
;SUBROUTINE TO UPDATE THE SEGMENT REGISTER
;
    IF  LPROG
INCBANK PROC    FAR
    ELSE
INCBANK PROC    NEAR
    ENDIF
    PUSH    AX
    MOV DX,SEQAP    ;SEQUENCER ADDRESS PORT
    MOV AL,0EH      ;MODE CONTROL REGISTER 1
    OUT DX,AL
    INC DX          ;SEQUENCER DATA PORT
    IN  AL,DX       ;GET OLD BANK
    INC AL          ;INCREMENT THE BANK
    XOR AL,02       ;INVERT PAGE BIT
    OUT DX,AL
    POP AX
    RET
;
INCBANK ENDP
    ENDPS
    END
;****************************************************************
****
;FUNCTION:
;   rev_fgd_bkgd(xpos, ypos, fgd, bkgd, xlen, ylen)
;                   Reverse forground and background
;                   pixel block in Graphics Mode
;
;ARGUMENTS:
;   int xpos, ypos; X, Y coordinate of starting pixel
;   int fgd, bkgd;  foreground and background pixel values to swap
;   int xlen, ylen; x and y length of block in pixels
;
;DESCRIPTION:
;   This function swaps the foreground and background
;   pixel values for the specified block of pixels.
;****************************************************************
***
;
;
    TITLE   Reverse foreground and background block of pixels
    SUBTTL  TONY SCANDURA   12/2/90
    NAME    _REVFGBK
;
.286c
INCLUDE MEMMODEL.MAC
INCLUDE TRIDENT.ASM
;
;
    IF  LPROG
X   EQU 6
    ELSE
X   EQU 4
    ENDIF
;
XPOS    EQU [BP+X]
YPOS    EQU [BP+X+2]
FGD EQU [BP+X+4]
BKGD    EQU [BP+X+6]
XLEN    EQU [BP+X+8]
YLEN    EQU [BP+X+10]
;
    PSEG
    PUBLIC  _REV_FGD_BKGD
    IF  LPROG
_REV_FGD_BKGD   PROC    FAR
    ELSE
```

```
_REV_FGD_BKGD    PROC    NEAR
    ENDIF
    PUSH    BP
    MOV BP,SP
    PUSH    SI
    PUSH    DI
;
;COMPUTE REAL ADDRESS USING Y * 1024 + X
;COMPUTE SEGMENT PART OF ADDRESS
;
    MOV BX,YPOS     ;GET Y VALUE
    SHL BX,1        ;Y * 4
    SHL BX,1
    MOV AH,BH       ;GET SEGMENT VALUE
    XOR AH,02H      ;ADJUST PAGE BIT
    MOV AL,0EH      ;MODE CONTROL REGISTER 1
    MOV DX,SEQAP    ;SEQUENCER ADDRESS PORT
    OUT DX,AX       ;SET TRIDENT SEGMENT REGISTER
;
;COMPUTE OFFSET PART OF ADDRESS
;
    XOR BH,BH       ;GET RID OF SEGMENT BITS
    XCHG    BH,BL   ;Y * 256
    MOV AX,XPOS     ;GET X VALUE
    ADD AX,BX       ;ADD IN X OFFSET
    LES DI,DWORD PTR SCR_BASE   ; SET UP POINTER TO SCREEN BASE
    ADD DI,AX       ;POINT TO PIX LOCATION USING ES:DI
;
;UPDATE THE SCREEN
;
    MOV BX,BYTESPERLINE ;COMPUTE INCREMENT FROM END OF
    SUB BX,XLEN     ;LINE TO BEGINING OF NEXT LINE
    MOV CX,YLEN     ;NUMBER OF ROWS IN CHARACTER
    MOV DH,FGD      ;GET FOREGROUND PIXEL VALUE
    MOV DL,BKGD     ;GET BACKGROUND PIXEL VALUE
L10:    PUSH    CX      ;SAVE COUNTER FOR NUMBER OF REMAINING ROWS
    MOV CX,XLEN     ;COUNTER FOR WIDTH OF BLOCK
L20:    MOV AL,DH       ;AL = FOREGROUND PIXEL VALUE
    SCASB
    JNE L30         ;JUMP IF ES:DI NOT FOREGROUND VALUE
    MOV AL,DL       ;OTHERWISE LOAD BACKGROUND PIXEL VALUE
L30:    DEC DI          ;ADJUST DESTINATION ADDRESS
    STOSB           ;UPDATE ONE PIXEL ON CRT
    LOOP    L20     ;LOOP 'TIL LINE DONE
    ADD DI,BX       ;INCREMENT POINTER TO NEXT ROW OF PIXELS
    JNC L40         ;IF CARRY, NEED TO UPDATE SEGMENT
    CALL    CHKBANK ;UPDATE SEGMENT REGISTER
L40:    POP CX
    LOOP    L10     ;LOOP DOWN THE ROWS
;
DONE:   POP DI
    POP SI
    POP BP
    RET
;
_REV_FGD_BKGD   ENDP
;
;SUBROUTINE TO UPDATE THE SEGMENT REGISTER
;
    IF  LPROG
CHKBANK PROC    FAR
    ELSE
CHKBANK PROC    NEAR
    ENDIF
    PUSH    DX
    MOV DX,SEQAP    ;SEQUENCER ADDRESS PORT
    MOV AL,0EH      ;MODE CONTROL REGISTER 1
    OUT DX,AL
    INC DX          ;SEQUENCER DATA PORT
    IN  AL,DX       ;GET OLD BANK
    INC AL          ;INCREMENT THE BANK
```

```
        XOR   AL,02         ;INVERT PAGE BIT
        OUT   DX,AL
        POP   DX
        RET
;
CHKBANK ENDP
        ENDPS
;
        DSEG
SCR_BASE    DD    MBASE_DWORD
        ENDDS
        END
;****************************************************************\
;FUNCTION:
;   rd_px_xy(xpos, ypos)    read a single pixel
;
;ARGUMENTS:
;   int xpos, ypos; X, Y coordinate of pixel to read
;
;DESCRIPTION:
;   reads a single pixel at the specified X, Y coordinate.
;   This function handles converting the X, Y coordinate to
;   the linear address space of the Trident memory map.
;
;****************************************************************/
;
;
        TITLE   read a pixel using X,Y coordinates
        SUBTTL  TONY SCANDURA    10/23/90
        NAME    _RD_PX_XY
;
.286c
INCLUDE MEMMODEL.MAC
INCLUDE TRIDENT.ASM
;
;
        IF    LPROG
X       EQU   8
        ELSE
X       EQU   4
        ENDIF
;
XPOS    EQU   [BP+X]
YPOS    EQU   [BP+X+2]
;
        PSEG
        PUBLIC  _RD_PX_XY
        IF    LPROG
_RD_PX_XY   PROC    FAR
        ELSE
_RD_PX_XY   PROC    NEAR
        ENDIF
        PUSH    BP
        MOV BP,SP
        PUSH    DS
        PUSH    SI
;
;COMPUTE REAL ADDRESS USING Y * 1024 + X
;COMPUTE SEGMENT PART OF ADDRESS
;
        MOV BX,YPOS     ;GET Y VALUE
        SHL BX,1        ;Y * 4
        SHL BX,1
        MOV AH,BH       ;GET SEGMENT VALUE
        XOR AH,02H      ;ADJUST PAGE BIT
        MOV AL,0EH      ;MODE CONTROL REGISTER 1
        MOV DX,SEQAP    ;SEQUENCER ADDRESS PORT
        OUT DX,AX       ;SET TRIDENT SEGMENT REGISTER
;
;COMPUTE OFFSET PART OF ADDRESS
;
```

```
    XOR BH,BH          ;GET RID OF SEGMENT BITS
    XCHG    BH,BL      ;Y * 256
    MOV AX,XPOS        ;GET X VALUE
    ADD AX,BX          ;ADD IN X OFFSET
;
;UPDATE THE SCREEN
;
    LDS SI,DWORD PTR SCR_BASE   ; SET UP POINTER TO SCREEN BASE
    ADD SI,AX          ;POINT TO PIX LOCATION USING DS:SI
    MOV AL,[SI]        ;RETURN THE INTENSITY VALUE
    XOR AH,AH
    POP SI
    POP DS
    POP BP
    RET
;
_RD_PX_XY   ENDP
    ENDPS
;
    DSEG
SCR_BASE    DD  MBASE_DWORD
    ENDDS
    END
;*****************************************************************
******\
;FUNCTION:
;   save_window(source address, dest address, width, height)
;
;ARGUMENTS:
;   char far *source, far *dest;  Memory addr of source and destination
;   int width, height;            Width and height of rectangle
;
;DESCRIPTION:
;   Saves a window to a memory buffer.
;*****************************************************************
******/
;
;
    TITLE   Saves a window to a memory buffer.
    SUBTTL  TONY SCANDURA   11/02/90
    NAME    _SAVEWIN
;
.286c
INCLUDE MEMMODEL.MAC
INCLUDE TRIDENT.ASM
;
;
    IF  LPROG
X   EQU 6
    ELSE
X   EQU 4
    ENDIF
;
SOURCE  EQU [BP+X]
DEST    EQU [BP+X+4]
XLEN    EQU [BP+X+8]
YLEN    EQU [BP+X+10]
;
    PSEG
    PUBLIC  _SAVE_WINDOW
    IF  LPROG
_SAVE_WINDOW    PROC    FAR
    ELSE
_SAVE_WINDOW    PROC    NEAR
    ENDIF
;
    CLI
    PUSH    BP
    MOV BP,SP
    PUSH    DI
    PUSH    SI
```

```
        PUSH    DS
;
        CLD
        LDS  SI,SOURCE      ;SET UP POINTER TO SOURCE
        LES  DI,DEST        ;SET UP POINTER TO DESTINATION
        MOV  CX,YLEN        ;NUMBER OF BYTES IN HEIGHT (Y)
        MOV  AX,BYTESPERLINE ;COMPUTE INCREMENT VALUE FROM END OF ONE
        SUB  AX,XLEN        ;LINE TO BEGINNING OF NEXT LINE - SAVE IN AX
L10:    MOV  BX,CX          ;SAVE COUNTER FOR NUMBER OF ROWS REMAINING
        MOV  CX,XLEN        ;NUMBER OF BYTES IN WIDTH (X)
        REP  MOVSB
        OR   SI,SI          ;IF ZERO, NEED TO UPDATE SEGMENT
        JNZ  L15
        CALL INCBANK
L15:    ADD  SI,AX          ;SOURCE POINTS TO ADDRESS OF NEXT LINE
        JNC  L20            ;IF CARRY, NEED TO UPDATE SEGMENT
        CALL INCBANK        ;UPDATE SEGMENT REGISTER
L20:    MOV  CX,BX          ;GET LOOP COUNTER
        LOOP L10            ;LOOP TIL ALL ROWS DONE
;
        POP  DS
        POP  SI
        POP  DI
        POP  BP
        STI
        RET
;
_SAVE_WINDOW    ENDP
;
;SUBROUTINE TO UPDATE THE SEGMENT REGISTER
;
        IF   LPROG
INCBANK PROC    FAR
        ELSE
INCBANK PROC    NEAR
        ENDIF
        PUSH AX
        MOV  DX,SEQAP       ;SEQUENCER ADDRESS PORT
        MOV  AL,0EH         ;MODE CONTROL REGISTER 1
        OUT  DX,AL
        INC  DX             ;SEQUENCER DATA PORT
        IN   AL,DX          ;GET OLD BANK
        INC  AL             ;INCREMENT THE BANK
        XOR  AL,02          ;INVERT PAGE BIT
        OUT  DX,AL
        POP  AX
        RET
;
INCBANK ENDP
        ENDPS
        END
        TITLE   Set trident segment register
        SUBTTL  Tony Scandura  10-22-90
        NAME    _SET_VID_SEG

INCLUDE MEMMODEL.MAC
        INCLUDE TRIDENT.ASM

IF   LPROG
X       EQU  6
        ELSE
X       EQU  4
        ENDIF

PSEG
        PUBLIC  _SET_VID_SEG
        IF   LPROG
_SET_VID_SEG    PROC    FAR
        ELSE
_SET_VID_SEG    PROC    NEAR
        ENDIF
```

```
        PUSH    BP
        MOV BP,SP

MOV DX,SEQAP    ;SEQUENCER ADDRESS PORT
        MOV AH,[BP+X]   ;GET HIGH ORDER ADDRESS BITS
        XOR AH,02H      ;ADJUST PAGE BIT
        MOV AL,0EH      ;MODE CONTROL REGISTER 1
        OUT DX,AX       ;SELECT BANK, PAGE, AND SEGMENT

POP BP
        RET

_SET_VID_SEG    ENDP
        ENDPS
        END
;****************************************************************\
;FUNCTION:
;   wr_px_xy(xpos, ypos, value) write a single pixel
;
;ARGUMENTS:
;   int xpos, ypos; X, Y coordinate of pixel to write
;   int value;  Intensity value (0 - 255) of pixel
;
;DESCRIPTION:
;   Writes a single pixel of the specified value to the specified
;   X, Y coordinate.  This function handles converting the X, Y
;   coordinate to the linear address space of the Trident memory map.
;
;****************************************************************/
;
;
        TITLE   Write a pixel using X,Y coordinates
        SUBTTL  TONY SCANDURA   10/23/90
        NAME    _WR_PX_XY
;
.286c
INCLUDE MEMMODEL.MAC
INCLUDE TRIDENT.ASM
;
;
        IF  LPROG
X       EQU 6
        ELSE
X       EQU 4
        ENDIF
;
;
XPOS    EQU [BP+X]
YPOS    EQU [BP+X+2]
IVALUE  EQU [BP+X+4]
;
        PSEG
        PUBLIC  _WR_PX_XY
        IF  LPROG
_WR_PX_XY   PROC    FAR
        ELSE
_WR_PX_XY   PROC    NEAR
        ENDIF
        PUSH    BP
        MOV BP,SP
        PUSH    DS
        PUSH    SI
;
;COMPUTE REAL ADDRESS USING Y * 1024 + X
;COMPUTE SEGMENT PART OF ADDRESS
;
        MOV BX,YPOS     ;GET Y VALUE
        SHL BX,1        ;Y * 4
        SHL BX,1
        MOV AH,BH       ;GET SEGMENT VALUE
```

```
        XOR AH,02H         ;ADJUST PAGE BIT
        MOV AL,0EH         ;MODE CONTROL REGISTER 1
        MOV DX,SEQAP       ;SEQUENCER ADDRESS PORT
        OUT DX,AX          ;SET TRIDENT SEGMENT REGISTER
;
;COMPUTE OFFSET PART OF ADDRESS
;
        XOR BH,BH          ;GET RID OF SEGMENT BITS
        XCHG    BH,BL      ;Y * 256
        MOV AX,XPOS        ;GET X VALUE
        ADD AX,BX          ;ADD IN X OFFSET
;
;UPDATE THE SCREEN
;
        LDS SI,DWORD PTR SCR_BASE   ; SET UP POINTER TO SCREEN BASE
        ADD SI,AX          ;POINT TO PIX LOCATION USING DS:SI
        MOV DX,IVALUE      ;GET INTENSITY VALUE
        MOV [SI],DL        ;UPDATE X-Y COORD WITH INTENSITY VALUE
        POP SI
        POP DS
        POP BP
        RET
;
_WR_PX_XY   ENDP
        ENDPS
;
        DSEG
SCR_BASE    DD   MBASE_DWORD
        ENDDS
        END
;************************************************************\
;FUNCTION:
;   char far *xy_to_ad(xpos, ypos); return pointer to x, y address
;
;ARGUMENTS:
;   int xpos, ypos; X, Y coordinate of pixel to write
;
;DESCRIPTION:
;   This function converts the X, Y coordinate to the linear address
;   space of the Trident memory map. It sets the proper segment, and
;   returns a far character pointer to the proper memory location.
;************************************************************/
;
;
        TITLE   Convert X,Y coordinates to pointer to memory
        SUBTTL  TONY SCANDURA    10/22/90
        NAME    _XY_TO_AD
;
.286c
INCLUDE MEMMODEL.MAC
INCLUDE TRIDENT.ASM
;
;
        IF  LPROG
X       EQU 6
        ELSE
X       EQU 4
        ENDIF
;
XPOS    EQU [BP+X]
YPOS    EQU [BP+X+2]
;
        PSEG
        PUBLIC  _XY_TO_AD
        IF  LPROG
_XY_TO_AD   PROC    FAR
        ELSE
_XY_TO_AD   PROC    NEAR
        ENDIF
        PUSH    BP
        MOV BP,SP
```

```
;
;COMPUTE REAL ADDRESS USING Y * 1024 + X
;COMPUTE SEGMENT PART OF ADDRESS
;
    MOV BX,YPOS       ;GET Y VALUE
    SHL BX,1          ;Y * 4
    SHL BX,1
    MOV AH,BH         ;GET SEGMENT VALUE
    XOR AH,02H        ;ADJUST PAGE BIT
    MOV AL,0EH        ;MODE CONTROL REGISTER 1
    MOV DX,SEQAP      ;SEQUENCER ADDRESS PORT
    OUT DX,AX         ;SET TRIDENT SEGMENT REGISTER
;
;COMPUTE OFFSET PART OF ADDRESS
;
    XOR BH,BH         ;GET RID OF SEGMENT BITS
    XCHG   BH,BL      ;Y * 256
    MOV AX,XPOS       ;GET X VALUE
    ADD AX,BX         ;ADD IN X OFFSET
;
;RETURN SCREEN ADDRESS
;
    MOV DX,MBASE_SEG  ;DX = SEGMENT, AX = OFFSET
    POP BP
    RET
;
_XY_TO_AD    ENDP
    ENDPS
    END
/*
Miscellaneous:
*/
#define TRUE (1)
#define FALSE (0)
#define ERROR (-1)

/*
Display Parameters
*/
#define FGDI (160)              /* Foreground pixel intensity */
#define BGDI (60)               /* Background pixel intensity */
#define MAXFGDI (255)   /* Maximum foreground pixel intensity */
#define CHRW (8)                /* Character width */
#define CHRH (16)               /* Character height */
#define MAXVIDBANK (5)
#define MAXCHRLINES (6)
#define MAXSEGLINES (64)
#define BYTESPERLINE (1024)
#define MAXVIDEOLINE (768)
#define MAXBANKBYTES (0xf000)
#define XMID (BYTESPERLINE >> 1)
#define YMID (MAXVIDEOLINE >> 1)
#define XIMAGEPOS (0)
#define YIMAGEPOS (0)
#define XIMAGEBIN (0)
#define YIMAGEBIN (72)
#define XMIDISPLAY (880)
#define YDISPLAYPOS (224)
#define XINSTPOS (552)
#define YINSTPOS (536)
#define XMENUPOS (600)
#define YMENUPOS (280)
#define AXINSTPOS (216)
#define AYINSTPOS (720)
#define AXMENUPOS (0)
#define AYMENUPOS (592)
#define LEFT_IMG (0)
#define RIGHT_IMG (1)

/*
Port Definitions:
```

```c
*/
#define STAT_PORT        0x310    /* Port for inputing status */
#define MODE_PORT        0x310    /* Port for writting status */
#define INT_PORT         0x311    /* Port for integration signal */
#define RSRDOUT_PORT     0x311    /* Port for resetting integrate */
#define RSCLK_PORT       0x312    /* Port for resetting clock and fifo
*/
#define FIFO2_PORT       0x314    /* Port for inputing data from fifo2 */
#define FIFO1_PORT       0x316    /* Port for inputing data from fifo1
*/

/*
Bit Definitions for camera interface card:
*/
/* Status Bits: */
#define XRAY 0x80
#define LINERDY 0x40
#define FF2 0x20
#define HF2 0x10
#define EF2 0x08
#define FF1 0x04
#define HF1 0x02
#define EF1 0x01
/* Mode Bits: */
#define NORMAL_M 0x00
#define BINNED_M 0x01
#define FLUSH_M 0x02
#define LOWER_AMP 0x04
#define UPPER_AMP 0x08
#define BOTH_AMP 0x0C
#define FULL_M 0x00
#define SPLIT_M 0x01

/*
CCD Sensor Parameters:
*/
#define NOPIXELS (32)
#define FORDSIZE (1024)
#define REALFORDSIZE (1056)
#define BINSIZE (512)

/*
Structure for menu window:
*/
struct menwindow
{
        int xlen;
        int ylen;
        char *label[16];
        void far *buffer;
};

/*
Structure for general box:
*/
struct genbox
{
        int xpos;
        int ypos;
        int xlen;
        int ylen;
        void far *buffer;
};

/*
Structure for cursor:
*/
struct curwindow
{
        int     xpos;          /* x position for start of window */
        int     ypos;          /* y position for start of window */
```

```
        int     xpos1;          /* x position for lower right of window
*/
        int     ypos1;          /* y position for lower right of window
*/
        int     ave;            /* flag for average or single pixel */
        int     *pixdata[2];    /* pointers to data under pixel dots */
};

/*
Function key definitions:
*/
#define F1_KEY 0xBB
#define F2_KEY 0xBC
#define F3_KEY 0xBD
#define F4_KEY 0xBE
#define F5_KEY 0xBF
#define F6_KEY 0xC0
#define F7_KEY 0xC1
#define F8_KEY 0xC2
#define F9_KEY 0xC3
#define F10_KEY 0xC4
#define F11_KEY 0x85
#define F12_KEY 0x86
#define M_F11_KEY 0xAD
#define M_F12_KEY 0xB4
#define HOME_KEY 0xC7
#define UP_ARROW 0xC8
#define PG_UP 0xC9
#define LEFT_ARROW 0xCB
#define RIGHT_ARROW 0xCD
#define END_KEY 0xCF
#define TAB_KEY 0x09
#define DOWN_ARROW 0xD0
#define PG_DOWN 0xD1
#define INS_KEY 0xD2
#define DEL_KEY 0xD3
#define ESC_KEY 0x1B
#define SHFT_F0 0xD3
#define SHFT_F1 0xD4
#define SHFT_F2 0xD5
#define SHFT_F3 0xD6
#define SHFT_F4 0xD7
#define SHFT_F5 0xD8
#define SHFT_F6 0xD9
#define SHFT_F7 0xDA
#define SHFT_F8 0xDB
#define SHFT_F9 0xDC
#define SHFT_F10 0xDD
#define SHFT_F11 0x87
#define SHFT_F12 0x88
#define ALT_ENTER_KEY 0x9C
#define CTRL_ENTER_KEY 0x0A
/*******************************************************************
        Header file containing system dependencies and related defines
*******************************************************************/

/*
Bit Definitions for configuring the Trident VGA:
*/
#define DAC6BIT (0)
#define DAC8BIT (1)
#define ENABLE (0)
#define DISABLE (1)
#define CO8025 (0x03)
#define BW8025 (0x07)
#define BW13225 (0x53)
#define CO13225 (0x57)
#define BW13243 (0x54)
#define CO13243 (0x59)
```

```c
#define G64048016   (0x12)
#define G320200256  (0x13)
#define G80060016   (0x5b)
#define G640400256  (0x5c)
#define G640480256  (0x5d)
#define G800600256  (0x5e)
#define G102476016  (0x5f)
#define G10247684   (0x60)
#define G768102416  (0x61)
#define G1024768256 (0x62)

/*
Monochrome text attribute bytes:
*/
#define BOLD          (0x0f)
#define BLINK         (0x87)
#define NORMAL        (0x07)
#define REVERSE       (0x70)
#define UNDERLINE     (0x01)
#define BOLD_REVERSE  (0xf0)
#define BOLD_UNDERLINE (0x09)

/*
Base Memory:
*/
#define CRT_BASE_ADR ((unsigned char far *)0xA0000000)
/*********************************************************
        This function allows annotating the video image
*********************************************************/

/*
        Tony Scandura            11-16-90
*/ include <time.h>
include <stdio.h>
include <fcntl.h>
#include <sys\types.h>
#include <sys\stat.h>
#include "trident.h"
#include "ccd.h"
#include "keys.h"

#define XINSTPOS 512
define YINSTPOS 0 static int kvp = 28, spot, viewptr;
static float exp = 0.5, mas;
static char pt_id[16] = "?", op_id[16] = "?", datebuf[9], timebuf[9];
static char *view[] = {"R CC", "L CC", "R Md Lat", "L Md Lat",
                                        "R Lat Md", "L Lat Md",
"R Axilla", "L Axilla", "?"};
extern int mindisplay, maxdisplay, minimage, maximage;
extern int mincontrast, maxcontrast, invert_flag;
extern unsigned histdata[];
extern char *dbase_fspec;

annotate(ext_flag)
int ext_flag;
{
        int i;
        char *_strdate(), *strtime(), *getinput();
        static struct genbox box = {XINSTPOS, YINSTPOS, 36, 6};
        struct genbox *bp = &box;

pr_xray_parms();
        open_box(bp);
        print_8x16("Type A New ID #, Then Press ENTER",
                                        XINSTPOS + 12, YINSTPOS
 + 16, FGDI, BGDI);
        print_8x16("--- OR ---",
                                                XINSTPOS + (13 << 3),
```

```c
                                        YINSTPOS + 40, FGDI, BGDI);
        print_8x16("Press ENTER To Leave ID Unchanged",
                                                            XINSTPOS + 12, YINSTPOS
+ 64, FGDI, BGDI);
            getinput(pt_id, 13, 0, 10);
            getinput(op_id, 13, 24, 10);

rev_fgd_bkgd(38 << 3, 0, FGDI, 0, 40, 16);
            print_8x16(" Arrow Keys Or Spacebar To Change ",
                                                            XINSTPOS + 8, YINSTPOS +
16, FGDI, BGDI);
            print_8x16("   Press ENTER To Leave Unchanged  ",
                                                            XINSTPOS + 8, YINSTPOS +
64, FGDI, BGDI);
            while((i = get_key()) != '\r')
            {
                    switch(i)
                    {
                            case ' ':
                            case DOWN_ARROW:
                            case RIGHT_ARROW:
                            case UP_ARROW:
                            case LEFT_ARROW:
                                    spot ^= 1;
                                    pr_xray_parms();
                                    rev_fgd_bkgd(38 << 3, 0, FGDI, 0, 40,
16);
                                    break;
                    }
            }
            rev_fgd_bkgd(38 << 3, 0, FGDI, 0, 40, 16);

if(datebuf[0] == '?' || ext_flag == TRUE)
            {
                    date_stamp_annot(0);
                    print_8x16("Type A New Date, Then Press ENTER",
                                                            XINSTPOS + 12, YINSTPOS
+ 16, FGDI, BGDI);
                    getinput(datebuf, 55, 0, 8);
                    print_8x16("Time", XINSTPOS + 100, YINSTPOS + 16, FGDI,
BGDI);
                    getinput(timebuf, 55, 24, 8);
                    print_8x16(" Arrow Keys Or Spacebar To Change ",
                                                            XINSTPOS + 8, YINSTPOS +
16, FGDI, BGDI);
            } rev_fgd_bkgd(5 << 3, 48, FGDI, 0, 16, 16);
            while((i = get_key()) != '\r')
            {
                    switch(i)
                    {
                            case ' ':
                            case UP_ARROW:
                            case RIGHT_ARROW:
                                    ++kvp;
                                    if(kvp > 39 || kvp == 1) kvp = 22;
                                    pr_xray_parms();
                                    rev_fgd_bkgd(5 << 3, 48, FGDI, 0, 16,
16);
                                    break;
                            case DOWN_ARROW:
                            case LEFT_ARROW:
                                    if(--kvp < 22) kvp = 39;
                                    pr_xray_parms();
                                    rev_fgd_bkgd(5 << 3, 48, FGDI, 0, 16,
16);
                                    break;
                    }
            }
            rev_fgd_bkgd(5 << 3, 48, FGDI, 0, 16, 16);
```

```
if(exp == 0.0 || ext_flag == TRUE)
{
        rev_fgd_bkgd(42 << 3, 48, FGDI, 0, 24, 16);
        while((i = get_key()) != '\r')
        {
                switch(i)
                {
                        case ' ':
                        case UP_ARROW:
                        case RIGHT_ARROW:
                                if((exp += 0.1) > 5.0) exp = 0.1;
                                pr_xray_parms();
                                rev_fgd_bkgd(42 << 3, 48, FGDI, 0, 24, 16);
                                break;
                        case DOWN_ARROW:
                        case LEFT_ARROW:
                                if((exp -= 0.1) < 0.1) exp = 5.0;
                                pr_xray_parms();
                                rev_fgd_bkgd(42 << 3, 48, FGDI, 0, 24, 16);
                                break;
                }
        }
        rev_fgd_bkgd(42 << 3, 48, FGDI, 0, 24, 16);
} rev_fgd_bkgd(55 << 3, 48, FGDI, 0, 64, 16);
while((i = get_key()) != '\r')
{
        switch(i)
        {
                case ' ':
                case UP_ARROW:
                case RIGHT_ARROW:
                        if(++viewptr > 7) viewptr = 0;
                        pr_xray_parms();
                        rev_fgd_bkgd(55 << 3, 48, FGDI, 0, 64, 16);
                        break;
                case DOWN_ARROW:
                case LEFT_ARROW:
                        if(--viewptr < 0) viewptr = 7;
                        pr_xray_parms();
                        rev_fgd_bkgd(55 << 3, 48, FGDI, 0, 64, 16);
                        break;
        }
}
rev_fgd_bkgd(55 << 3, 48, FGDI, 0, 64, 16);

close_box(bp);
} char *getinput(buffer, xpos, ypos, length)
char *buffer;
int xpos, ypos, length;
{
        int i, j;
        char pchar[2], boxes[16];

xpos *= CHRW;
        pchar[0] = '\xfe';
        pchar[1] = '\0';
        for(i = 0; i < length; i++)
                boxes[i] = '\xfe';
        boxes[i] = '\0';
        rev_fgd_bkgd(xpos, ypos, FGDI, 0, length << 3, 16);
        do
```

```c
        {
                if((boxes[0] = get_key()) == '\r')
                {
                        rev_fgd_bkgd(xpos, ypos, FGDI, 0, length << 3, 16);
                        return;
                }
                if(boxes[0] == ' ') boxes[0] = '_';
        }
        while(boxes[0] < 44 || boxes[0] > 122);
        print_8x16(boxes, xpos, ypos, FGDI, 0);
        *buffer = boxes[0];
        i = 1;
        xpos += CHRW;
        while((*pchar = get_key()) != '\r')
        {
                if(*pchar == '\b')
                {
                        if(i)
                        {
                                print_8x16("\xfe", xpos -= CHRW, ypos, FGDI, 0);
                                i--;
                        }
                }
                else
                {
                        if(*pchar == ' ') *pchar = '_';
                        if(i < length && *pchar > 43 && *pchar < 123)
                        {
                                print_8x16(pchar, xpos, ypos, FGDI, 0);
                                xpos += CHRW;
                                *(buffer + i++) = *pchar;
                        }
                }
        }
        *(buffer + i) = '\0';
        j = 0;
        while(i++ < length)
                boxes[j++] = ' ';
        boxes[j] = '\0';
        print_8x16(boxes, xpos, ypos, FGDI, 0);
} pr_xray_parms()
{
        int ma = 0;
        char buffer[64];

if(kvp > 21 && kvp < 29)
                ma = (spot) ? 20 : 80;
        else if(kvp > 28 && kvp < 35)
                ma = (spot) ? 17 : 70;
        else if(kvp > 34 && kvp < 40)
                ma = (spot) ? 15 : 60;
        sprintf(buffer, "Patient ID : %-14sSpot Size: %-11sDate: %-8s",
                        pt_id, (spot) ? "Small" : "Large", datebuf);
        print_8x16(buffer, 0, 0, FGDI, 0);
        sprintf(buffer, "Operator ID: %-14sManual  Exposure     Time: %-8s",
                        op_id, timebuf);
        print_8x16(buffer, 0, 24, FGDI, 0);
        sprintf(buffer,
                        "kVp: %2d    mAs: %5.1f    Exposure Time: %3.1f   View: %-8s",
                        kvp, ma * exp, exp, view[viewptr]);
        print_8x16(buffer, 0, 48, FGDI, 0);
} save_annotation(fspec)
char *fspec;
```

```
{
        FILE *stream;
        char buffer[64], *strcat(), *strrchr();
        int fp;

sscanf(fspec, "%[^.]", buffer);
        strcat(buffer, ".dat");
        if((stream = fopen(buffer, "w")) == NULL)
        {
                pr_error(0);
                return(ERROR);
        }
        sscanf(fspec, "%[^.]", buffer);
        strcat(buffer, ".dsp");
        if((fp = open(buffer, O_RDWR | O_CREAT | O_BINARY,
                                        S_IREAD | S_IWRITE)) ==
ERROR)
        {
                pr_error(0);
                fclose(stream);
                return(ERROR);
        }
        fprintf(stream, "%s %s %d %f %d %s %s %d %d %d %d %d %d %d %d",
                                        pt_id, op_id, kvp, exp, spot,
datebuf, timebuf,
                                        viewptr, mindisplay, maxdisplay,
minimage,
                                        maximage, mincontrast,
maxcontrast, invert_flag);
        write(fp, histdata, 256 * sizeof(int));
        fclose(stream);
        close(fp);
        if((fp = open(dbase_fspec, O_RDWR | O_CREAT | O_BINARY |
O_APPEND,
                                        S_IREAD | S_IWRITE)) ==
ERROR)
        {
                pr_error(0);
                return(ERROR);
        }
        sscanf(fspec, "%[^.]", buffer);
        strcpy(buffer + 40, strrchr(buffer, '\\'));
        strcpy(buffer, pt_id);
        strcpy(buffer + 16, op_id);
        strcpy(buffer + 32, datebuf);
        write(fp, buffer, 50);
        close(fp);
        return(0);
} rec_annotation(fspec)
char *fspec;
{
        FILE *stream;
        char buffer[64], *strcat();
        int i, fp;

sscanf(fspec, "%[^.]", buffer);
        strcat(buffer, ".dat");
        if((stream = fopen(buffer, "r")) == NULL)
        {
                sprintf(pt_id, "?");
                sprintf(op_id, "?");
                sprintf(datebuf, "?");
                sprintf(timebuf, "?");
                kvp = 0, exp = 0.0, viewptr = 8;
                pr_xray_parms();
                return(ERROR);
        }
        sscanf(fspec, "%[^.]", buffer);
        strcat(buffer, ".dsp");
```

```
        if((fp = open(buffer, O_RDWR | O_BINARY, S_IREAD | S_IWRITE)) !=
ERROR)
        {
                read(fp, histdata, 256 * sizeof(int));
                close(fp);
        }
        i = fscanf(stream, "%s %s %d %f %d %s %s %d %d %d %d %d %d %d
%d",
                                            pt_id, op_id, &kvp, &exp, &spot,
datebuf, timebuf,
                                            &viewptr, &mindisplay,
&maxdisplay, &minimage,
                                            &maximage, &mincontrast,
&maxcontrast, &invert_flag);
        fclose(stream);
        if(i != 15), viewptr = 8;
        pr_xray_parms();
        if(i == 15) return(0);
        return(ERROR);
} date_stamp_annot(time)
int time;
{
        _strdate(datebuf);
        _strtime(timebuf);
        time = (time + 50) / 100;
        exp = time / 10.0;
        pr_xray_parms();
} del_annotation(fspec)
char *fspec;
{
        FILE *stream;
        char buffer[64], *strcat();

sscanf(fspec, "%[^.]", buffer);
        strcat(buffer, ".dat");
        unlink(buffer);
        sscanf(fspec, "%[^.]", buffer);
        strcat(buffer, ".dsp");
        return(unlink(buffer));
}

/***************************************************************
        This is the main program for controlling the CCD camera
            (using the FORD 1024 CCD sensor and the VGA monitor)
****************************************************************/

/*
        Tony Scandura          10-25-90
*/ include <dos.h>
include <stdio.h>
#include "trident.h"
#include "ccd.h"
#include "keys.h"

#define XCURSOR (XIMAGEBIN)
#define YCURSOR (YIMAGEBIN)
#define XCURSOR1 (XIMAGEBIN + BINSIZE - 1)
#define YCURSOR1 (YIMAGEBIN + BINSIZE - 1)
#define XMENUMAX (839)
#define YMENUMAX (543)
#define XEXITPOS (XMID - 196)
#define YEXITPOS (160)
#define XCURMODELEN (44)
#define YCURMODELEN (3)
#define XCURMODEPOS (528)
#define YCURMODEPOS (MAXVIDEOLINE - YCURMODELEN * CHRH)
```

```c
int xmenu = XMENUPOS, ymenu = YMENUPOS, altpixdata[49];
char *fin_filespec = "d:_image.fin";
char *tmp_filespec = "e:_image.tmp";
char *wht_filespec = "f:_image.wht";
char *drk_filespec = "g:_image.drk";
char *hf_wht_fspec = "c:\\images\\_image.wht";
char *hb_wht_fspec = "c:\\images\\_bimage.wht";
char *hf_drk_fspec = "c:\\images\\_image.drk";
char *hb_drk_fspec = "c:\\images\\_bimage.drk";
char *cnf_filespec = "c:\\trident\\ccd.cnf";
char *stereo_filespec = "c:\\trident\\ccd.cal";
struct curwindow altcursor =
        {XIMAGEBIN + 256, YIMAGEBIN + 256, XCURSOR1, YCURSOR1, FALSE,
altpixdata};
struct genbox instbox = {XINSTPOS, YINSTPOS, 36, 3};
static char *instructions[] =
{
        "Press ENTER When Ready For X-Ray",
        "Contrast/Data Window / Histogram",
        "Labels For ID & X-Ray Parameters",
        "Recall Image By: ID, Name, Date ",
        "Change Acquisition Or CRT Modes ",
        "Orderly Exit and Park Disk Heads",
        "Contrast/Data Window / Histogram",
        "Press ENTER To Start Stereo Mode",
        "Change Acquisition Or CRT Modes ",
        "Alter Rotation Angle/Select Mode"
};
static char *acq_msg[] =
{
        "Resolution (1024)",
        "Sensitivity (512)"
};
extern int bin_mode, crt_mode, stereo_mode;

main()
{
        int video_mode, i;
        static int pixdata1[49], pixdata2[49];
        static struct menwindow menu =
        {
                18, 7, " -- Main  Menu --", "F1: Acquire Image", "F2: Process Image",
                "F3: Annotate Image", "F4: Recall Image", "F5: Change Mode",
                "F6: Exit Program"
        };
        static struct menwindow stereo_menu =
        {
                18, 7, "-- Stereo  Menu --", "F1: Acquire Image", "F2: Acquire Stereo",
                "F3: Annotate Image", "F4: Recall Image", "F5: Change Mode",
                "F6: Exit Program"
        };
        static struct curwindow cursorw =
                {XCURSOR, YCURSOR, XCURSOR1, YCURSOR1, FALSE, pixdata1, pixdata2};
        static struct genbox exbox = {XEXITPOS, YEXITPOS, 49, 3};
        struct menwindow *wp = &menu;
        struct genbox *ip = &instbox, *eb = &exbox;
        struct curwindow *cp = &cursorw, *altcp = &altcursor;

get_defaults();
        rec_calibration();
        set_char_adr();
        init_ford();
        unlink(fin_filespec);

video_mode = get_vid_mode();
```

```
set_gs_summing(DISABLE);
set_df_pallet(DISABLE);
set_vid_mode(G1024768256);
reset_grayscales();
make_dirdata();

while(1)
{
        wp = (stereo_mode) ? &stereo_menu : &menu;
        strcpy(instructions[1], instructions[stereo_mode + 6]);
        strcpy(instructions[4], instructions[stereo_mode + 8]);
        pr_settings();
        if(crt_mode == 1)
        {
                instbox.xpos = AXINSTPOS, instbox.ypos = AYINSTPOS;
                xmenu = AXMENUPOS, ymenu = AYMENUPOS;
        }
        else if(!crt_mode)
        {
                instbox.xpos = XINSTPOS, instbox.ypos = YINSTPOS;
                xmenu = XMENUPOS, ymenu = YMENUPOS;
        }
        open_box(ip);
        switch(get_menu_ptr(wp, TRUE, TRUE))
        {
        case 0:
                close_box(ip);
                if(int_image(fin_filespec) != ERROR)
                {
                        chg_contrast();
                        auto_save_it();
                }
                break;
        case 0x80:
                close_box(ip);
                if(crt_mode)
                {
                        i = ymenu;
                        ymenu -= 64;
                }
                integrate(cp);
                if(crt_mode)
                        ymenu = i;
                break;
        case 1:
                close_box(ip);
                (stereo_mode) ? do_stereo() : chg_contrast();
                break;
        case 0x81:
                close_box(ip);
                if(crt_mode)
                {
                        i = ymenu;
                        ymenu -= 96;
                }
                (stereo_mode) ? calibrate() : contrast(cp, 1);
                if(crt_mode)
                        ymenu = i;
                break;
        case 2:
                close_box(ip);
                annotate(FALSE);
                break;
        case 0x82:
                close_box(ip);
                annotate(TRUE);
                break;
        case 3:
                close_box(ip);
```

```
                        rec_it(0);
                        break;
                case 0x83:
                        close_box(ip);
                        if(crt_mode)
                        {
                                i = ymenu;
                                ymenu -= 48;
                        }
                        disk_io(1);
                        if(crt_mode)
                                ymenu = i;
                        break;
                case 4:
                case 0x84:
                        close_box(ip);
                        (stereo_mode) ? get_stereo_settings() :
get_norm_settings();
                        break;
                case 5:
                case 0x85:
                        close_box(ip);
                        open_box(eb);
                        print_8x16("Are You Sure You Wish To Exit
Program ? (y/n)",
                                                XEXITPOS + 16, YEXITPOS + 16,
FGDI, BGDI);
                        i = get_key();
                        if(i == 'y' || i == 'Y')
                        {
                                close_box(eb);
                                set_gs_summing(ENABLE);
                                set_df_pallet(ENABLE);
                                set_vid_seg(0x00);
                                set_vid_mode(video_mode);
                                exit();
                        }
                        close_box(eb);
                        break;
                }
        }
} make_box(xpos, ypos, width, height)
int xpos, ypos, width, height;
{
        int i, x = xpos, y = ypos;
        char top[64], bot[64], line[64], space[64];

width--;
        height -= 6;
        bot[0] = 200;
        top[0] = 201;
        line[0] = 199;
        space[0] = 186;
        for(i = 1; i < width; i++)
        {
                bot[i] = top[i] = 205;
                line[i] = 196;
                space[i] = 32;
        }
        bot[i] = 188;
        top[i] = 187;
        line[i] = 182;
        space[i++] = 186;
        bot[i] = top[i] = line[i] = space[i] = '\0';

print_8x16(top, x, y, FGDI, BGDI);
        print_8x16(space, x, y += 16, FGDI, BGDI);
        print_8x16(line, x, y += 16, FGDI, BGDI);
        while(height--)
```

```c
            {
                    print_8x16(space, x, y += 16, FGDI, BGDI);
            }
            print_8x16(line, x, y += 16, FGDI, BGDI);
            print_8x16(space, x, y += 16, FGDI, BGDI);
            print_8x16(bot, x, y += 16, FGDI, BGDI);
    } open_window(wp)
struct menwindow *wp;
{
        void far *_fmalloc();
        int i, menulen, xpos = xmenu, ypos = ymenu, xlen, ylen;
        char far *src, far *xy_to_ad(), far *mbuffer;

xlen = wp->xlen + 4;
        ylen = wp->ylen + 4;
        if((wp->buffer = _fmalloc(xlen * ylen << 7)) == NULL)
                exit();
        menulen = ylen - 5;
        mbuffer = (char far *)wp->buffer;

src = xy_to_ad(xpos, ypos);
        save_window(src, mbuffer, xlen << 3, ylen << 4);

make_box(xmenu, ymenu, xlen, ylen);

ypos = ymenu + 16;
        print_8x16(wp->label[0], xpos += 16, ypos, FGDI, BGDI);
        for(i = 1, ypos += 16; i < menulen; i++)
                print_8x16(wp->label[i], xpos, ypos += 16, FGDI, BGDI);
        print_8x16(wp->label[i], xpos, ypos += 32, FGDI, BGDI);

} close_window(wp)
struct menwindow *wp;
{
        int xpos = xmenu, ypos = ymenu;
        char far *dest, far *xy_to_ad(), far *mbuffer;

mbuffer = (char far *)wp->buffer;

dest = xy_to_ad(xpos, ypos);
        rec_window(mbuffer, dest, wp->xlen + 4 << 3, wp->ylen + 4 << 4);

_ffree(wp->buffer);
} make_gen_box(xpos, ypos, width, height)
int xpos, ypos, width, height;
{
        int i;
        char top[80], bot[80], space[80];

width--;
        bot[0] = 200;
        top[0] = 201;
        space[0] = 186;
        for(i = 1; i < width; i++)
        {
                bot[i] = top[i] = 205;
                space[i] = 32;
        }
        bot[i] = 188;
        top[i] = 187;
        space[i++] = 186;
        bot[i] = top[i] = space[i] = '\0';
```

```
                print_8x16(top, xpos, ypos, FGDI, BGDI);
                height -= 2;
                while(height--)
                {
                        print_8x16(space, xpos, ypos += 16, FGDI, BGDI);
                }
                print_8x16(bot, xpos, ypos += 16, FGDI, BGDI);
} open_box(bp)
struct genbox *bp;
{
        void far *_fmalloc();
        char far *src, far *xy_to_ad(), far *mbuffer;

if((bp->buffer = _fmalloc(bp->xlen * bp->ylen << 7)) == NULL)
                exit();
        mbuffer = (char far *)bp->buffer;
        src = xy_to_ad(bp->xpos, bp->ypos);
        save_window(src, mbuffer, bp->xlen << 3, bp->ylen << 4);
        make_gen_box(bp->xpos, bp->ypos, bp->xlen, bp->ylen);
} close_box(bp)
struct genbox *bp;
{
        int xpos = bp->xpos, ypos = bp->ypos;
        char far *dest, far *xy_to_ad(), far *mbuffer;

mbuffer = (char far *)bp->buffer;
        dest = xy_to_ad(xpos, ypos);
        rec_window(mbuffer, dest, bp->xlen << 3, bp->ylen << 4);
        _ffree(bp->buffer);
} get_menu_ptr(wp, window_flag, inst_flag)
struct menwindow *wp;
int window_flag, inst_flag;
{
        int i, revx, revy, revlen, menupt = 0, xinst, yinst;

xinst = instbox.xpos + 16;
        yinst = instbox.ypos + 16;
        revlen = (wp->xlen << 3) + 4;
        revx = xmenu + 14, revy = ymenu + 3 * CHRH + menupt * CHRH;
        if(window_flag) open_window(wp);
        rev_fgd_bkgd(revx, revy, FGDI, BGDI, revlen, CHRH);
        while(1)
        {
                if(inst_flag)
                        print_8x16(instructions[menupt], xinst, yinst,
FGDI, BGDI);
                switch(i = get_key())
                {
                case UP_ARROW:
                case LEFT_ARROW:
                        if(menupt == wp->ylen - 2)
                        {
                                menupt--;
                                rev_fgd_bkgd(revx, revy, FGDI, BGDI,
revlen, CHRH);
                                revy -= CHRH << 1;
                                rev_fgd_bkgd(revx, revy, FGDI, BGDI,
revlen, CHRH);
                        }
                        else if(menupt > 0)
                        {
                                menupt--;
                                revy -= CHRH;
                                rev_fgd_bkgd(revx, revy, FGDI, BGDI,
```

```
revlen, 32);
                                }
                                break;
                        case DOWN_ARROW:
                        case RIGHT_ARROW:
                                if(menupt < wp->ylen - 3)
                                {
                                        menupt++;
                                        rev_fgd_bkgd(revx, revy, FGDI, BGDI,
revlen, 32);
                                        revy += CHRH;
                                }
                                else if(menupt == wp->ylen - 3)
                                {
                                        menupt++;
                                        rev_fgd_bkgd(revx, revy, FGDI, BGDI,
revlen, CHRH);
                                        revy += CHRH << 1;
                                        rev_fgd_bkgd(revx, revy, FGDI, BGDI,
revlen, CHRH);
                                }
                                break;
                        case '\r':
                                if(window_flag) close_window(wp);
                                return(menupt);
                                break;
                        case CTRL_ENTER_KEY:
                                if(window_flag) close_window(wp);
                                return(menupt | 0x80);
                                break;
                        case ESC_KEY:
                                If(window_flag) close_window(wp);
                                return(wp->ylen - 2);
                                break;
                        case SHFT_F1:
                                disp_full_screen();
                                break;
/*
                        case SHFT_F12:
                                if(window_flag) close_window(wp);
                                print_screen();
                                if(window_flag) open_window(wp);
                                rev_fgd_bkgd(revx, revy, FGDI, BGDI, revlen,
CHRH);
                                break;
*/
                        }
                        i -= F1_KEY;
                        if(i > -1 && i < wp->ylen - 1)
                        {
                                menupt = i;
                                rev_fgd_bkgd(revx, revy, FGDI, BGDI, revlen,
CHRH);
                                revy = ymenu + 3 * CHRH + menupt * CHRH;
                                if(i == wp->ylen - 2) revy += CHRH;
                                rev_fgd_bkgd(revx, revy, FGDI, BGDI, revlen,
CHRH);
                                if(window_flag) close_window(wp);
                                return(menupt);
                        }
                }
        }
}
move_menu(cp)
struct curwindow *cp;
{
        static struct menwindow menu =
        {
                15, 7, " - Move Menu -", "F1: Cursor", "F2: Upper Left",
"F3: Upper Right",
                "F4: Lower Left", "F5: Lower Right", " F6: Main Menu"
```

```
                };
                struct menwindow *wp;

wp = &menu;
                while(1)
                {
                        switch(get_menu_ptr(wp, TRUE, FALSE))
                        {
                        case 0:
                                move_cursor(cp, FALSE, LEFT_IMG);
                                wr_cursor(cp->pixdata[0], cp->xpos, cp->ypos);
                                xmenu = (cp->xpos > XMENUMAX) ? XMENUMAX :
cp->xpos;
                                ymenu = (cp->ypos > YMENUMAX) ? YMENUMAX :
cp->ypos;
                                break;
                        case 1:
                                xmenu = ymenu = 0;
                                break;
                        case 2:
                                xmenu = XMENUMAX;
                                ymenu = 0;
                                break;
                        case 3:
                                xmenu = 0;
                                ymenu = YMENUMAX;
                                break;
                        case 4:
                                xmenu = XMENUMAX;
                                ymenu = YMENUMAX;
                                break;
                        case 5:
                        case 6:
                                return;
                                break;
                        }
                }
}
analyze(cp)
struct curwindow *cp;
{
        static struct menwindow menu =
        {
                14, 5, " - Analyze -", "F1: Histograms", "F2: Plot
Data",
                "F3: List Data", "F4: Main Menu"
        };
        struct menwindow *wp;

wp = &menu;
        while(1)
        {
                switch(get_menu_ptr(wp, TRUE, FALSE))
                {
                case 0:
                        histogram(cp);
                        break;
                case 1:
                        sav_image(tmp_filespec);
                        plot(cp);
                        get_key();
                        if(restore_image() == 'y')
                                rec_image(tmp_filespec);
                        break;
                case 2:
                        print_data(cp);
                        break;
                case 3:
                        return;
                        break;
```

```c
        }
    }
}
get_norm_settings()
{
    int i, oldcrtmode, oldbinmode;
    static struct menwindow menu =
    {
        24, 7, " -- Mode Change Menu --", "F1: Hi Resolution
(1024)",
        "F2: Hi Sensitivity (512)", "F3: Single Image Display",
        "F4: Side By Side Display", "F5: Turn Stereo Mode On",
        "F6: Main Menu/No Changes"
    };
    struct menwindow *wp;

oldcrtmode = crt_mode;
    oldbinmode = bin_mode;

wp = &menu;
    switch(i = get_menu_ptr(wp, TRUE, FALSE))
    {
        case 0:
        case 1:
            bin_mode = i;
            break;
        case 2:
        case 3:
            crt_mode = i - 2;
            break;
        case 4:
            stereo_mode = bin_mode = crt_mode = 1;
            break;
        case 5:
            break;
    }
    if(oldbinmode != bin_mode)
        init_ford();
    if(oldcrtmode != crt_mode && !crt_mode)
        clear_image(1);
}
pr_settings()
{
    char buf[64];

make_gen_box(XCURMODEPOS, YCURMODEPOS, XCURMODELEN,
YCURMODELEN);
    sprintf(buf, "Acquisition Mode: High %s", acq_msg[bin_mode]);
    print_8x16(buf, XCURMODEPOS + (CHRW << 1), YCURMODEPOS + CHRH,
FGDI, BGDI);
} clear_image(lr)
int lr;
{
    int i;
    char far *dest, far *xy_to_ad();

lr *= BINSIZE;
    for(i = 0; i < YIMAGEBIN + BINSIZE + 72; i++)
    {
        dest = xy_to_ad(lr, i);
        *dest = '\0';
        mem_to_mem(dest, dest + 1, BINSIZE - 1);
    }
}
/***************************************************************
        These functions manipulate the luminance tables and data
        in memory to change the brightness and contrast
****************************************************************/
```

```c
/*
Tony Scandura          11-05-90
*/ include <stdio.h>
include "ccd.h"
#include "keys.h"

#define EX_COMPILE (FALSE)
#define XHISTPOS (544)
#define YHISTPOS (88)
#define XINSTPOS (XHISTPOS)
#define YINSTPOS (280 + YHISTPOS)
#define HISTI (160)
#define O_INC 4
#define S_INC 1
#define XSLOFBX (XMIDISPLAY - 124)
#define YSLOFBX (YDISPLAYPOS)
#define XSLICEBX (416)
#define YSLICEBX (20)
#define MAXBINS 256
extern struct curwindow altcursor;
extern char *fin_filespec, *tmp_filespec;
extern int maxdisplay, mindisplay;
int maxcontrast, mincontrast, invert_flag = 1;
unsigned histdata[256];

contrast(cp, ext_flag)
struct curwindow *cp;
{
        int menupt;
        static int hist_on;

static struct menwindow menu =
        {
                22, 8, " - Processing  Menu -", "F1: Contrast / Window",
                "F2: Region Of Interest", "F3: Histogram Equalize",
                "F4: Stretch Contrast", "F5: Convolution Filter",
                "F6: Histogram On/Off", "F7: - Main  Menu  -"
        };
        static struct menwindow ext_menu =
        {
                22, 12, " - Processing  Menu -", "F1: Contrast / Window",
                "F2: Region Of Interest", "F3: Histogram Equalize",
                "F4: Stretch Contrast", "F5: Convolution Filter",
                "F6: Histogram On/Off", "F7: Disk Services", "F8: Std Deviation",
                "F9: Modify LUTs", "F10: Set Display Bits", " -- Main  Menu --"
        };
        struct menwindow *wp;
        struct curwindow *altcp;

altcp = &altcursor;
        wp = (ext_flag) ? &ext_menu : &menu;

if(hist_on)
                histgram(cp, 0, 0, 1);
        while(1)
        {
                menupt = get_menu_ptr(wp, TRUE, FALSE);
                if(hist_on)
                        histgram(cp, 0, 0, 0);
                switch(menupt)
                {
                case 0:
                        chg_contrast();
                        break;
                case 1:
                        xycursor(cp);
                        break;
```

```
                case 2:
                        equalize(cp);
                        break;
                case 3:
                        stretch(cp);
                        break;
                case 4:
                        convolve(cp);
                        break;
                case 5:
                        hist_on ^= 1;
                        break;
                }
                if(ext_flag)
                switch(menupt)
                {
                case 6:
                        disk_io(0);
                        break;
                case 0x86:
                        disk_io(1);
                        break;
                case 7:
                        get_stdev(fin_filespec, cp);
                        break;
                case 8:
                        lumtable(cp);
                        break;
                case 9:
                        set_display_bits(TRUE);
                        break;
                case 10:
                        if(hist_on)
                                histgram(cp, 0, 0, 0);
                        return;
                        break;
                }
                else if(menupt == 6)
                {
                        if(hist_on)
                                histgram(cp, 0, 0, 0);
                        return;
                }
                if(hist_on)
                        histgram(cp, 0, 0, 1);
        }
}

/************************************************************
        This function manipulates the luminance look up tables
************************************************************/ lumtable(cp)
struct curwindow *cp;
{
        int i, j, xstart, ystart, x, y;
        char buf[32];
        int xprint = XSLOFBX + (CHRW << 1), yprint = YSLOFBX + CHRH;
        static int offset = 0, slope = 10;
        static unsigned char far *ptable, far buffer[768], graybuf[256];
        unsigned char *pgraybuf, far *xy_to_ad();
        static struct genbox box1 = {XSLOFBX, YSLOFBX, 31, 3};
        static struct genbox box = {XHISTPOS, YHISTPOS, 36, 11};
        struct genbox *bp, *bp1;
        bp = &box;
        bp1 = &box1;

open_box(bp);
        xstart = x = XHISTPOS + (CHRW << 1);
        ystart = y = YHISTPOS + 112;
```

```c
        for (i = 0, pgraybuf = graybuf; i < 256; i++)
        {
                y = ystart;
                wr_px_xy(x++, y - *pgraybuf++, HISTI);
        }
        y = CHRH;
        ystart += 2;
        while(y--)
        {
                ptable = xy_to_ad(xstart, ystart++);
                for(i = 0; i < 256; i++)
                        *ptable++ = i;
        }
        ystart++;
        ptable = xy_to_ad(xstart, ystart++);
        for(i = 0; i < 256; i++)
                *ptable++ = HISTI;
        y = 4;
        ystart++;
        while(y--)
        {
                ptable = xy_to_ad(xstart, ystart++);
                for(i = 0; i < 256; i++)
                        *ptable++ = (i % 32) ? BGDI : HISTI;
                *--ptable = HISTI;
        }
        ystart++;
        print_8x8("0   32   64   96   128  160  192  224  256",
                                                xstart - 3, ystart,
HISTI, BGDI);

xstart = x = XHISTPOS + (CHRW << 1);
        ystart = y = YHISTPOS + 112;
        while((i = get_key()) != '\r')
        {
                switch(i)
                {
                        case UP_ARROW:
                                offset += O_INC;
                                break;
                        case DOWN_ARROW:
                                offset -= O_INC;
                                break;
                        case LEFT_ARROW:
                                slope += S_INC;
                                break;
                        case RIGHT_ARROW:
                                slope -= S_INC;
                                break;
                        case ' ':
                                slope = 10;
                                offset = 0;
                                break;
                        case F1_KEY:
                                invert_video(XIMAGEPOS, YIMAGEPOS,
FORDSIZE, MAXVIDEOLINE);
                                break;
                }
                x = xstart;
                for (i = 0, pgraybuf = graybuf; i < 256; i++)
                        wr_px_xy(x++, y - *pgraybuf++, BGDI);
                for(i = 0, ptable = buffer, pgraybuf = graybuf; i < 256;
i++)
                {
                        j = (slope * i) / 10 + offset >> 2;
                        if(j < 0) j = 0;
                        if(j > 63) j = 63;
                        *pgraybuf++ = j;
                        *ptable++ = j;
                        *ptable++ = j;
                        *ptable++ = j;
```

```
                }
                load_grayscale(buffer);
                x = xstart;
                for (i = 0, pgraybuf = graybuf; i < 256; i++)
                        wr_px_xy(x++, y - *pgraybuf++, HISTI);
        }
        close_box(bp);
        open_box(bp1);
        print_8x16("Convert To In Memory Data ? ", xprint, yprint,
HISTI, BGDI);
        i = get_key();
        close_box(bp1);
        if (i == 'y')
                translate(cp, buffer);
        slope = 10;
        offset = 0;
        for(i = 0, ptable = buffer, pgraybuf = graybuf; i < 256; i++)
        {
                j = (slope * i) / 10 + offset >> 2;
                if(j < 0) j = 0;
                if(j > 63) j = 63;
                *pgraybuf++ = j;
                *ptable++ = j;
                *ptable++ = j;
                *ptable++ = j;
        }
        load_grayscale(buffer);
}

/***********************************************************************
******
        This function performs linear contrast stretch on data in video
memory
************************************************************************
*****/

/*
Tony Scandura    4-22-90
*/ stretch(cp)
struct curwindow *cp;
{
        int x, y, ystart, xstart, cols, rows;
        unsigned big, small;
        unsigned char far *pmem, far *xy_to_ad();

big = 0, small = 255;
        xstart = (cp->xpos < cp->xpos1) ? cp->xpos : cp->xpos1;
        cols = abs(cp->xpos - cp->xpos1) + 1;
        y = ystart = (cp->ypos < cp->ypos1) ? cp->ypos : cp->ypos1;
        rows = abs(cp->ypos - cp->ypos1) + 1;
        while(rows--)
        {
                pmem = xy_to_ad(xstart, y++);
                x = cols;
                while(x--)
                {
                        small = (small < *pmem) ? small : *pmem;
                        big = (big > *pmem) ? big : *pmem;
                        pmem++;
                }
        }
        big -= small;
        y = ystart;
        rows = abs(cp->ypos - cp->ypos1) + 1;
        while(rows--)
        {
                pmem = xy_to_ad(xstart, y++);
                x = cols;
                while(x--)
```

```
                {
                        *pmem -= small;
                        *pmem++ = (255 * *pmem) / big;
                }
        }
}
#if (EX_COMPILE == TRUE)
/***********************************************************
        This function turns the grayscale display on and off
***********************************************************/ define GRAYW 32
define GRAYH 256
#define GRAYX 990
define GRAYY 112 gray_bar()
{
        void far *_fmalloc();
        int i, xpos, ypos, cols;
        static int onoff;
        unsigned char far *src, far *dst, far *xy_to_ad();
        static char far *mbuffer;

xpos = GRAYX;
        ypos = GRAYY;

if(onoff ^= 1)
        {
                if((dst = mbuffer = (char far *)_fmalloc(GRAYW * GRAYH)) == NULL)
                        exit();
                src = xy_to_ad(xpos, ypos);
                save_window(src, dst, GRAYW, GRAYH);

ypos = GRAYY;
                for(i = 0; i < 256; i++)
                {
                        cols = GRAYW;
                        src = xy_to_ad(xpos, ypos++);
                        while(cols--)
                                *src++ = i;
                }
        }
        else
        {
                src = mbuffer;
                dst = xy_to_ad(xpos, ypos);
                rec_window(src, dst, GRAYW, GRAYH);
                _ffree(mbuffer);
        }
}

/***********************************************************
        This function performs the level slicing function
***********************************************************/ slice()
{
        int i, j, x, y, x1, x2, y1, y2, y3, offset = 0, slope = 10;
        unsigned char far *ptable, far *data, far *xy_to_ad();
        char buf[32], top[64], bot[64], space[64];
        int xprint = XSLICEBX + (CHRW << 1), yprint = YSLICEBX + CHRH;
        static int upper = 100, lower = 100;
        static unsigned char far buffer[768];
        static struct genbox box = {XSLICEBX, YSLICEBX, 47, 3};
        struct genbox *bp;
        bp = &box;
```

```
                x1 = bp->xpos;
                x2 = x1 + (47 << 3);
                y1 = bp->ypos;
                y2 = y1 + CHRH;
                y3 = y2 + CHRH;

bot[0] = 200;
                top[0] = 201;
                space[0] = 186;
                for(i = 1; i < 47; i++)
                {
                        bot[i] = top[i] = 205;
                        space[i] = 32;
                }
                bot[i] = 188;
                top[i] = 187;
                space[i++] = 186;
                bot[i] = top[i] = space[i] = '\0';

open_box(bp);
                print_8x16(top, x1, y1, upper, 0);
                print_8x16(space, x1, y2, upper, 0);
                print_8x16(bot, x1, y3, upper, 0);
                sprintf(buf, "%3d - %3d  ", lower, upper);
                print_8x16(buf, xprint, yprint, upper, 0);
                                case F2_KEY:
                                case F3_KEY:
                                case F4_KEY:
                                case F5_KEY:
                                case F6_KEY:
                                case F7_KEY:
                                case F8_KEY:
                                case F9_KEY:
                                        display_flag = 1;
                                        j = (maxcontrast + mincontrast >> 1) -
(i - F1_KEY << 9);
                                        maxcontrast -= j;
                                        mincontrast -= j;
                                        break;
                                case SHFT_F1:
                                        disp_full_screen();
                                        break;
                                case '\r':
                                case ESC_KEY:
                                        close_box(bp);
                                        close_box(ib);
                                        free((void *)graybuf);
                                        crt_mode = oldmode;
                                        return;
                                        break;
                        }
                        x = xstart;
                        for (i = 0, pgraybuf = graybuf; i < 256; i++)
                                wr_px_xy(x++, ystart - *pgraybuf++,
BGDI);
                        maxmin = maxcontrast - mincontrast;
                        x = xstart;
                        for(i = 0, pgraybuf = graybuf, pgraybar =
graybar; i < 256; i++)
                        {
                                j = (((i << 4) - mincontrast) * 63L) /
maxmin;
                                if(j > 63) j = 63;
                                if(j < 0) j = 0;
                                *pgraybuf = (invert_flag) ? ~j & 0x3F :
j;
                                *pgraybar++ = *pgraybuf << 2;
                                wr_px_xy(x++, ystart - *pgraybuf++,
HISTI);
                        }
                        i = y;
```

```c
                        j = 8;
                        while(j--)
                                mem_to_mem((char far *)graybar,
xy_to_ad(xstart, i++), 256);
                        i = y + 9;
                        j = 4;
                        while(j--)
                        {
                                wr_px_xy(xstart + mintick, i, BGDI);
                                wr_px_xy(xstart + maxtick, i++, BGDI);
                        }
                        maxtick = ((maxcontrast > 4094) ? 4095 :
maxcontrast) >> 4;
                        mintick = ((mincontrast < 1) ? 0 : mincontrast)
 >> 4;
                        i = y + 9;
                        j = 4;
                        while(j--)
                        {
                                wr_px_xy(xstart + mintick, i, HISTI);
                                wr_px_xy(xstart + maxtick, i++, HISTI);
                        }
                }
                if(display_flag)
                {
                        display_image(fin_filespec, mincontrast,
maxcontrast);
                        display_flag = k = 0;
                        i = readkey();
                        while(readkey()) k++;
                        if(i && k < 2) ungetch(i);
                        k = (k < 8) ? 1 : 2;
                }
        }
}
/****************************************************************
        This function implements a 3 X 3 convolution filter
                The filters implemented are:
                        HIPASS          Dx
                        LOPASS          Dy
                        AVERAGE
                        LAPLACE
****************************************************************/

/*
Tony Scandura              07/18/85           04/10/90
*/ include <stdio.h>
include "ccd.h"
#include "keys.h"

#define XRESTOREBX 208
define YRESTOREBX 432 extern char *tmp_filespec;
convolve(cp)
struct curwindow *cp;
{
        int menupt;
        static struct menwindow menu =
        {
                14, 8, " - Filter -", "F1: Lopass", "F2: Hipass", "F3: Average",
                "F4: Laplace", "F5: Edge", "F6: Restore", "F7: Main Menu"
        };
        struct menwindow *wp;

wp = &menu;
```

```c
        sav_image(tmp_filespec);

while(1)
        {
                switch(menupt = get_menu_ptr(wp, TRUE, FALSE))
                {
                case 0:
                case 1:
                case 2:
                case 3:
                        conv3x3(cp, menupt);
                        break;
                case 4:
                        edge_filter(cp);
                        break;
                case 5:
                        rec_image(tmp_filespec);
                        break;
                case 6:
                case 7:
                        return;
                        break;
                }
        }
} edge_filter(cp)
struct curwindow *cp;
{
        int menupt;

static struct menwindow menu =
        {
                17, 10, " - Edge Filter -", "F1: Sobel", "F2: Edge",
"F3: Ripple",
                "F4: Line", "F5: Point", "F6: Edge Subspace", "F7: Line
Subspace",
                "F8: Restore", "F9: Previous Menu"
        };
        struct menwindow *wp;

wp = &menu;

while(1)
        {
                switch(menupt = get_menu_ptr(wp, TRUE, FALSE))
                {
                case 0:
                case 1:
                case 2:
                case 3:
                case 4:
                case 5:
                case 6:
                        conv3x3(cp, menupt + 4);
                        break;
                case 7:
                        rec_image(tmp_filespec);
                        break;
                case 8:
                case 9:
                        return;
                        break;
                }
        }
} conv3x3(cp, nfilter)
struct curwindow *cp;
int nfilter;
```

```
{
        void *malloc();
        unsigned char far *p, far *pp, far *xy_to_ad();
        unsigned char *s, *t, last, *pm;
        int new, xpos, ypos, xstart, ystart, xwidth, rows;
        int l, n, cols;

if((s = t = (unsigned char *)malloc(BINSIZE << 1)) == NULL)
        {
                pr_error(5);
                return(ERROR);
        }
        t += BINSIZE;
        xstart = xpos = (cp->xpos < cp->xpos1) ? cp->xpos : cp->xpos1;
        xwidth = cols = abs(cp->xpos - cp->xpos1) + 1;
        ystart = ypos = (cp->ypos < cp->ypos1) ? cp->ypos : cp->ypos1;
        rows = abs(cp->ypos - cp->ypos1) + 1;
        p = xy_to_ad(xpos, ypos++);
        pm = s;
        n = cols;
        while(n--)
                *pm++ = *p++;

l = rows - 2;
        while(l--)
        {
                pp = xy_to_ad(xpos, ++ypos);
                for(n = 0; n < cols; n++)
                        *(t + n) = *pp++;
                pp = t;
                p = xy_to_ad(xpos, --ypos);
                ++ypos;
                last = *p++;
                pm = s;

n = cols-2;
                while(n--)
                {
                        switch(nfilter)
                        {
                        case 1: /* HIPASS */
                                new = 9 * p[0] - last - p[1]
                                        - pm[0] - pm[1] - pm[2]
                                        - pp[0] - pp[1] - pp[2];
                                break;

case 2: /* AVERAGE */
                                new = (p[0] + last + p[1]
                                        + pm[0] + pm[1] + pm[2]
                                        + pp[0] + pp[1] + pp[2]) / 9;
                                break;

case 0: /* LOPASS */
                                new = ((p[0] << 2) + (last << 1) + (p[1]
<< 1)
                                        + pm[0] + (pm[1] << 1) + pm[2]
                                        + pp[0] + (pp[1] << 1) + pp[2])
>> 4;
                                break;

case 3: /* LAPLACE */
                                new = ((p[0] << 3) - last - p[1]
                                        - pm[0] - pm[1] - pm[2]
                                        - pp[0] - pp[1] - pp[2]) << 1;
                                break;

case 4: /* SOBEL */
                                new = abs(-pm[0] - (pm[1] << 1) - pm[2]
                                                + pp[0] + (pp[1] << 1) +
pp[2])
```

```
(last << 1)

pm[2]

>> 7) - pp[2])

(p[1] * 181 >> 7)

pp[1])

- pm[1]

>> 7));

2) - (p[1] << 1)

pm[2])

pm[1] - (pm[2] << 1)

p[1]

(pp[2] << 1));

pm[2]

>> 7) - pp[2])

(p[1] * 181 >> 7)

181 >> 7)

pp[1])

- pm[1]

>> 7));
```

```
                            + abs((p[1] << 1) -

- pm[0] + pm[2]
                            - pp[0] + pp[2]);
                    break;

case 5: /* EDGE */
                    new = abs(pm[0] + (pm[1] * 181 >> 7) +

- pp[0] - (pp[1] * 181

+ abs(pm[0] - pm[2]
                            + (last * 181 >> 7) -

+ pp[0] - pp[2]);
                    break;

case 6: /* RIPPLE */
                    new = abs(-pm[1] + (pm[2] * 181 >> 7)
                            + last - p[1]
                            - (pp[0] * 181 >> 7) +

+ abs((pm[0] * 181 >> 7)

- last + p[1]
                            + pp[1] - (pp[2] * 181 break;

case 7: /* LINE */
                    new = abs(pm[1]

- last - p[1]
                            + pp[1])
                            + abs(-pm[0] + pm[2]
                            + pp[0] - pp[2]);
                    break;

case 8: /* POINT */
                    new = abs(pm[0] - (pm[1] << 1) + pm[2]
                            - (last << 1) + (p[0] <<

+ pp[0] - (pp[1] << 1) +

+ abs(-(pm[0] << 1) +

+ last + (p[0] << 2) +

- (pp[0] << 1) + pp[1] - break;

case 9: /* EDGE SUBSPACE */
                    new = abs(pm[0] + (pm[1] * 181 >> 7) +

- pp[0] - (pp[1] * 181

+ abs(pm[0] - pm[2]
                            + (last * 181 >> 7) -

+ pp[0] - pp[2])
                            + abs(-pm[1] + (pm[2] *

+ last - p[1]
                            - (pp[0] * 181 >> 7) +

+ abs((pm[0] * 181 >> 7)

- last + p[1]
                            + pp[1] - (pp[2] * 181 break;
```

```
                    case 10:         /* LINE SUBSPACE */
                        new = abs(pm[1]
                                        - last - p[1]
                                        + pp[1])
                                        + abs(-pm[0] + pm[2]
                                        + pp[0] - pp[2])
                                        + abs(pm[0] - (pm[1] <<
1) + pm[2]
                                        - (last << 1) + (p[0] <<
2) - (p[1] << 1)
                                        + pp[0] - (pp[1] << 1) +
pm[2])
                                        + abs(-(pm[0] << 1) +
pm[1] - (pm[2] << 1)
                                        + last + (p[0] << 2) +
p[1]
                                        - (pp[0] << 1) + pp[1] -
(pp[2] << 1));
                        break;
                }
                *pm++ = last;
                last = *p;
                if(new < 0) new = 0;
                if(new > 0xff) new = 0xff;
                *p++ = new;
                pp++;
            }
            pm[0] = last;
            pm[1] = *p++;
        }
        free((void *)s);
}
restore_image()
{
        int i, xprint = XRESTOREBX + (CHRW << 1), yprint = YRESTOREBX +
CHRH;
        static struct genbox box = {XRESTOREBX, YRESTOREBX, 28, 3};
        struct genbox *bp;
        bp = &box;

open_box(bp);
        print_8x16("Restore Original Image ?", xprint, yprint, FGDI,
BGDI);
        i = get_key();
        close_box(bp);
        return(i);
}
/*************************************************
        This function delays for the specified number of
        one millisecond intervals
*************************************************/ delay(i)
int i;
{
        int onemilli = 1245;         /* counter for 1 ms delay */
        int j;                       /* 126 = 6MHz, 179 =
8MHz, 395 = 12MHz */
                                     /* 1245 = 33MHz */
        while (i--)
        {
                for (j = 0; j < onemilli; j++);
        }
}
/*************************************************
        These functions control the disk services for
        the VGA display adapter in graphics mode
*************************************************/

/*
```

Tony Scandura    04/13/90
*/

```c
#include <stdio.h>
include <dos.h>
#include <fcntl.h>
#include <sys\types.h>
#include <sys\stat.h>
#include "trident.h"
#include "ccd.h"
#include "keys.h"

#define XFSPECBOX XMID - 188
#define YFSPECBOX YMID - 224
#define XERRORBOX XMID - 116
define YERRORBOX YMID - 64 char df_path[64] = "c:\\images\\ford", df_ext[16] = ".img";
static int xerr = XERRORBOX + (CHRW << 1), yerr = YERRORBOX + CHRH;
static int xfspec = XFSPECBOX + (CHRW << 1), yfspec = YFSPECBOX + CHRH;
static struct genbox fspec_box = {XFSPECBOX, YFSPECBOX, 47, 8};
static struct genbox error_box = {XERRORBOX, YERRORBOX, 29, 7};
extern char *fin_filespec;
extern int mincontrast, maxcontrast, crt_mode;

disk_io(ext_flag)
int ext_flag;
{
        int i;
        char buf[64];
        char *filespec, *gr_gets(), *strcat(), *strcpy();
        char *get_filespec(), *get_smfilespec(), *search_filespec();

static struct menwindow menu =
        {
                19, 6, " -- Disk  Menu --", "F1: Recall An Image",
                "F2: Disk Directory", "F3: Save An Image", "F4: Delete A File",
                "F5: - Main  Menu -"
        };
        static struct menwindow ext_menu =
        {
                19, 10, " -- Disk  Menu --", "F1: Recall An Image",
                "F2: Disk Directory", "F3: Save An Image", "F4: Delete A File",
                "F5: Change Dir Path", "F6: Recall Screen", "F7: Save 8CRT Whole",
                "F8: Save 8CRT Image","F9: - Main  Menu -"
        };
        struct menwindow *wp;
        struct genbox *bp;

bp = &fspec_box;
        wp = (ext_flag) ? &ext_menu : &menu;

while(1)
        {
                switch(i = get_menu_ptr(wp, TRUE, FALSE))
                {
                case 0:
                        rec_it(ext_flag);
                        break;
                case 1:
                        get_dir(strcat(strcpy(buf, df_path), "\\*.img"));
                        break;
                case 2:
                        save_it(fin_filespec, ext_flag);
                        break;
```

```c
                case 3:
                        open_box(bp);
                        print_8x16("File Deletion:", xfspec, yfspec,
FGDI, BGDI);
                        filespec = (ext_flag) ?
                                        get_filespec(buf,
xfspec, yfspec + (CHRH << 1)) :
                                        get_smfilespec(buf,
xfspec, yfspec + (CHRH << 1));
                        close_box(bp);
                        if(*filespec != '.')
                                (unlink(filespec)) ? pr_error(1) :
del_annotation(filespec);
                        break;
                }
                if(ext_flag)
                switch(i)
                {
                case 4:
                        open_box(bp);
                        print_8x16("Change Default Path:", xfspec,
yfspec, FGDI, BGDI);
                        sprintf(buf, "Default Path = %s", df_path);
                        print_8x16(buf, xfspec + (6 << 3), yfspec +
(CHRH<<1), FGDI, BGDI);
                        sprintf(buf, "Default Ext  = %s", df_ext);
                        print_8x16(buf, xfspec + (6 << 3), yfspec + CHRH
* 3, FGDI, BGDI);
                        print_8x16("Enter New Default Path: ",
                                        xfspec, yfspec + CHRH *
5, FGDI, BGDI);
                        sscanf(gr_gets(buf, xfspec + (24 << 3), yfspec +
CHRH * 5, 20),
                                        "%s", df_path);
                        close_box(bp);
                        break;
                case 5:
                        open_box(bp);
                        print_8x16("Image Recall:", xfspec, yfspec,
FGDI, BGDI);
                        filespec = get_filespec(buf, xfspec, yfspec +
(CHRH << 1));
                        close_box(bp);
                        if(*filespec == '.')
                                break;
                        rec_image(filespec);
                        break;
                case 6:
                case 7:
                        open_box(bp);
                        print_8x16("Image Save:", xfspec, yfspec, FGDI,
BGDI);
                        filespec = get_filespec(buf, xfspec, yfspec +
(CHRH << 1));
                        close_box(bp);
                        if(*filespec == '.')
                                break;
                        if(exist_file(filespec) != ERROR)
                                (i == 6) ? sav_image(filespec) :
sav_only_image(filespec);
                        break;
                case 8:
                        return;
                        break;
                }
                else if(i == 4)
                        return;
        }
}
```

```
rec_it(ext_flag)
int ext_flag;
{
        char *filespec, *get_filespec(), *get_smfilespec(), *strrchr();
        char buf[64], *pchr;
        struct genbox *bp;
        int oldcrtmode;

bp = &fspec_box;
        open_box(bp);
        print_8x16("Image Recall:", xfspec, yfspec, FGDI, BGDI);
        filespec = (ext_flag) ?
                                        get_filespec(buf, xfspec, yfspec
+ (CHRH << 1)) :
                                        search_filespec(buf, xfspec,
yfspec + (CHRH << 1));
        close_box(bp);
        if(*filespec == '.')
                return;
        if(copy_image(filespec, fin_filespec) != ERROR)
        {
                dup_image();
                (rec_annotation(filespec)) ?
                        display_fullgry(fin_filespec) :
                        display_image(fin_filespec, mincontrast,
maxcontrast);
        }
        pchr = strrchr(filespec, '\\');
        if(*(pchr + 1) == '_' && *(pchr + 2) == 'S')
        {
                *(pchr + 2) = 'T';
                if(copy_image(filespec, fin_filespec) != ERROR)
                {
                        oldcrtmode = crt_mode;
                        crt_mode = 1;
                        dup_image();
                        display_image(fin_filespec, mincontrast,
maxcontrast);
                        rec_stereo(filespec);
                        pr_stereo_result();
                        crt_mode = oldcrtmode;
                }
        }
} save_it(src_fspec, ext_flag)
char *src_fspec;
int ext_flag;
{
        char *filespec, *get_filespec(), *get_smfilespec(), buf[64];
        struct genbox *bp;

bp = &fspec_box;
        open_box(bp);
        print_8x16("Image Save:", xfspec, yfspec, FGDI, BGDI);
        filespec = (ext_flag) ? get_filespec(buf, xfspec, yfspec + (CHRH
<< 1)) :
                                        get_smfilespec(buf,
xfspec, yfspec + (CHRH << 1));
        close_box(bp);
        if(*filespec == '.')
                return;
        if(exist_file(filespec) != ERROR)
                if(copy_image(src_fspec, filespec) != ERROR)
                        save_annotation(filespec);
} auto_save_it()
{
        static int i;
        char filespec[64], *get_new_name();
```

```c
        if(exist_file(get_new_name(filespec)) != ERROR)
                if(copy_image(f:n_filespec, filespec) != ERROR)
                        save_annotation(filespec);
} char *get_new_name(buffer)
char *buffer;
{
        static int i;
        char date[9], buf[64];

_strdate(date);
        do
        {
                sprintf(buffer, "%s\\%c%c%c%c%d%s",
                                df_path, date[0], date[1], date[3],
date[4], i, df_ext);
                sprintf(buf, "%s\\_S%c%c%d%s",
                                df_path, date[3], date[4], i, df_ext);
                if(i++ > 9999) break;
        }
        while(!access(buffer, 0) || !access(buf, 0));
        return(buffer);
}

/*******************************************************
        This function displays the specified directory
********************************************************/

/*
        Tony Scandura    07/16/86
*/ define MAXFILES 360 get_dir(pathname)
char *pathname;
{
        union REGS inregs, outregs;
        static char dta[128];
        char buf[32];
        int ret_code, nfiles, x = 0, y = 0;
        extern char *tmp_filespec;

sav_image(tmp_filespec);

nfiles = 1;
        reset_vid_mode();

inregs.h.ah = 0x1a;
        inregs.x.dx = (unsigned)dta;
        ret_code = intdos(&inregs, &outregs);
        inregs.h.ah = 0x4e;
        inregs.x.dx = (unsigned int)pathname;
        inregs.x.cx = 0;
        if(ret_code = intdos(&inregs, &outregs))
        {
                switch(ret_code)
                {
                        case 2:
                        case 18:
                                pr_error(8);
                                break;
                        default:
                                pr_error(9);
                                break;
                }
                rec_image(tmp_filespec);
                return;
        }
```

```c
        else
        {
                print_8x16(dta + 30, x, y, FGDI, BGDI);
                nfiles++;
        } do
        {
                x += 128;
                if(x == BYTESPERLINE)
                        x = 0, y += 16;
                inregs.h.ah = 0x4f;
                ret_code = intdos(&inregs, &outregs);
                if(!ret_code)
                {
                        print_8x16(dta + 30, x, y, FGDI, BGDI);
                        nfiles++;
                }
                if(nfiles > MAXFILES)
                {
                print_8x16("*** Press any key to continue ***",
                                        XMID - 132, MAXVIDEOLINE - 16, FGDI, BGDI);
                        get_key();
                        nfiles = 1;
                        x = -128;
                        y = 0;
                        reset_vid_mode();
                }
        }
        while(!(ret_code));
        print_8x16("*** Press any key to continue ***",XMID -132, y += 48, FGDI, BGDI);
        get_key();
        rec_image(tmp_filespec);
}

/****************************************************
        Function to read screen images from the disk
****************************************************/

/*
Tony Scandura    8/1/89   3/13/90
*/ rec_image(filespec)
char *filespec;
{
        int fp, ret_code, bank;
        unsigned int nbytes = 0x8000;
        unsigned char far *pscreen, far *xy_to_ad();
        union REGS inregs, outregs;
        struct SREGS segregs;

inregs.h.ah = 0x3d;
        inregs.x.dx = (unsigned int)filespec;
        inregs.h.al = 0;
        fp = intdos(&inregs, &outregs);
        if (outregs.x.cflag)
        {
                pr_error(1);
                return(ERROR);
        } for(bank = 0; bank < 24; bank++)
        {
                pscreen = xy_to_ad(0, bank * 32);
                inregs.h.ah = 0x3f;
                inregs.x.bx = fp;
                inregs.x.cx = nbytes;
                inregs.x.dx = FP_OFF(pscreen);
```

```
            segregs.ds = FP_SEG(pscreen);
            ret_code = intdosx(&inregs, &outregs, &segregs);
            if (outregs.x.cflag)
            {
                    pr_error(2);
                    return(ERROR);
            }
    } inregs.h.ah = 0x3e;
    inregs.x.bx = fp;
    ret_code = intdos(&inregs, &outregs);
    if (outregs.x.cflag)
    {
            pr_error(3);
            return(ERROR);
    }
    return(0);
}
/*************************************************
        Function to save an screen image to disk
*************************************************/

/*
Tony Scandura    18/05/90
*/ sav_image(filespec)
char *filespec;
{
    int fp, ret_code, bank;
    unsigned int nbytes = 0x8000;
    unsigned char far *pscreen, far *xy_to_ad();
    union REGS inregs, outregs;
    struct SREGS segregs;

if ((fp = open(filespec, O_RDWR | O_CREAT | O_BINARY,
                    S_IREAD | S_IWRITE)) == ERROR)
    {
            pr_error(0);
            return(ERROR);
    } for (bank = 0; bank < 24; bank++)
    {
            pscreen = xy_to_ad(0, bank * 32);
            inregs.h.ah = 0x40;
            inregs.x.bx = fp;
            inregs.x.cx = nbytes;
            inregs.x.dx = FP_OFF(pscreen);
            segregs.ds = FP_SEG(pscreen);
            ret_code = intdosx(&inregs, &outregs, &segregs);
            if (outregs.x.cflag)
            {
                    pr_error(4);
                    return(ERROR);
            }
    } inregs.h.ah = 0x3e;
    inregs.x.bx = fp;
    ret_code = intdos(&inregs, &outregs);
    if (outregs.x.cflag)
    {
            pr_error(3);
            return(ERROR);
    }
    return(0);
}
```

```c
sav_only_image(filespec)
char *filespec;
{
        int fp, ret_code, y;
        unsigned int nbytes = BINSIZE;
        unsigned char far *pscreen, far *xy_to_ad();
        union REGS inregs, outregs;
        struct SREGS segregs;

if ((fp = open(filespec, O_RDWR | O_CREAT | O_BINARY,
                        S_IREAD | S_IWRITE)) == ERROR)
        {
                pr_error(0);
                return(ERROR);
        } for (y = YIMAGEBIN; y < YIMAGEBIN + BINSIZE; y++)
        {
                pscreen = xy_to_ad(0, y);
                inregs.h.ah = 0x40;
                inregs.x.bx = fp;
                inregs.x.cx = nbytes;
                inregs.x.dx = FP_OFF(pscreen);
                segregs.ds = FP_SEG(pscreen);
                ret_code = intdosx(&inregs, &outregs, &segregs);
                if (outregs.x.cflag)
                {
                        pr_error(4);
                        return(ERROR);
                }
        } inregs.h.ah = 0x3e;
        inregs.x.bx = fp;
        ret_code = intdos(&inregs, &outregs);
        if (outregs.x.cflag)
        {
                pr_error(3);
                return(ERROR);
        }
        return(0);
}

/********************************************************
        This function gets a filespec from the keyboard
        and returns a pointer to it
********************************************************/

/*
Tony Scandura    05-09-88            04-13-90
*/ char *get_filespec(buffer, xpos, ypos)
char *buffer;
int xpos, ypos;
{
        char filespec[64];
        char *pbuf, *gr_gets(), *strchr(), *strcat(), *strcpy();

sprintf(filespec, "Default Path = %s", df_path);
        print_8x16(filespec, xpos + (6 << 3), ypos, FGDI, BGDI);
        sprintf(filespec, "Default Ext  = %s", df_ext);
        print_8x16(filespec, xpos + (6 << 3), ypos += CHRH, FGDI, BGDI);
        print_8x16("Filespec ? ", xpos, ypos += CHRH << 1, FGDI, BGDI);

sprintf(filespec, "%s\\", df_path);
        pbuf = gr_gets(buffer, xpos + (11 << 3), ypos, 32);
        if(strchr(pbuf, '.') == NULL)
                strcat(pbuf, df_ext);
        if(*pbuf == '\\' || *(pbuf + 1) == ':' || *pbuf == '.')
                return(pbuf);
```

```
                strcat(filespec, pbuf);
                strcpy(buffer, filespec);
                return(buffer);
}

/************************************************************
        This function gets a filespec from the keyboard
        and returns a pointer to it
************************************************************/ char *get_smfilespec(buffer, xpos, ypos)
char *buffer;
int xpos, ypos;
{
        char filespec[64];
        char *pbuf, *gr_gets(), *strchr(), *strcat(), *strcpy();

print_8x16("Type Image Name, Then Press ENTER: ",
                                            xpos, ypos, FGDI, BGDI);
        print_8x16("--- OR ---", xpos + (16 << 3), ypos + CHRH + 8,
FGDI, BGDI);
        print_8x16("Press ENTER To Return To Disk Menu",
                                            xpos + (4 << 3), ypos +
CHRH * 3, FGDI, BGDI);
        sprintf(filespec, "%s\\", df_path);
        pbuf = gr_gets(buffer, xpos + (35 << 3), ypos, 8);
        if(strchr(pbuf, '.') == NULL)
                strcat(pbuf, df_ext);
        if(*pbuf == '\\' || *(pbuf + 1) == ':' || *pbuf == '.')
                return(pbuf);
        strcat(filespec, pbuf);
        strcpy(buffer, filespec);
        return(buffer);
} char *gr_gets(buffer, xpos, ypos, length)
char *buffer;
int xpos, ypos, length;
{
        int i, j;
        char pchar[2], boxes[64];

pchar[1] = '\0';
        for(i = 0; i < length; i++)
                boxes[i] = '\xfe';
        boxes[i] = '\0';
        print_8x16(boxes, xpos, ypos, FGDI, BGDI);
        i = 0;
        while((*pchar = get_key()) != '\r')
                if(*pchar == '\b')
                {
                        if(i)
                        {
                                print_8x16("\xfe", xpos -= CHRW, ypos,
FGDI, BGDI);
                                i--;
                        }
                }
                else
                {
                        if(i < length && *pchar > 31 && *pchar < 128)
                        {
                                print_8x16(pchar, xpos, ypos, FGDI,
BGDI);
                                xpos += CHRW;
                                *(buffer + i++)= *pchar;
                        }
                }
        *(buffer + i) = '\0';
        j = 0;
        while(i++ < length)
                boxes[j++] = ' ';
```

```
            boxes[j] = '\0';
            print_8x16(boxes, xpos, ypos, FGDI, BGDI);
            return(buffer);
}

/*******************************************************************
*****
        This function checks if a file exists and returns an error if it
does
*******************************************************************
****/

/*
Tony Scandura    04-16-90
*/ exist_file(filespec)
char *filespec;
{
        struct genbox *eb;
        eb = &error_box;

if(!access(filespec, 0))
        {
                open_box(eb);
                print_8x16("------W A R N I N G------", xerr, yerr,
FGDI, BGDI);
                print_8x16(" The File Already Exists",
                                                xerr, yerr + (CHRH <<
1), FGDI, BGDI);
                print_8x16(" Overwrite File ?   (y/n)",
                                                xerr, yerr + (CHRH <<
2), FGDI, BGDI);
                if(get_key() != 'y')
                {
                        close_box(eb);
                        return(ERROR);
                }
                close_box(eb);
        }
        return(0);
} pr_error(errornum)
int errornum;
{
        struct genbox *eb;
        static char *error_msg[] =
        {
                "The File Cannot Be Opened",
                "The File Does Not Exist !",
                "Errors While Reading File",
                "Errors While Closing File",
                "Error While Writting File",
                " Not  Enough  Memory !",
                "There Is No Image To Save",
                "    There Is No Image",
                "   No Files Were Found",
                " The Path Does Not Exist",
                "Error While Making D-base",
                "WARNING: Optics distorted"
        };

eb = &error_box;
        open_box(eb);
        print_8x16("------- E R R O R -------", xerr, yerr, FGDI, BGDI);
        print_8x16(error_msg[errornum], xerr, yerr + (CHRH << 1), FGDI,
BGDI);
        print_8x16("Press ANY Key To Continue",
                                                xerr, yerr + (CHRH <<
```

```
2), FGDI, BGDI);
        get_key();
        close_box(eb);
}
/****************************************************************
        These functions output a luminance histogram to any of
        the following: the CRT, the line printer, or a Lotus File.
****************************************************************/

/*
        Tony Scandura    04-02-86        11-18-8602-14-8904-07-89
                                         04-03-90
*/ include <stdio.h>
include <fcntl.h>
#include "ccd.h"
#include "keys.h"

#define CRT_SCALE 100
#define PRT_SCALE 50
#define MAXBINS 256
#define XHISTPOS (XIMAGEBIN + BINSIZE + 8)
#define YHISTPOS (YIMAGEBIN)
#define XFSPECBOX 324
#define YFSPECBOX 160
#define XERRORBOX 396
define YERRORBOX 320 histogram(cp)
struct curwindow *cp;
{
        int menupt;
        int out_device, factor = 0;
        static struct menwindow menu =
        {
                13, 8, "- # Of Bins -", "F1:    8", "F2:   16", "F3:   32",
"F4:   64",
                "F5:  128", "F6:  256", "F7: Main Menu"
        };
        struct menwindow *wp;

wp = &menu;
        if((out_device = get_outdevice()) != ERROR)
        {
                switch(menupt = get_menu_ptr(wp, TRUE, FALSE))
                {
                        case 0:
                        case 1:
                        case 2:
                        case 3:
                        case 4:
                        case 5:
                                factor = 5 - menupt;
                                break;
                        case 6:
                        case 7:
                                return;
                                break;
                }
                histgram(cp, out_device, factor);
        }
} histgram(cp, out_device, factor, onoff)
struct curwindow *cp;
int out_device, factor, onoff;
{
        FILE *stream;
        int i, x, y, bins, scale;
        int xstart, ystart, xwidth, cols, rows;
```

```c
        int xprint = XFSPECBOX + (CHRW << 1), yprint = YFSPECBOX + CHRH;
        unsigned char far *pmem, far *xy_to_ad();
        long big, histotal;
        static long hist[MAXBINS], phist[MAXBINS];
        char *get_filespec(), buf[64];
        static struct genbox box = {XHISTPOS, YHISTPOS, 36, 11};
        static struct genbox fspec_box = {XFSPECBOX, YFSPECBOX, 47, 8};
        static struct genbox error_box = {XERRORBOX, YERRORBOX, 29, 7};
        struct genbox *bp, *eb, *fs;
        bp = &box;
        eb = &error_box;
        fs = &fspec_box;

if(! onoff)
        {
                close_box(bp);
                return;
        }
xstart = (cp->xpos < cp->xpos1) ? cp->xpos : cp->xpos1;
xwidth = abs(cp->xpos - cp->xpos1) + 1;
ystart = (cp->ypos < cp->ypos1) ? cp->ypos : cp->ypos1;
rows = abs(cp->ypos - cp->ypos1) + 1;

scale = (out_device) ? PRT_SCALE : CRT_SCALE;
bins = MAXBINS >> factor;

for (i = 0; i < bins; i++)
        hist[i] = 0;
while(rows--)
{
        pmem = xy_to_ad(xstart, ystart++);
        cols = xwidth;
        while(cols--)
        {
                i = *pmem++ >> factor;
                hist[i]++;
        }
}
for (i = 1, big = hist[0]; i < bins; i++)
        big = (big > hist[i]) ? big : hist[i];
for (i = 0, histotal = 0; i < bins; i++)
{
        histotal += hist[i];
        phist[i] = (scale * hist[i]) / big;
} switch(out_device)
{
        case 0:
                open_box(bp);
                xstart = x = XHISTPOS + (CHRW << 1);
                ystart = y = YHISTPOS + 122;
                for (i = 0; i < bins; i++)
                {
                        y = ystart;
                        while (phist[i]--)
                        {
                                pmem = xy_to_ad(x, y--);
                                *pmem = FGDI;
                        }
                        x++;
                }
                y = CHRH;
                ystart += 2;
                while(y--)
                {
                        pmem = xy_to_ad(xstart, ystart++);
                        for(i = 0; i < 256; i++)
                                *pmem++ = i;
                }
```

```
                ystart++;
                pmem = xy_to_ad(xstart, ystart++);
                for(i = 0; i < 256; i++)
                        *pmem++ = FGDI;
                y = 4;
                ystart++;
                while(y--)
                {
                        pmem = xy_to_ad(xstart, ystart++);
                        for(i = 0; i < 256; i++)
                                *pmem++ = (i % 32) ? BGDI :
FGDI;
                        *--pmem = FGDI;
                }
                ystart++;
                print_8x8("0   32   64   96   128  160  192  224  256",
                                        xstart - 3, ystart,
FGDI, BGDI);
/*
                get_key();
*/
                break;
        case 1:
                prheaders();
                for (i = 0; i < bins; i++)
                {
                        if(readkey() == ESC_KEY)
                        {
                                fprintf(stdprn, "\n\f");
                                break;
                        }
                        x = i << factor;
                        fprintf(stdprn, "%8li%5d to %3d ",
                                        hist[i], x, x - 1 + (1
<< factor));
                        x = (int)(scale - phist[i]);
                        while(phist[i]--)
                        fprintf(stdprn, "%c", 254);
                        pspace(x);
                        fprintf(stdprn, "  %7.2f", hist[i] *
100.0 / histotal);
                        fprintf(stdprn, "\n");
                }
                fprintf(stdprn, "\n\n");
                fprintf(stdprn, "%8ld Total Bytes\n\f",
histotal);
                fflush(stdprn);
                break;
        case 2:
                x = XERRORBOX + (CHRW << 1);
                y = YERRORBOX + CHRH;
                open_box(fs);
                print_8x16("Enter Filespec For Lotus File:",
                                        xprint, yprint, FGDI,
BGDI);
                if((stream = fopen(get_filespec(buf, xprint,
yprint + (CHRH << 1)),
                                        "w")) == NULL)
                {
                        open_box(eb);
                        print_8x16("------- E R R O R -------",
x, y, FGDI, BGDI);
                        print_8x16("The File Cannot Be Opened",
                                        x, y += CHRH << 1, FGDI,
BGDI);
                        print_8x16("Press ANY Key To Continue",
                                        x, y += CHRH << 1, FGDI,
BGDI);
                        get_key();
                        close_box(eb);
                        close_box(fs);
```

```c
                              break;
                }
                close_box(fs);
                fprintf(stream, "\"Range\" \"\" \"Number\"\n");
                for (i = 0; i < bins; i++)
                {
                        x = i << factor;
                        fprintf(stream, "%d %d %li\n",
                                          x, x - 1 + (1 <<
factor), hist[i]);
                }
                fprintf(stream, "\"Tot Bytes\" \"\" %ld\n",
histotal);
                fclose(stream);
                break;
        }
} prheaders()
{
        int i;

pspace(23);
        fprintf(stdprn, "L U M I N A N C E    H I S T O G R A
M\n\n\n\n\n");
        pspace(39);
        fprintf(stdprn, "Relative Percent\n");
        pspace(3);
        fprintf(stdprn, "# Of       Range");
        pspace(57);
        fprintf(stdprn, "%% Of\n");
        fprintf(stdprn, "Occurances  Of Data   ");
        for (i = 10; i < 101; i += 10)
                fprintf(stdprn, " %3d", i);
        fprintf(stdprn, "  Total\n");
        pspace(21);
        for (i = 1; i < 51; i++)
                (i % 5) ? fprintf(stdprn, "%c", 196) : fprintf(stdprn,
"%c", 193);
        fprintf(stdprn, "\n");
} pspace(number)
int number;
{
        while(number--)
                fprintf(stdprn, " ");
} get_outdevice()
{
        int menupt;
        static struct menwindow menu =
        {
                18, 9, "- Out Device -", "  CRT", " Printer", " Lotus
File",
                " Main  Menu"
        };
        struct menwindow *wp;

wp = &menu;
        switch(menupt = get_menu_ptr(wp, TRUE, FALSE))
        {
                case 0:
                case 1:
                case 2:
                        return(menupt);
                        break;
                case 3:
                case 4:
                        return(ERROR);
                        break;
```

```
        }
}
/*****************************************************
******************************************************/

/*
Tony Scandura   11/07/91
*/ include <stdio.h>
include <dos.h>
#include <fcntl.h>
#include <sys\types.h>
#include <sys\stat.h>
#include "trident.h"
#include "ccd.h"
#include "keys.h"

extern char df_path[], df_ext[];
char *dbase_fspec = "h:dirdata.dir";
static char dta[128], dir_buf[64];
static char *sav_fspec = "h:box";

make_dirdata()
{
        union REGS inregs, outregs;
        int fp;

if((fp = open(dbase_fspec, O_RDWR | O_CREAT | O_BINARY |
O_TRUNC,
                                                  S_IREAD | S_IWRITE)) ==
ERROR)
        {
                pr_error(0);
                return(ERROR);
        }
        inregs.h.ah = 0x1a;
        inregs.x.dx = (unsigned)dta;
        intdos(&inregs, &outregs);

sprintf(dir_buf, "%s%s", df_path, "\\*.dat");
        inregs.h.ah = 0x4e;
        inregs.x.dx = (unsigned int)dir_buf;
        inregs.x.cx = 0;
        if(intdos(&inregs, &outregs))
        {
                pr_error(10);
                close(fp);
                return(ERROR);
        }
        if(readdata(fp))
        {
                close(fp);
                return(ERROR);
        } inregs.h.ah = 0x4f;
        while(!intdos(&inregs, &outregs))
                if(readdata(fp))
                {
                        close(fp);
                        return(ERROR);
                }
        close(fp);
        return(0);
} readdata(fp)
int fp;
{
```

```
        FILE *stream;
        char buffer[64];
        int i;

sprintf(buffer, "%s\\%s", df_path, dta + 30);
        sscanf(dta + 30, "%[^.]", dir_buf + 41);
        if((stream = fopen(buffer, "r")) == NULL)
        {
                pr_error(10);
                return(ERROR);
        }
        fscanf(stream, "%s %s %*d %*f %*d %s %*s %d",
                dir_buf, dir_buf + 16, dir_buf + 32, &i);
        fclose(stream);
        write(fp, dir_buf, 50);
        return(0);
} char *search_filespec(buffer, xpos, ypos)
char *buffer;
int xpos, ypos;
{
        char buf[64], hits[256];
        char *pbuf, *gr_gets();
        int i, length, fp, x, y, revx, revylen;

*buffer = '.';
        y = (ypos -= 8);
        wr_8_box(sav_fspec, xpos, 44 * CHRW, ypos + CHRH * 7, 27 * CHRH);
        pbuf = buf;
        *pbuf++ = '\xc9';
        for(i = 1; i < 43; i++)
                *pbuf++ = '\xcd';
        *pbuf++ = '\xbb';
        *pbuf = '\0';
        xpos += 6 * CHRW;
        print_8x16("F1: Patient ID   :", xpos, ypos, FGDI, BGDI);
        print_8x16("F2: Patient Name:", xpos, ypos + CHRH, FGDI, BGDI);
        print_8x16("F3: Patient Date:", xpos, ypos + CHRH * 2, FGDI, BGDI);
        print_8x16("F4: Return To Main Menu", xpos, ypos + 8 + CHRH * 3, FGDI, BGDI);
        do
                if((i = get_key()) == ESC_KEY)
                        return(buffer);
        while(i < F1_KEY || i > F4_KEY);
        i -= F1_KEY;
        xpos += CHRW * 18;
        y += CHRH * i;
        switch(i)
        {
                case 0:
                        pbuf = dir_buf;
                        length = 15;
                        break;
                case 1:
                        pbuf = dir_buf + 16;
                        length = 15;
                        break;
                case 2:
                        pbuf = dir_buf + 32;
                        length = 8;
                        break;
                case 3:
                        return(buffer);
                        break;
        }
        gr_gets(buffer, xpos, y, length);
        if(i == 2)
```

```
                *(buffer + 2) = *(buffer + 5) = '/';

if((fp = open(dbase_fspec, O_RDWR | O_BINARY)) == ERROR)
        {
                pr_error(0);
                *buffer = '.';
                return(buffer);
        }
        xpos -= CHRW * 24;
        ypos += CHRH * 7;
        y = ypos - CHRH;
        length = x = 0;
        print_8x16(buf, xpos, y += CHRH, FGDI, BGDI);
        while(read(fp, dir_buf, 50))
                if(!strcmpi(buffer, pbuf))
                {
                        strcpy(hits + (length++ * 9), dir_buf + 41);
                        sprintf(buf,"\xba %-16s%-16s%-8s \xba",
                                        dir_buf, dir_buf + 16,
dir_buf + 32);
                        print_8x16(buf, xpos, y += CHRH, FGDI, BGDI);
                        if(length > 26) break;
                }
        pbuf = buf;
        *pbuf++ = '\xc8';
        for(i = 1; i < 43; i++)
                *pbuf++ = '\xcd';
        *pbuf++ = '\xbc';
        *pbuf = '\0';
        print_8x16(buf, xpos, y += CHRH, FGDI, BGDI);
        y = ypos + CHRH;
        revx = xpos + 14;
        revylen = 40 * CHRW + 4;
        if(length--)
        {
                rev_fgd_bkgd(revx, y, FGDI, BGDI, revylen, CHRH);
                while((i = get_key()) != '\r')
                {
                        switch(i)
                        {
                                case UP_ARROW:
                                case RIGHT_ARROW:
                                        if(x)
                                        {
                                                x--;
                                                y -= CHRH;
                                                rev_fgd_bkgd(revx, y,
FGDI, BGDI, revylen, 32);
                                        }
                                        break;
                                case DOWN_ARROW:
                                case LEFT_ARROW:
                                        if(x < length)
                                        {
                                                x++;
                                                rev_fgd_bkgd(revx, y,
FGDI, BGDI, revylen, 32);
                                                y += CHRH;
                                        }
                                        break;
                                case F4_KEY:
                                case ESC_KEY:
                        rd_8_box(sav_fspec, xpos, 44 * CHRW, ypos,
(length + 3) * CHRH);
                                        *buffer = '.';
                                        return(buffer);
                                        break;
                        }
                }
                sprintf(buffer, "%s\\%s%s", df_path, hits + (x * 9),
```

```
                df_ext);
        }
        rd_8_box(sav_fspec, xpos, 44 * CHRW, ypos, (length + 3) * CHRH);
        return(buffer);
} wr_8_box(fspec, x, xlen, y, ylen)
char *fspec;
int x, xlen, y, ylen;
{
        int linelen, fp;
        unsigned char far *pscreen, far *xy_to_ad();
        union REGS inregs, outregs;
        struct SREGS segregs;

if((fp = open(fspec, O_RDWR | O_BINARY | O_CREAT | O_TRUNC,
                                        S_IREAD | S_IWRITE)) ==
ERROR)
        {
                pr_error(0);
                return(ERROR);
        } while(ylen--)
        {
                pscreen = xy_to_ad(x, y++);
                inregs.h.ah = 0x40;
                inregs.x.bx = fp;
                inregs.x.cx = xlen;
                inregs.x.dx = FP_OFF(pscreen);
                segregs.ds = FP_SEG(pscreen);
                intdosx(&inregs, &outregs, &segregs);
                if (outregs.x.cflag)
                {
                        pr_error(4);
                        return(ERROR);
                }
        } inregs.h.ah = 0x3e;
        inregs.x.bx = fp;
        intdos(&inregs, &outregs);
        if (outregs.x.cflag)
        {
                pr_error(3);
                return(ERROR);
        }
        return(0);
} rd_8_box(fspec, x, xlen, y, ylen)
char *fspec;
int x, xlen, y, ylen;
{
        int linelen, fp;
        unsigned char far *pscreen, far *xy_to_ad();
        union REGS inregs, outregs;
        struct SREGS segregs;

if((fp = open(fspec, O_RDWR | O_BINARY)) == ERROR)
        {
                pr_error(0);
                return(ERROR);
        } while(ylen--)
        {
                pscreen = xy_to_ad(x, y++);
                inregs.h.ah = 0x3f;
                inregs.x.bx = fp;
```

```
                inregs.x.cx = xlen;
                inregs.x.dx = FP_OFF(pscreen);
                segregs.ds = FP_SEG(pscreen);
                intdosx(&inregs, &outregs, &segregs);
                if (outregs.x.cflag)
                {
                        pr_error(2);
                        return(ERROR);
                }
        } inregs.h.ah = 0x3e;
        inregs.x.bx = fp;
        intdos(&inregs, &outregs);
        if (outregs.x.cflag)
        {
                pr_error(3);
                return(ERROR);
        }
        return(0);
}
/************************************************************
        This function controls integrating the CCD camera and
        and capturing and displaying the integrated image
************************************************************/

/*
Tony Scandura    03/16/90
*/ include <stdio.h>
include <fcntl.h>
#include <sys\types.h>
#include <sys\stat.h>
#include "ccd.h"
#include "keys.h"
#include "trident.h"

#define FOCUSLINES (128)
#define HST_CONT_MIN (8)
#define HST_THRESHOLD (25)
#define XWAITPOS (XMID - 236)
#define YWAITPOS (160)
#define EXTRACHRS (18)
#define MAXDATA (4096)
#define MAXGREY (255)
#define XDISPRNGPOS (XIMAGEBIN + 216)
#define YDISPRNGPOS (YIMAGEBIN + BINSIZE + 8)
#define XZOOMPOS (XIMAGEBIN + 216)
#define YZOOMPOS (YIMAGEBIN + BINSIZE + 80)
#define DARKOFFSET 50
define TOPBORDER 128 int maxwhite, maximage, minimage, maxdisplay, mindisplay;
int bin_mode = BINNED_M, crt_mode = 0, disp_mode = SPLIT_M, stereo_mode;
extern int xmenu, ymenu, maxcontrast, mincontrast, invert_flag;
extern unsigned histdata[];
extern struct curwindow altcursor;
extern struct menwindow quit_menu;
extern struct genbox instbox;
extern char *fin_filespec, *tmp_filespec, *wht_filespec, *drk_filespec;
extern char *hf_wht_fspec, *hb_wht_fspec, *hf_drk_fspec, *hb_drk_fspec;
extern char *cnf_filespec;
static int int_time = 100, stst_method = 1, crtbitshft = 4, int_formula
= 2;
static int out_amp = LOWER_AMP, zoomflag;
static char *ststresponses[] = {"Entered Int Time ", "External On
X-Ray",
                                                        "X-Ray & Int Time "};
static char *formresponses[] = {"I            ", "I - D
",
                                                "I / W            ", "(I
```

```c
    - D) / (W - D)"};
static char *outresponses[] = {"Lower Amp Only", "Upper Amp Only",
                                                 "Upper & Lower "};
static char *binresponses[] = {"Full Resolution", "Bin To 512      "};
static char *dispresponses[] = {"Single Image", "Side By Side"};
static char *steresponses[] = {"Stereo Mode OFF", "Stereo Mode ON "};
static int ststmax = 3, formmax = 4, outampmax = 12;

integrate(cp)
struct curwindow *cp;
{
        int i, lines;
        char buffer[35], *gr_gets();
        static struct menwindow menu =
        {
                17, 10, "-Integrate  Menu-", "F1: Acquire Image",
                "F2: Acquire Raw", "F3: Focus Cycle", "F4: Set
Defaults",
                "F5: Make Files", "F6: Clear System", "F7: Move Menu",
                "F8: Disk Services", "F9: Main  Menu"
        };
        static struct genbox box = {XINSTPOS, YINSTPOS, 36, 3};
        struct menwindow *wp;
        struct curwindow *altcp;
        struct genbox *ip = &box;

wp = &menu;
        altcp = &altcursor;

while(1)
        {
                switch(get_menu_ptr(wp, TRUE, FALSE))
                {
                case 0:
                        if((i = int_image(fin_filespec)) != ERROR)
                        {
                                open_box(ip);
                                sprintf(buffer, "Integration Time:%5d
millisecs", i);
                                print_8x16(buffer, XINSTPOS + 16,
YINSTPOS + 16, FGDI, BGDI);
                                delay(2000);
                                close_box(ip);
                        }
                        break;
                case 1:
                        if((i = int_raw(fin_filespec)) != ERROR)
                        {
                                open_box(ip);
                                sprintf(buffer, "Integration Time:%5d
millisecs", i);
                                print_8x16(buffer, XINSTPOS + 16,
YINSTPOS + 16, FGDI, BGDI);
                                delay(2000);
                                close_box(ip);
                        }
                        break;
                case 2:
                        reset_vid_mode();
                        set_display_bits(FALSE);
                        print_8x16("Enter Number Of Lines : ",
                                                XMID - 104, YMID, FGDI,
BGDI);
                        sscanf(gr_gets(buffer, XMID + 80, YMID, 4),"%d",
&lines);
                        print_8x16("Enter Integration time: ",
                                                XMID - 104, YMID + CHRH,
FGDI, FGDI);
                        sscanf(gr_gets(buffer, XMID + 80, YMID + CHRH,
5),"%d", &int_time);
```

```c
                        cycle(lines);
                        reset_vid_mode();
                        break;
                case 3:
                        set_parameters();
                        break;
                case 4:
                        make_files();
                        break;
                case 5:
                        reset_vid_mode();
                        break;
                case 6:
                        move_menu(altcp);
                        break;
                case 7:
                        disk_io(1);
                        break;
                case 8:
                        return;
                        break;
                }
        }
} int_raw(filespec)
char *filespec;
{
        int old_formula, i;

old_formula = int_formula;
        int_formula = 0;
        i = int_image(filespec);
        int_formula = old_formula;
        return(i);
} int_image(filespec)
char *filespec;
{
        void *malloc(), *calloc();
        int i = 0, lines, fpf, fpw, fpd;
        unsigned int nrdbytes, nwrbytes;
        int *lower, *upper, *wbuf, *dbuf, big = 0, small = 4096;
        unsigned long *hist;
        static struct genbox box = {XWAITPOS, YWAITPOS, 59, 5};
        for (i = 0; i < 256; i++, x++)
        {
                j = y;
                k = (histdata[i] > 160) ? 160 : histdata[i];
                while (k--)
                {
                        pcrt = xy_to_ad(x, j--);
                        *pcrt = HISTI;
                }
        } y += 2;
        pcrt = xy_to_ad(xstart, y++);
        for(i = 0; i < 256; i++)
                *pcrt++ = HISTI;
        j = 4;
        y++;
        while(j--)
        {
                pcrt = xy_to_ad(xstart, y++);
                for(i = 0; i < 256; i++)
                        *pcrt++ = (i % 32) ? BGDI : HISTI;
                *--pcrt = HISTI;
        }
```

```
                y++;
                print_8x8("0      1024    2048    3072    4096",
                                                xstart - 3, y, HISTI,
BGDI);
        y += 12;
        i = y;
        j = 8;
        while(j--)
                mem_to_mem((char far *)graybar, xy_to_ad(xstart, i++),
256);
        maxtick = ((maxcontrast > 4094) ? 4095 : maxcontrast) >> 4;
        mintick = ((mincontrast < 1) ? 0 : mincontrast) >> 4;
        i = y + 9;
        j = 4;
        while(j--)
        {
                wr_px_xy(xstart + mintick, i, HISTI);
                wr_px_xy(xstart + maxtick, i++, HISTI);
        }
        i = XINSTPOS + 16;
        j = YINSTPOS + 16;
        open_box(ib);
        print_8x16("UP    ARROW: Increase Contrast", i, j, FGDI, BGDI);
        print_8x16("DOWN  ARROW: Decrease Contrast", i, j += CHRH, FGDI,
BGDI);
        print_8x16("LEFT  ARROW: Data Window Left", i, j += CHRH, FGDI,
BGDI);
        print_8x16("RIGHT ARROW: Data Window Right", i, j += CHRH, FGDI,
BGDI);
        print_8x16("SPACE BAR   : Restore Auto-Gray",i, j += CHRH << 1,
FGDI, BGDI);
        print_8x16("F11   KEY   : Invert Video On CRT", i, j += CHRH,
FGDI, BGDI);
        print_8x16("ENTER KEY   : Return To Main Menu",i,j += CHRH <<
1,FGDI,BGDI);

k = 1;
        while(1)
        {
                while(i = readkey())
                {
                        switch(i)
                        {
                        case RIGHT_ARROW:
                                display_flag = 1;
                                maxcontrast += increment * k;
                                mincontrast += increment * k;
                                break;
                        case LEFT_ARROW:
                                display_flag = 1;
                                maxcontrast -= increment * k;
                                mincontrast -= increment * k;
                                break;
                        case UP_ARROW:
                                display_flag = 1;
                                maxcontrast -= increment * k;
                                mincontrast += increment * k;
                                if(maxcontrast - mincontrast < 1)
                                {
                                        maxcontrast += increment * k;
                                        mincontrast -= increment * k;
                                }
                                break;
                        case DOWN_ARROW:
                                display_flag = 1;
                                maxcontrast += increment * k;
                                mincontrast -= increment * k;
                                break;
                        case ' ':
                                display_flag = 1;
                                maxcontrast = maxdisplay;
```

```
                                mincontrast = mindisplay;
                                break;
                        case F11_KEY:
                                display_flag = 1;
                                invert_flag ^= 1;
                                break;
                        case F1_KEY:
        struct genbox *bp;

bp = &box;
        nrdbytes = nwrbytes =(out_amp == BOTH_AMP) ? FORDSIZE << 2 :
FORDSIZE << 1;
        lines = (bin_mode == NORMAL_M) ? FORDSIZE : (FORDSIZE >> 1);
        if(out_amp == BOTH_AMP) lines >>= 1;
        if(bin_mode == BINNED_M) nwrbytes >>= 1;

/*
open_box(bp);
print_8x16("W A I T I N G      F O R      X - R A Y      T O      B E G I N",
                                XWAITPOS + (CHRW << 1), YWAITPOS + CHRH,
FGDI, BGDI);
print_8x16("    -- Press ANY Key To Return To Main Menu    --",
                        XWAITPOS + (CHRW << 1), YWAITPOS + CHRH * 3,
FGDI, BGDI);
while(1)
        if(kbhit())
        {
                readkey();
                close_box(bp);
                return(ERROR);
        }
*/
        if((upper = lower = (int *)malloc(nrdbytes)) == NULL)
        {
                pr_error(5);
                return(ERROR);
        }
        lower += FORDSIZE;
        if((wbuf = (int *)malloc(nwrbytes)) == NULL)
        {
                pr_error(5);
                free((void *)upper);
                return(ERROR);
        }
        if((dbuf = (int *)malloc(nwrbytes)) == NULL)
        {
                pr_error(5);
                free((void *)upper);
                free((void *)wbuf);
                return(ERROR);
        }
        if((hist = (unsigned long *)calloc(MAXDATA + 256, sizeof(long)))
== NULL)
        {
                pr_error(5);
                free((void *)upper);
                free((void *)wbuf);
                free((void *)dbuf);
                return(ERROR);
        }
        if((fpw = open(wht_filespec, O_RDWR | O_BINARY,
                                        S_IREAD | S_IWRITE)) ==
ERROR)
        {
                pr_error(0);
                free((void *)upper);
                free((void *)wbuf);
                free((void *)dbuf);
                free((void *)hist);
                return(ERROR);
```

```c
        }
        if((fpd = open(drk_filespec, O_RDWR | O_BINARY,
                                     S_IREAD | S_IWRITE)) == ERROR)
        {
                pr_error(0);
                free((void *)upper);
                free((void *)wbuf);
                free((void *)dbuf);
                free((void *)hist);
                close(fpw);
                return(ERROR);
        } if(stst_method)
        {
                open_box(bp);
                print_8x16("W A I T I N G   F O R   X - R A Y   T O   B E G I N",
                                     XWAITPOS + (CHRW << 1), YWAITPOS + CHRH, FGDI, BGDI);
                print_8x16("  -- Press ANY Key To Return To Main Menu --",
                                     XWAITPOS + (CHRW << 1), YWAITPOS + CHRH * 3, FGDI, BGDI);
                while(inp(STAT_PORT) & XRAY)
                        if(kbhit())
                        {
                                readkey();
                                close_box(bp);
                                close(fpw);
                                close(fpd);
                                free((void *)upper);
                                free((void *)wbuf);
                                free((void *)dbuf);
                                free((void *)hist);
                                return(ERROR);
                        }
        }
        outp(MODE_PORT, out_amp | bin_mode);

outp(INT_PORT, 0);
        if(stst_method == 1)
                while(!(inp(STAT_PORT) & XRAY))
                {
                        delay(10);
                        i += 10;
                }
        else
                delay(i = int_time);
        outp(RSCLK_PORT, 0);

if(stst_method)
                close_box(bp);
        fpf = open(filespec, O_RDWR | O_CREAT | O_BINARY | O_TRUNC,
                                     S_IREAD | S_IWRITE);
        switch(out_amp)
        {
                case BOTH_AMP:
                        while(lines--)
                        {
                                while(inp(STAT_PORT) & LINERDY);
                                inpw_to_mem((char far *)lower, FIFO1_PORT, FORDSIZE);
                                inpw_to_mem((char far *)upper, FIFO2_PORT, FORDSIZE);
                                outp(RSCLK_PORT, 0);
                                if(bin_mode == BINNED_M)
                                {
                                        squeeze(upper, nwrbytes);
                                        xchg_array(upper, BINSIZE);
```

```
                    }
                    else
                                xchg_array(upper, FORDSIZE);
                        read(fpw, wbuf, nwrbytes);
                        read(fpd, dbuf, nwrbytes);

process_image(hist,upper,wbuf,dbuf,nwrbytes >> 1,&big,&small);
                        write(fpf, upper, nwrbytes);
                }
                break;
            case LOWER_AMP:
                while(lines--)
                {
                        while(inp(STAT_PORT) & LINERDY);
                        inpw_to_mem((char far *)upper,
FIFO1_PORT, FORDSIZE);

outp(RSCLK_PORT, 0);
                        if(bin_mode == BINNED_M)
                                squeeze(upper, nwrbytes);
                        read(fpw, wbuf, nwrbytes);
                        read(fpd, dbuf, nwrbytes);

process_image(hist,upper,wbuf,dbuf,nwrbytes >> 1,&big,&small);
                        write(fpf, upper, nwrbytes);
                }
                break;
            case UPPER_AMP:
                while(lines--)
                {
                        while(inp(STAT_PORT) & LINERDY);
                        inpw_to_mem((char far *)upper,
FIFO2_PORT, FORDSIZE);

outp(RSCLK_PORT, 0);
                    xchg_array(upper, FORDSIZE);
                        if(bin_mode == BINNED_M)
                                squeeze(upper + 1, nwrbytes);
                        read(fpw, wbuf, nwrbytes);
                        read(fpd, dbuf, nwrbytes);

process_image(hist,upper,wbuf,dbuf,nwrbytes >> 1,&big,&small);
                        write(fpf, upper, nwrbytes);
                }
                break;
        }
        outp(MODE_PORT, BOTH_AMP | FLUSH_M);
        inp(RSRDOUT_PORT);
        outp(RSCLK_PORT, 0);

free((void *)upper);
        free((void *)wbuf);
        free((void *)dbuf);
        close(fpf);
        close(fpw);
        close(fpd);

maximage = big;
        minimage = small;
        find_contrast(hist);
        dup_image();
        display_image(filespec, mindisplay, maxdisplay);
        free((void *)hist);
        date_stamp_annot(i);
        return(i);
}
cycle(lines)
int lines;
{
        void *malloc();
        int x, x1, y, y1, cols, fpf;
```

```
            unsigned int nbytes;
            int *lower, *upper, *plower, *pupper;
            unsigned char far *dest, far *xy_to_ad();

nbytes = (out_amp == BOTH_AMP) ? FORDSIZE << 2 : FORDSIZE << 1;
            if((upper = lower = (int *)malloc(nbytes)) == NULL)
            {
                    pr_error(5);
                    return(ERROR);
            }
            lower += FORDSIZE;
            if((fpf = open(fin_filespec, O_RDWR | O_CREAT | O_BINARY,
                                                S_IREAD | S_IWRITE)) ==
ERROR)
            {
                    pr_error(0);
                    free((void *)upper);
                    return(ERROR);
            } while(!readkey())
            {
            lseek(fpf, 0L, SEEK_SET);
            outp(MODE_PORT, out_amp | NORMAL_M);
            outp(INT_PORT, 0);
            delay(int_time);
            outp(RSCLK_PORT, 0);

switch(out_amp)
            {
                    case BOTH_AMP:
                            for(y = 0; y < lines; y++)
                            {
                                    while(inp(STAT_PORT) & LINERDY);
                                    inpw_to_mem((char far *)upper,
FIFO1_PORT, FORDSIZE);
                                    inpw_to_mem((char far *)lower,
FIFO2_PORT, FORDSIZE);
                                    outp(RSCLK_PORT, 0);
                                    write(fpf, upper, nbytes);
                            }
                            break;
                    case LOWER_AMP:
                            for(y = 0; y < lines; y++)
                            {
                                    while(inp(STAT_PORT) & LINERDY);
                                    inpw_to_mem((char far *)upper,
FIFO1_PORT, FORDSIZE);
                                    outp(RSCLK_PORT, 0);
                                    write(fpf, upper, nbytes);
                            }
                            break;
                    case UPPER_AMP:
                            for(y = 0; y < lines; y++)
                            {
                                    while(inp(STAT_PORT) & LINERDY);
                                    inpw_to_mem((char far *)upper,
FIFO2_PORT, FORDSIZE);
                                    outp(RSCLK_PORT, 0);
                                    write(fpf, upper, nbytes);
                            }
                            break;
            }
            outp(MODE_PORT, BOTH_AMP | FLUSH_M);
            inp(RSRDOUT_PORT);
            outp(RSCLK_PORT, 0);

lseek(fpf, 0L, SEEK_SET);

/*
```

```
                for(y = 0; y < TOPBORDER; y++)
                        read(fpf, upper, nbytes);
*/
        x = y = 0;
        x1 = 1023, y1 = 767;
        switch(out_amp)
        {
        case BOTH_AMP:
                while(y < lines)
                {
                        plower = lower;
                        pupper = upper;
                        read(fpf, upper, nbytes);
                        dest = xy_to_ad(x, y++);
                        cols = FORDSIZE;
                        while(cols--)
                                *dest++ = *pupper++ >> crtbitshft;
                        dest = xy_to_ad(x1, y1--);
                        cols = FORDSIZE;
                        while(cols--)
                                *dest-- = *plower++ >> crtbitshft;
                }
                break;
        case LOWER_AMP:
                while(y < lines)
                {
                        pupper = upper;
                        read(fpf, upper, nbytes);
                        dest = xy_to_ad(x, y++);
                        cols = FORDSIZE;
                        while(cols--)
                                *dest++ = *pupper++ >> crtbitshft;
                }
                break;
        case UPPER_AMP:
                while(y++ < lines)
                {
                        pupper = upper;
                        read(fpf, upper, nbytes);
                        dest = xy_to_ad(x1, y1--);
                        cols = FORDSIZE;
                        while(cols--)
                                *dest-- = *pupper++ >> crtbitshft;
                }
                break;
        }
        close(fpf);
        free((void *)upper);
} init_ford()
{
        char *whtfspec, *drkfspec;
        int old_maximage, old_minimage, old_maxcontrast,
old_mincontrast;
        int old_maxdisplay, old_mindisplay;
        unsigned old_histdata[256];

outp(MODE_PORT, BOTH_AMP | FLUSH_M);
        inp(RSRDOUT_PORT);
        outp(RSCLK_PORT, 0);
        if(bin_mode == NORMAL_M)
        {
                whtfspec = hf_wht_fspec;
                drkfspec = hf_drk_fspec;
        }
        else
        {
                whtfspec = hb_wht_fspec;
                drkfspec = hb_drk_fspec;
```

```c
        }
        copy_image(whtfspec, wht_filespec);
        copy_image(drkfspec, drk_filespec);
        if(int_formula == 3)
        {
                subtract_image(wht_filespec, drk_filespec,
tmp_filespec);
                copy_image(tmp_filespec, wht_filespec);
        } old_maximage = maximage, old_minimage = minimage;
        old_maxcontrast = maxcontrast, old_mincontrast = mincontrast;
        old_maxdisplay = maxdisplay, old_mindisplay = mindisplay;
        memcpy(old_histdata, histdata, 256 * sizeof(int));
        find_maxwhite();
        maximage = old_maximage, minimage = old_minimage;
        maxcontrast = old_maxcontrast, mincontrast = old_mincontrast;
        maxdisplay = old_maxdisplay, mindisplay = old_mindisplay;
        memcpy(histdata, old_histdata, 256 * sizeof(int));
} set_display_bits(disp_flag)
int disp_flag;
{
        int menupt;

static struct menwindow menu =
        {
                13, 7, "Display Bits:", "F1: 11 thru 4", "F2: 10 thru
3",
                "F3: 9 thru 2", "F4: 8 thru 1", "F5: 7 thru 0", "F6:
Prev Menu"
        };
        struct menwindow *wp;

wp = &menu;

switch(menupt = get_menu_ptr(wp, TRUE, FALSE))
        {
        case 0:
        case 1:
        case 2:
        case 3:
        case 4:
                crtbitshft = 4 - menupt;
                if(disp_flag)
                {
                        find_maxmin(fin_filespec);
                        display_image(fin_filespec,
                                                mincontrast = 0,
maxcontrast = (4096 >> menupt) - 1);
                }
                break;
        case 5:
        case 6:
                break;
        }
} set_parameters()
{
        int xstatus, ystatus, i;
        char buf[64], *gr_gets();
        static struct menwindow menu =
        {
                17, 9, "  - Parameter -", "F1: Integrate Tm:", "F2:
Start / Stop:",
                "F3: Math Formula:", "F4: Output Amp   :", "F5: Binning
Mode:",
                "F6: Display Mode:", "F7: Stereo Mode :", "F8: Previous
```

Menu"
```
        };
        struct menwindow *wp, *qm;

wp = &menu;
        qm = &quit_menu;
        xstatus = xmenu + CHRW * (wp->xlen + 3);
        ystatus = ymenu + CHRH * 3;

wp->xlen += EXTRACHRS;
        open_window(wp);
        wp->xlen -= EXTRACHRS;
        print_status(xstatus, ystatus);
        print_8x16("- Current Value -", xstatus, ymenu + CHRH, FGDI,
BGDI);
        while(1)
        {
                i = get_menu_ptr(wp, FALSE, FALSE);
                rev_fgd_bkgd(xmenu + 14, ymenu + 3 * CHRH + i * CHRH,
                                        FGDI, BGDI, (wp->xlen <<
3) + 4, CHRH);
                print_8x16("\x10",       xstatus - CHRW, ystatus + i *
CHRH, FGDI, BGDI);
                switch(i)
                {
                case 0:
                        print_8x16("Enter Time: ", xstatus, ystatus,
FGDI, BGDI);
                        sscanf(gr_gets(buf, xstatus + (12 << 3), ystatus,
5),"%d", &int_time);
                        print_status(xstatus, ystatus);
                        break;
                case 1:
                        get_stsp(xstatus, ystatus);
                        break;
                case 2:
                        get_form(xstatus, ystatus);
                        init_ford();
                        break;
                case 3:
                        get_out_amp(xstatus, ystatus);
                        break;
                case 4:
                        get_bin_mode(xstatus, ystatus);
                        init_ford();
                        break;
                case 5:
                        get_disp_mode(xstatus, ystatus);
                        break;
                case 6:
                        get_ste_mode(xstatus, ystatus);
                        break;
                case 7:
                        wp->xlen += EXTRACHRS;
                        close_window(wp);
                        wp->xlen -= EXTRACHRS;
                        switch(get_menu_ptr(qm, TRUE, FALSE))
                        {
                                case 0:
                                case 1:
                                        save_defaults();
                                        break;
                        }
                        return;
                        break;
                }
                print_8x16(" ", xstatus - CHRW, ystatus + i * CHRH,
FGDI, BGDI);
        }
}
```

```
print_status(xmen, ymen)
int xmen, ymen;
{
        char buffer[32];

sprintf(buffer, "%-18u", int_time);
        print_8x16(buffer, xmen, ymen, FGDI, BGDI);
        print_8x16(ststresponses[stst_method], xmen, ymen += CHRH, FGDI,
BGDI);
        print_8x16(formresponses[int_formula], xmen, ymen += CHRH, FGDI,
BGDI);
        print_8x16(outresponses[out_amp - 4 >> 2], xmen, ymen += CHRH,
FGDI, BGDI);
        print_8x16(binresponses[bin_mode], xmen, ymen += CHRH, FGDI,
BGDI);
        print_8x16(dispresponses[crt_mode], xmen, ymen += CHRH, FGDI,
BGDI);
        print_8x16(steresponses[stereo_mode], xmen, ymen += CHRH, FGDI,
BGDI);
} get_stsp(xstatus, ystatus)
int xstatus, ystatus;
{
        int i;

while((i = get_key()) != '\r')
        {
                switch(i)
                {
                        case DOWN_ARROW:
                        case RIGHT_ARROW:
                        case ' ':
                                if(++stst_method == ststmax) stst_method
= 0;
                                break;
                        case UP_ARROW:
                        case LEFT_ARROW:
                                if(--stst_method < 0) stst_method +=
ststmax;
                                break;
                }
                print_status(xstatus, ystatus);
        }
} get_form(xstatus, ystatus)
int xstatus, ystatus;
{
        int i;

while((i = get_key()) != '\r')
        {
                switch(i)
                {
                        case DOWN_ARROW:
                        case RIGHT_ARROW:
                        case ' ':
                                if(++int_formula == formmax) int_formula
= 0;
                                break;
                        case UP_ARROW:
                        case LEFT_ARROW:
                                if(--int_formula < 0) int_formula +=
formmax;
                                break;
                }
                print_status(xstatus, ystatus);
        }
```

```
}
get_out_amp(xstatus, ystatus)
int xstatus, ystatus;
{
        int i;

while((i = get_key()) != '\r')
        {
                switch(i)
                {
                        case DOWN_ARROW:
                        case RIGHT_ARROW:
                        case ' ':
                                if((out_amp += 4) > outampmax) out_amp =
4;
                                break;
                        case UP_ARROW:
                        case LEFT_ARROW:
                                if((out_amp -= 4) < 4) out_amp =
outampmax;
                                break;
                }
                print_status(xstatus, ystatus);
        }
}
get_bin_mode(xstatus, ystatus)
int xstatus, ystatus;
{
        int i;

while((i = get_key()) != '\r')
        {
                switch(i)
                {
                        case DOWN_ARROW:
                        case RIGHT_ARROW:
                        case UP_ARROW:
                        case LEFT_ARROW:
                        case ' ':
                                bin_mode ^= 1;
                                break;
                }
                print_status(xstatus, ystatus);
        }
}
get_disp_mode(xstatus, ystatus)
int xstatus, ystatus;
{
        int i, oldcrtmode;

oldcrtmode = crt_mode;
        while((i = get_key()) != '\r')
        {
        switch(i)
        {
                case DOWN_ARROW:
                case RIGHT_ARROW:
                case UP_ARROW:
                case LEFT_ARROW:
                case ' ':
                        crt_mode ^= 1;
                        break;
        }
        print_status(xstatus, ystatus);
        }
}
if(oldcrtmode != crt_mode && !crt_mode)
        clear_image(1);
```

```
}
get_ste_mode(xstatus, ystatus)
int xstatus, ystatus;
{
        int i;

while((i = get_key()) != '\r')
        {
                switch(i)
                {
                        case DOWN_ARROW:
                        case RIGHT_ARROW:
                        case UP_ARROW:
                        case LEFT_ARROW:
                        case ' ':
                                stereo_mode ^= 1;
                                break;
                }
                print_status(xstatus, ystatus);
        }
} subtract_image(fspec1, fspec2, fspec3)
char *fspec1, *fspec2, *fspec3;
{
        void *malloc();
        int cols, size, fp1, fp2, fp3;
        int *buf1, *pbuf1, *buf2, *pbuf2;
        unsigned int nbytes = FORDSIZE << 1;
        long filelength();

if((buf1 = (int *)malloc(nbytes)) == NULL)
        {
                pr_error(5);
                return(ERROR);
        }
        if((buf2 = (int *)malloc(nbytes)) == NULL)
        {
                pr_error(5);
                free((void *)buf1);
                return(ERROR);
        }
        if((fp1 = open(fspec1, O_RDWR | O_BINARY, S_IREAD | S_IWRITE))
== ERROR)
        {
                pr_error(0);
                free((void *)buf1);
                free((void *)buf2);
                return(ERROR);
        }
        if((fp2 = open(fspec2, O_RDWR | O_BINARY, S_IREAD | S_IWRITE))
== ERROR)
        {
                pr_error(0);
                free((void *)buf1);
                free((void *)buf2);
                close(fp1);
                return(ERROR);
        }
        if((fp3 = open(fspec3, O_RDWR | O_CREAT | O_BINARY | O_TRUNC,
                                        S_IREAD | S_IWRITE)) ==
ERROR)
        {
                pr_error(0);
                free((void *)buf1);
                free((void *)buf2);
                close(fp1);
                close(fp2);
                return(ERROR);
```

```
            }
            size = filelength(fp1) / nbytes;
            while(size--)
            {
                    read(fp1, buf1, nbytes);
                    read(fp2, buf2, nbytes);
                    pbuf1 = buf1;
                    pbuf2 = buf2;
                    cols = FORDSIZE;
                    while(cols--)
                    {
                            *pbuf1 -= *pbuf2++;
                            if(*pbuf1 < 0) *pbuf1 = 0;
                            pbuf1++;
                    }
                    write(fp3, buf1, nbytes);
            }
            close(fp1);
            close(fp2);
            close(fp3);
            free((void *)buf1);
            free((void *)buf2);
            return(0);
} divide_image(fspec1, fspec2, fspec3)
char *fspec1, *fspec2, *fspec3;
{
            void *malloc();
            int cols, size, fp1, fp2, fp3;

unsigned int nbytes = FORDSIZE << 1, *buf1, *pbuf1, *buf2,
*pbuf2;
            long filelength();

if((buf1 = (int *)malloc(nbytes)) == NULL)
            {
                    pr_error(5);
                    return(ERROR);
            }
            if((buf2 = (int *)malloc(nbytes)) == NULL)
            {
                    pr_error(5);
                    free((void *)buf1);
                    return(ERROR);
            }
            if((fp1 = open(fspec1, O_RDWR | O_BINARY, S_IREAD | S_IWRITE))
== ERROR)
            {
                    pr_error(0);
                    free((void *)buf1);
                    free((void *)buf2);
                    return(ERROR);
            }
            if((fp2 = open(fspec2, O_RDWR | O_BINARY, S_IREAD | S_IWRITE))
== ERROR)
            {
                    pr_error(0);
                    free((void *)buf1);
                    free((void *)buf2);
                    close(fp1);
                    return(ERROR);
            }
            if((fp3 = open(fspec3, O_RDWR | O_CREAT | O_BINARY | O_TRUNC,
                                            S_IREAD | S_IWRITE)) ==
ERROR)
            {
                    pr_error(0);
                    free((void *)buf1);
                    free((void *)buf2);
```

```
                close(fp1);
                close(fp2);
                return(ERROR);
        }
        size = filelength(fp1) / nbytes;
        while(size--)
        {
                read(fp1, buf1, nbytes);
                read(fp2, buf2, nbytes);
                pbuf1 = buf1;
                pbuf2 = buf2;
                cols = FORDSIZE;
                while(cols--)
                {
                        *pbuf1 = (*pbuf1 * (long)maxwhite) /
++(*pbuf2++);
                        if(*pbuf1 > 4095) *pbuf1 = 4095;
                        pbuf1++;
                }
                write(fp3, buf1, nbytes);
        } close(fp1);
        close(fp2);
        close(fp3);
        free((void *)buf1);
        free((void *)buf2);
        return(0);
} copy_image(fspec1, fspec2)
char *fspec1, *fspec2;
{
        void *malloc();
        int blocks, fp1, fp2, *file1;
        unsigned int nbytes = 0x8000;
        long filelength();

if((file1 = (int *)malloc(nbytes)) == NULL)
        {
                pr_error(5);
                return(ERROR);
        }
        if((fp1 = open(fspec1, O_RDWR | O_BINARY, S_IREAD | S_IWRITE))
== ERROR)
        {
                (strcmp(fspec1, fin_filespec)) ? pr_error(1) :
pr_error(6);
                free((void *)file1);
                return(ERROR);
        }
        if((fp2 = open(fspec2, O_RDWR | O_CREAT | O_BINARY | O_TRUNC,
                                        S_IREAD | S_IWRITE)) ==
ERROR)
        {
                pr_error(0);
                free((void *)file1);
                close(fp1);
                return(ERROR);
        }
        blocks = filelength(fp1) / nbytes;
        while(blocks--)
        {
                read(fp1, file1, nbytes);
                write(fp2, file1, nbytes);
        } close(fp1);
        close(fp2);
        free((void *)file1);
        return(0);
```

```c
} find_maxwhite()
{
        find_maxmin(wht_filespec);
        maxwhite = maxdisplay;
} find_maxmin(fspec)
char *fspec;
{
        void *malloc(), *calloc();
        int big = 0, small = 4096, y, cols, fp1, *buf, *pbuf;
        unsigned int nbytes = FORDSIZE << 1;
        unsigned long *hist;
        long filelength();

if((buf = (int *)malloc(nbytes)) == NULL)
        {
                pr_error(5);
                return(ERROR);
        }
        if((hist = (unsigned long *)calloc(MAXDATA + 256, sizeof(long)))
== NULL)
        {
                pr_error(5);
                free((void *)buf);
                return(ERROR);
        } if((fp1 = open(fspec, O_RDWR | O_BINARY, S_IREAD | S_IWRITE)) ==
ERROR)
        {
                pr_error(0);
                free((void *)buf);
                free((void *)hist);
                return(ERROR);
        } y = filelength(fp1) / nbytes;
        while(y--)
        {
                read(fp1, buf, nbytes);
                pbuf = buf;
                cols = FORDSIZE;
                while(cols--)
                {
                        big = (big > *pbuf) ? big : *pbuf;
                        small = (small < *pbuf) ? small : *pbuf;
                        hist[*pbuf++]++;
                }
        }
/*
        y = 0;
        while(y < MAXDATA)
                fprintf(stdprn, "%8lu", hist[y++]);
*/
        maximage = big;
        minimage = small;
        find_contrast(hist);
        close(fp1);
        free((void *)buf);
        free((void *)hist);
} find_contrast(hist)
unsigned long *hist;
{
        int big, small, y, min, smax, smin;
        unsigned long *phist, histbig;
```

```
            phist = hist + MAXDATA;
            y = smax = smin = 0;
            while(y < 4094)
            {
                    maxcontrast = mincontrast = 0;
                    while(maxcontrast - mincontrast < HST_CONT_MIN)
                    {
                            while(hist[y++] < HST_THRESHOLD);
                            mincontrast = y;

- Table 2 p.117- while(hist[y++] > HST_THRESHOLD);
                            maxcontrast = y;
                            if(y > 4094) break;
                    }
                    min = maxcontrast;
                    while(min - maxcontrast < HST_CONT_MIN)
                    {
                            while(hist[y++] > HST_THRESHOLD);
                            maxcontrast = y;
                            while(hist[y++] < HST_THRESHOLD);
                            min = y;
                            if(y > 4094) break;
                    }
                    if(maxcontrast > maximage) maxcontrast = maximage;
                    if(smax - smin < maxcontrast - mincontrast)
                    {
                            smax = maxcontrast;
                            smin = mincontrast;
                    }
            }
            maxcontrast = smax, mincontrast = smin;
            if(maxcontrast > maximage) maxcontrast = maximage;
            if(mincontrast < minimage) mincontrast = minimage;
            if(maxcontrast - mincontrast < 10)
            {
                    maxcontrast = maximage;
                    mincontrast = minimage;
            }
            if(maxcontrast - mincontrast < 1)
            {
                    maxcontrast = 4095;
                    mincontrast = 0;
            } big = maxdisplay = maxcontrast;
            small = mindisplay = mincontrast;

for(y = 0; y < MAXDATA; y++)
                    phist[y >> 4] += hist[y];
            small >>= 4, big >>= 4;
            big++;
            for(y = small, histbig = phist[small]; y < big; y++)
                    histbig = (histbig > phist[y]) ? histbig : phist[y];
            histbig >>= 6;
            for(y = 0; y < 256; y++)
                    histdata[y] = phist[y] / histbig;
} display_fullgry(filespec)
char *filespec;
{

- Table 2 p.118- find_maxmin(filespec);
        display_image(filespec, mindisplay, maxdisplay);
}
```

```
display_image(filespec, min, max, topborder)
char *filespec;
int min, max, topborder;
{
        void *malloc();
        int x, y, y1, maxmin, cols, fpf, *data, *pdata, maxdisp,
mindisp, oldmode;
        unsigned int nbytes;
        unsigned char *lut, far *dest, far *xy_to_ad();
        long filelength();

if((fpf = open(filespec, O_RDWR | O_BINARY, S_IREAD | S_IWRITE))
== ERROR)
        {
                pr_error(7);
                return(ERROR);
        }
        oldmode = bin_mode;
        bin_mode = (filelength(fpf) == 524288L) ? BINNED_M : NORMAL_M;
        nbytes = (out_amp == BOTH_AMP) ? FORDSIZE << 2 : FORDSIZE << 1;
        if(bin_mode == BINNED_M) nbytes >>= 1;
        if((lut = (char *)malloc(MAXDATA)) == NULL)
        {
                pr_error(5);
                close(fpf);
                return(ERROR);
        }
        if((data = (int *)malloc(nbytes)) == NULL)
        {
                pr_error(5);
                free((void *)lut);
                close(fpf);
                return(ERROR);
        } maxmin = max - min;
        maxdisp = (max > 4094) ? 4095 : max;
        mindisp = (min < 1) ? 0 : min;
        x = XDISPRNGPOS, y = YDISPRNGPOS;
        make_gen_box(x, y, 37, 4);
        sprintf(lut, "Displayed Data Range:%5d -%5d", mindisp, maxdisp);
        print_8x16(lut, x += (CHRW << 1), y += CHRH, FGDI, BGDI);
        sprintf(lut, "Data Range In Image :%5d -%5d", minimage,
maximage);
        print_8x16(lut, x, y + CHRH, FGDI, BGDI);
        for(y = 0; y < 4096; y++)
        {

- Table 2 p.119- x = ((y - min) * 255L) / maxmin;
                if(x > 255) x = 255;
                if(x < 0) x = 0;
                *(lut + y) = (invert_flag) ? ~x : x;
        } if(disp_mode == SPLIT_M || bin_mode == BINNED_M)
        {
        switch(out_amp)
        {
        case LOWER_AMP:
                for(x = XIMAGEBIN, y = YIMAGEBIN; y < YIMAGEBIN +
BINSIZE; y++)
                {
                        if(bin_mode == NORMAL_M)
                                read(fpf, data, nbytes);
                        read(fpf, data, nbytes);
                        pdata = data;
                        dest = xy_to_ad(x, y);
                        cols = BINSIZE;
                        if(bin_mode == NORMAL_M)
                        {
```

```
                    while(cols--)
                    {
                            *pdata++;
                            *dest++ = *(lut + *pdata++);
                    }
            }
            else
            {
                    while(cols--)
                            *dest++ = *(lut + *pdata++);
            }
        }
        break;
    case UPPER_AMP:
        for(x = XIMAGEBIN, y = YIMAGEBIN + BINSIZE - 1; y >
YIMAGEBIN; y--)
        {
            if(bin_mode == NORMAL_M)
                    read(fpf, data, nbytes);
            read(fpf, data, nbytes);
            pdata = data;
            dest = xy_to_ad(x, y);
            cols = BINSIZE;
            if(bin_mode == NORMAL_M)
            {
                    while(cols--)
                    {
                            *pdata++;
                            *dest++ = *(lut + *pdata++);
```

- Table 2 p.120-

```
                    }
            }
            else
            {
                    while(cols--)
                            *dest++ = *(lut + *pdata++);
            }
        }
        break;
    case BOTH_AMP:
        for(x = XIMAGEBIN, y = YIMAGEBIN, y1 = YIMAGEBIN +
BINSIZE - 2;
                                          y < YIMAGEBIN + (BINSIZE
>> 1); y++, y1--)
        {
            if(bin_mode == NORMAL_M)
                    read(fpf, data, nbytes);
            read(fpf, data, nbytes);
            pdata = data;
            dest = xy_to_ad(x, y1);
            cols = BINSIZE;
            if(bin_mode == NORMAL_M)
            {
                    while(cols--)
                    {
                            *pdata++;
                            *dest++ = *(lut + *pdata++);
                    }
            }
            else
            {
                    while(cols--)
                            *dest++ = *(lut + *pdata++);
            }
            dest = xy_to_ad(x, y);
            cols = BINSIZE;
            if(bin_mode == NORMAL_M)
            {
                    while(cols--)
                    {
```

```
                                        *pdata++;
                                        *dest++ = *(lut + *pdata++);
                        }
                }
                else
                {
                        while(cols--)
                                *dest++ = *(lut + *pdata++);
                }
        }
        break;
```

— Table 2 p.121—

```
        }
        if(bin_mode == NORMAL_M)
        {
                make_gen_box(XZOOMPOS, YZOOMPOS, 37, 3);
                print_8x16("Press SF1 For Full Screen Display",
                        XZOOMPOS + (CHRW << 1), YZOOMPOS + CHRH, FGDI,
BGDI);
                zoomflag = 1;
        }
        else
        {
                for(cols = 0; cols < 37; cols++)
                        lut[cols] = ' ';
                lut[cols] = '\0';
                cols = 3;
                y = YZOOMPOS - CHRH;
                while(cols--)
                        print_8x16(lut, XZOOMPOS, y += CHRH, FGDI, 0);
                zoomflag = 0;
        }
}
else
{
for(y = 0; y < topborder; y++)
        read(fpf, data, nbytes);
switch(out_amp)
{
case LOWER_AMP:
        for(x = XIMAGEPOS, y = YIMAGEPOS; y < YIMAGEPOS +
MAXVIDEOLINE; y++)
                {
                        read(fpf, data, nbytes);
                        pdata = data;
                        dest = xy_to_ad(x, y);
                        cols = FORDSIZE;
                        while(cols--)
                                *dest++ = *(lut + *pdata++);
                }
        break;
case UPPER_AMP:
        for(x = XIMAGEPOS, y = YIMAGEPOS + MAXVIDEOLINE - 1; y;
y--)
                {
                        read(fpf, data, nbytes);
                        pdata = data;
                        dest = xy_to_ad(x, y);
                        cols = FORDSIZE;
                        while(cols--)
                                *dest++ = *(lut + *pdata++);
                }
        break;
```

— Table 2 p.122—

```
        case BOTH_AMP:
                for(x = XIMAGEPOS, y = YIMAGEPOS, y1 = YIMAGEPOS +
MAXVIDEOLINE - 2;
```

```
                            y < MAXVIDEOLINE >> 1;
y++, y1--)
        {
                read(fpf, data, nbytes);
                pdata = data;
                dest = xy_to_ad(x, y1);
                cols = FORDSIZE;
                while(cols--)
                        *dest++ = *(lut + *pdata++);
                dest = xy_to_ad(x, y);
                cols = FORDSIZE;
                while(cols--)
                        *dest++ = *(lut + *pdata++);
        }
        break;
    }
    } free((void *)data);
    free((void *)lut);
    close(fpf);
    bin_mode = oldmode;
} disp_full_screen()
{
    int i, border = TOPBORDER;

if(zoomflag)
    {
        sav_image(tmp_filespec);
        disp_mode = NORMAL_M;
        display_image(fin_filespec, mincontrast, maxcontrast,
border);
        while((i = get_key()) != '\r')
        {
            switch(i)
            {
            case PG_UP:
                border -= 128;
                if(border < 0) border = 0;
                display_image(fin_filespec, mincontrast,
maxcontrast, border);
                break;
            case PG_DOWN:
                border += 128;
                if(border > 256) border = 256;
                display_image(fin_filespec, mincontrast,

- Table 2 p.123- maxcontrast, border);
                break;
            }
        }
        disp_mode = SPLIT_M;
        rec_image(tmp_filespec);
    }
} process_image(hist, pdata, pwdata, pddata, ncols, big, small)
unsigned long *hist;
int *pdata, *pwdata, *pddata, ncols, *big, *small;
{
    switch(int_formula)
    {
    case 0:
        while(ncols--)
        {
            *big = (*big > *pdata) ? *big : *pdata;
            *small = (*small < *pdata) ? *small :
```

```
                        *pdata;
                                        hist[*pdata++]++;
                                }
                                break;
                        case 1:
                                while(ncols--)
                                {
                                        *pdata -= *pddata++;
                                        if(*pdata < 0) *pdata = 0;
                                        *big = (*big > *pdata) ? *big : *pdata;
                                        *small = (*small < *pdata) ? *small :
*pdata;
                                        hist[*pdata++]++;
                                }
                                break;
                        case 2:
                                while(ncols--)
                                {
                                        *pdata = (*pdata * (long)maxwhite) /
++(*pwdata++);
                                        if(*pdata > 4095 || *pdata < 0) *pdata =
4095;
                                        *big = (*big > *pdata) ? *big : *pdata;
                                        *small = (*small < *pdata) ? *small :
*pdata;
                                        hist[*pdata++]++;
                                }
                                break;
                        case 3:
                                while(ncols--)
                                {

- Table 2 p.124-

*pdata -= *pddata++;
                                        if(*pdata < 0) *pdata = 0;
                                        *pdata = (*pdata * (long)maxwhite) /
++(*pwdata++);
                                        if(*pdata > 4095 || *pdata < 0) *pdata =
4095;
                                        *big = (*big > *pdata) ? *big : *pdata;
                                        *small = (*small < *pdata) ? *small :
*pdata;
                                        hist[*pdata++]++;
                                }
                                break;
                }
} dup_image()
{
        int x, y;
        unsigned char far *dest, far *xy_to_ad();

y = (stereo_mode) ? YIMAGEBIN : 0;
        if((disp_mode == SPLIT_M || bin_mode == BINNED_M) && crt_mode ==
TRUE)
                for(x = 0; y < YIMAGEBIN + BINSIZE + 72; y++)
                {
                        dest = xy_to_ad(x, y);
                        mem_to_mem(dest, dest + BINSIZE, BINSIZE);
                }
} save_defaults()
{
        FILE *stream;

if((stream = fopen(cnf_filespec, "w")) == NULL)
        {
                pr_error(0);
                return(ERROR);
```

```
        }
        fprintf(stream, "%d %d %d %d %d %d %d",
                                        int_time, stst_method,
int_formula, out_amp, bin_mode,
                                        crt_mode, stereo_mode);
        fclose(stream);
        return(0);
}
get_defaults()
{
        FILE *stream;
```

- Table 2 p.125-

```
        if((stream = fopen(cnf_filespec, "r")) == NULL)
                return(ERROR);
        fscanf(stream, "%d %d %d %d %d %d %d",
                                        &int_time, &stst_method, &int_formula,
&out_amp, &bin_mode,
                                        &crt_mode, &stereo_mode);
        fclose(stream);
        return(0);
}
/***************************************************************
        This function controls:
                Making disk files for image processing (White and Dark).
                Making the defect mapping file.
***************************************************************/

/*
Tony Scandura    04/29/91
*/ include <stdio.h>
include <fcntl.h>
#include <sys\types.h>
#include <sys\stat.h>
#include <math.h>
#include "ccd.h"
#include "keys.h"

struct menwindow quit_menu =
{
        17, 4, "Please Select One", "Save As Default",
        "Save As Filespec", "  Do  NOT  Save"
};
extern int xmenu, ymenu, bin_mode;
extern char *fin_filespec, *tmp_filespec, *wht_filespec, *drk_filespec;
extern char *hf_wht_fspec, *hb_wht_fspec, *hf_drk_fspec, *hb_drk_fspec;

make_files()
{
        int i;
        static struct menwindow menu =
        {
                20, 5, " - Make File Menu -", "F1: Make White File",
                "F2: Make Dark File", "F3: Make Defect File", "F4: Main
Menu"
        };
        struct menwindow *wp;
        wp = &menu;

while((i = get_menu_ptr(wp, TRUE, FALSE)) != '\r')
        {
                switch(i)
```

- Table 2 p.126-

```
                {
                case 0:
                case 1:
```

```c
                            mk_files(i);
                            break;
                    case 2:
                            mk_defect();
                            break;
                    case 3:
                            return;
                            break;
                    }
            }
    }
    mk_files(bw)
    int bw;
    {
            int i, imagecnt = 0, useflag = ERROR;
            char buf[16], *fspec;
            static struct menwindow menu =
            {
                    19, 4, "White File Creation", "Press ENTER When",
                    "Ready For Image: 1", "    (A)dd   (Q)uit"
            };
            struct menwindow *wp, *qm;
            wp = &menu;
            qm = &quit_menu;
            fspec = (bw) ? ((bin_mode == NORMAL_M) ? hf_drk_fspec :
    hb_drk_fspec) :
                                                    ((bin_mode == NORMAL_M) ?
    hf_wht_fspec : hb_wht_fspec);
            open_window(wp);
            sprintf(buf, "%s", (bw) ? " Dark" : "White");
            print_8x16(buf, xmenu + CHRW * 2, ymenu + CHRH, FGDI, BGDI);
            while(1)
            {
                    switch(i = get_key())
                    {
                    case '\r':
                            close_window(wp);
                            useflag = (imagecnt) ?
                                    int_raw(tmp_filespec) :
    int_raw(fin_filespec);
                            open_window(wp);
                            sprintf(buf, "%s", (bw) ? " Dark" : "White");
                            print_8x16(buf, xmenu + CHRW * 2, ymenu + CHRH,
    FGDI, BGDI);
                            sprintf(buf, "%d", imagecnt + 1);
                            print_8x16(buf, xmenu + CHRW * 19, ymenu + CHRH
    * 4, FGDI, BGDI);

- Table 2 p.127- break;
                    case 'Q':
                    case 'q':
                            close_window(wp);
                            if(imagecnt)
                            switch(get_menu_ptr(qm, TRUE, FALSE))
                            {
                            case 0:
                                    divide_it(imagecnt);
                                    copy_image(fin_filespec, fspec);
                                    display_fullgry(fin_filespec);
                                    init_ford();
                                    break;
                            case 1:
                                    divide_it(imagecnt);
                                    save_it(fin_filespec, TRUE);
                                    display_fullgry(fin_filespec);
                                    init_ford();
                                    break;
```

```
                    case 2:
                        init_ford();
                        break;
                }
                return;
                break;
            case 'A':
            case 'a':
                if(useflag != ERROR)
                {
                        close_window(wp);
                        if(imagecnt++)
                                add_it();
                        open_window(wp);
                        sprintf(buf, "%s", (bw) ? " Dark" :
"White");
                        print_8x16(buf, xmenu + CHRW * 2, ymenu
+ CHRH, FGDI, BGDI);
                        sprintf(buf, "%d", imagecnt + 1);
                        print_8x16(buf, xmenu + CHRW * 19, ymenu
+ CHRH * 4,FGDI,BGDI);
                        useflag = ERROR;
                }
                break;
        }
    }
}
mk_defect()
{
}

- Table 2 p.128- add_it()
{
        void *malloc();
        int cols, size, fptmp, fpfin;
        unsigned int *tmp, *ptmp, *final, *pfinal;
        unsigned int nbytes = FORDSIZE << 1;

if((tmp = (unsigned int *)malloc(nbytes)) == NULL)
        {
                pr_error(5);
                return(ERROR);
        }
        if((final = (unsigned int *)malloc(nbytes)) == NULL)
        {
                pr_error(5);
                free((void *)tmp);
                return(ERROR);
        }
        if((fptmp = open(tmp_filespec, O_RDWR | O_BINARY,
                                        S_IREAD | S_IWRITE)) ==
ERROR)
        {
                pr_error(0);
                free((void *)tmp);
                free((void *)final);
                return(ERROR);
        }
        if((fpfin = open(fin_filespec, O_RDWR | O_BINARY,
                                        S_IREAD | S_IWRITE)) ==
ERROR)
        {
                pr_error(0);
                free((void *)tmp);
                free((void *)final);
                close(fpfin);
                return(ERROR);
```

```c
            }
            size = (bin_mode == NORMAL_M) ? FORDSIZE : BINSIZE >> 1;
            while(size--)
            {
                    read(fptmp, tmp, nbytes);
                    read(fpfin, final, nbytes);
                    ptmp = tmp;
                    pfinal = final;
                    cols = FORDSIZE;
                    while(cols--)
                    {
                            *pfinal += *ptmp++;
                            pfinal++;
                    }
                    lseek(fpfin, -2048L, SEEK_CUR);

- Table 2 p.129- write(fpfin, final, nbytes);
            }
            close(fptmp);
            close(fpfin);
            free((void *)tmp);
            free((void *)final);
            return(0);
} divide_it(imgcnt)
int imgcnt;
{
            void *malloc();
            int cols, size, fpfin;
            unsigned int *final, *pfinal;
            unsigned int nbytes = FORDSIZE << 1;

if((final = (unsigned int *)malloc(nbytes)) == NULL)
            {
                    pr_error(5);
                    return(ERROR);
            }
            if((fpfin = open(fin_filespec, O_RDWR | O_BINARY,
                                            S_IREAD | S_IWRITE)) ==
ERROR)
            {
                    pr_error(0);
                    free((void *)final);
                    return(ERROR);
            }
            size = (bin_mode == NORMAL_M) ? FORDSIZE : BINSIZE >> 1;
            while(size--)
            {
                    read(fpfin, final, nbytes);
                    pfinal = final;
                    cols = FORDSIZE;
                    while(cols--)
                    {
                            *pfinal /= imgcnt;
                            pfinal++;
                    }
                    lseek(fpfin, -2048L, SEEK_CUR);
                    write(fpfin, final, nbytes);
            }
            close(fpfin);
            free((void *)final);
            return(0);
} define ELPERVOLT (5.81)

- Table 2 p.130-
```

```
get_stdev(fspec, cp)
char *fspec;
struct curwindow *cp;
{
        void *malloc();
        int i, ave, x, y, cols, fp1, ystart, xstart, rows, *buf, *pbuf;
        unsigned long total = 0L, offsetbytes, filelength();
        unsigned int nbytes;
        char chbuf[32];
        static struct genbox box = {XIMAGEBIN + BINSIZE + 8,YIMAGEBIN +
100,27, 5};
        struct genbox *bp;

bp = &box;
        if((fp1 = open(fspec, O_RDWR | O_BINARY, S_IREAD | S_IWRITE)) ==
ERROR)
        {
                pr_error(1);
                return(ERROR);
        }
        nbytes = (filelength(fp1) == 524288L) ? FORDSIZE : FORDSIZE <<
1;
        i = (filelength(fp1) == 524288L) ? 1 : 2;
        if((buf = (int *)malloc(nbytes)) == NULL)
        {
                pr_error(5);
                close(fp1);
                return(ERROR);
        }
        xstart = (cp->xpos < cp->xpos1) ? cp->xpos : cp->xpos1;
        xstart -= XIMAGEBIN;
        xstart *= i;
        x = cols = (abs(cp->xpos - cp->xpos1) + 1) * i;
        ystart = (cp->ypos < cp->ypos1) ? cp->ypos : cp->ypos1;
        ystart -= YIMAGEBIN;
        ystart *= i;
        y = rows = (abs(cp->ypos - cp->ypos1) + 1) * i;

offsetbytes = nbytes * (long)ystart;
        lseek(fp1, offsetbytes, SEEK_SET);
        while(y--)
        {
                read(fp1, buf, nbytes);
                pbuf = buf + xstart;
                x = cols;
                while(x--)
                        total += *pbuf++;
        }
        ave = total / ((long)cols * rows);
        total = 0L;

- Table 2 p.131- lseek(fp1, offsetbytes, SEEK_SET);
        y = rows;
        while(y--)
        {
                read(fp1, buf, nbytes);
                pbuf = buf + xstart;
                x = cols;
                while(x--)
                {
                        i = *pbuf++ - ave;
                        total += (long)i * i;
                }
        }
        total /= ((long)cols * rows);
        open_box(bp);
        x = bp->xpos + (CHRW << 1), y = bp->ypos + CHRH;
        sprintf(chbuf, "Standard Dev   = %6.2f", sqrt((double)total));
```

```
        print_8x16(chbuf, x, y, FGDI, BGDI);
        sprintf(chbuf, "Electrons RMS  = %6.2f", ELPERVOLT *
sqrt((double)total));
        print_8x16(chbuf, x, y += CHRH, FGDI, BGDI);
        sprintf(chbuf, "Average Value = %4d", ave);
        print_8x16(chbuf, x, y += CHRH, FGDI, BGDI);
        get_key();
        close_box(bp);

close(fp1);
        free((void *)buf);
        return;
}
/*****************************************************************
        This function plots the data which is between the two cursors
*****************************************************************/
/*
Tony Scandura              07/21/86        11-18-8602-14-8904-04-90
*/ include "ccd.h"

plot(cp)
struct curwindow *cp;
{
        int i, x, y, dx, dy, number;
        int xstart, ystart, xend, yend;
        static unsigned char databuf[BYTESPERLINE];
        unsigned char *pixdata = databuf;

if(abs(cp->ypos - cp->ypos1) < abs(cp->xpos - cp->xpos1))
        {
                x = cp->xpos;
```

— Table 2 p.132—

```
                y = cp->xpos1;
                i = 1;
        }
        else
        {
                x = cp->ypos;
                y = cp->ypos1;
                i = 0;
        }
        if(x < y)
        {
                xstart = cp->xpos;
                xend = cp->xpos1;
                ystart = cp->ypos;
                yend = cp->ypos1;
        }
        else
        {
                xstart = cp->xpos1;
                xend = cp->xpos;
                ystart = cp->ypos1;
                yend = cp->ypos;
        }
        dx = xend - xstart;
        dy = yend - ystart;

*pixdata++ = rd_px_xy(xstart, ystart);
        if(i)
        {
                for(x = xstart, i = 0; x < xend; x++, i++, pixdata++)
                {
                        y = ystart + ((long)i * dy) / dx;
                        *pixdata = rd_px_xy(x, y);
                        wr_px_xy(x, y, MAXFGDI);
```

```c
                y = MAXVIDEOLINE - *(pixdata - 1);
                if(*pixdata > *(pixdata - 1))
                {
                        number = *pixdata - *(pixdata - 1);
                        while(number--)
                                wr_px_xy(x - 1, y--, MAXFGDI);
                }
                else if(*pixdata < *(pixdata - 1))
                {
                        number = *(pixdata - 1) - (*pixdata);
                        while(number--)
                                wr_px_xy(x - 1, y++, MAXFGDI);
                }
                else
                        wr_px_xy(x - 1, y, MAXFGDI);
        }
}
```

– Table 2 p.133–

```c
        else
        {
                for (y = ystart, i = 0; y < yend; y++, i++, pixdata++)
                {
                        x = xstart + ((long)i * dx) / dy;
                        *pixdata = rd_px_xy(x, y);
                        wr_px_xy(x, y, MAXFGDI);
                        x = *(pixdata - 1);
                        if(*pixdata > *(pixdata - 1))
                        {
                                number = *pixdata - *(pixdata - 1);
                                while(number--)
                                        wr_px_xy(x++, y - 1, MAXFGDI);
                        }
                        else if(*pixdata < *(pixdata - 1))
                        {
                                number = *(pixdata - 1) - (*pixdata);
                                while(number--)
                                        wr_px_xy(x--, y - 1, MAXFGDI);
                        }
                        else
                                wr_px_xy(x, y - 1, MAXFGDI);
                }
        }
}
/******************************************************************
        This function prints out lines of data from the image memory.
        Data can be sent to the CRT, lineprinter, or to a Lotus file.
******************************************************************/
/*
        Tony Scandura    04-04-89         04-06-90
*/ include <stdio.h>
include "ccd.h"
#include "keys.h"

#define XLISTBOX 240
#define YLISTBOX 672
#define XCNT 16
#define YCNT 4
#define XFSPECBOX 324
#define YFSPECBOX 160
#define XERRORBOX 396
define YERRORBOX 320 print_data(cp)
struct curwindow *cp;
{
        int i, x, y, xpr, ypr, xprint, yprint, xcnt, ycnt, line = 1;
```

– Table 2 p.134–

```
        int xstart, ystart, xwidth, cols, rows;
        unsigned char far *pmem, far *xy_to_ad();
        char buf[16];
        static struct genbox box = {XLISTBOX, YLISTBOX, 68, 6};
        struct genbox *bp = &box;

xprint = XLISTBOX + (CHRW << 1);
        yprint = YLISTBOX + CHRH;
        xstart = (cp->xpos < cp->xpos1) ? cp->xpos : cp->xpos1;
        xwidth = abs(cp->xpos - cp->xpos1) + 1;
        ystart = (cp->ypos < cp->ypos1) ? cp->ypos : cp->ypos1;
        rows = abs(cp->ypos - cp->ypos1) + 1;

switch(get_outdevice())
        {
                case 0:
                        open_box(bp);
                        y = ystart;
                        while(rows--)
                        {
                                xpr = xprint, ypr = yprint;
                                sprintf(buf, "Line %d:", line++);
                                print_8x16(buf, xpr, ypr, FGDI, BGDI);
                                ypr += CHRH;
                                xcnt = 0;
                                ycnt = 1;
                                x = xstart;
                                cols = xwidth;
                                while(cols--)
                                {
                                        pmem = xy_to_ad(x++, y);
                                        i = *pmem;
                                        sprintf(buf, "%4d", i);
                                        print_8x16(buf, xpr, ypr, FGDI, BGDI);
                                        xpr += CHRW << 2;
                                        if(++xcnt == XCNT)
                                        {
                                                xcnt = 0;
                                                xpr = xprint;
                                                ypr += CHRH;
                                                if(++ycnt == YCNT)
                                                {
                                                ypr = yprint + CHRH;
                                                ycnt = 1;
                                                get_key();
                                                }
                                        }
                                }
                                if(ycnt != YCNT)
                                {
```

- Table 2 p.135-

```
                                        while(xcnt++ != XCNT)
                                        {
                                                print_8x16("    ", xpr,
ypr, FGDI, BGDI);
                                                xpr += CHRW << 2;
                                        }
                                        while(++ycnt != YCNT)
                                        {
                                                xcnt = 0;
                                                xpr = xprint;
                                                ypr += CHRH;
                                                while(xcnt++ != XCNT)
                                                {
                                                print_8x16("    ", xpr,
ypr, FGDI, BGDI);
                                                xpr += CHRW << 2;
                                                }
```

```
                              }
                      y++;
                      get_key();
              }
              close_box(bp);
              break;
      case 1:
              y = ystart;
              while(rows--)
              {
                      pmem = xy_to_ad(xstart, y++);
                      fprintf(stdprn, "\n\nLine %d:\n",
line++);
                      cols = xwidth;
                      while(cols--)
                      {
                              i = *pmem++;
                              fprintf(stdprn, "%4d", i);
                      }
              }
              fprintf(stdprn, "\f");
              fflush(stdprn);
              break;
      case 2:
              wr_lotus(cp);
              break;
      case ERROR:
              return;
      }
} wr_lotus(cp)
struct curwindow *cp;

- Table 2 p.136-

{
      FILE *stream;
      int i, x, y, radix = 10, line = 1;
      int xstart, ystart, xwidth, rows, cols;
      int xprint = XFSPECBOX + (CHRW << 1), yprint = YFSPECBOX + CHRH;
      unsigned char far *pmem, far *xy_to_ad();
      char *get_filespec(), *itoa(), *pbuf, buf[20];
      static struct genbox fspec_box = {XFSPECBOX, YFSPECBOX, 47, 8};
      static struct genbox error_box = {XERRORBOX, YERRORBOX, 29, 7};
      struct genbox *eb, *fs;
      eb = &error_box;
      fs = &fspec_box;

xstart = (cp->xpos < cp->xpos1) ? cp->xpos : cp->xpos1;
      xwidth = abs(cp->xpos - cp->xpos1) + 1;
      ystart = (cp->ypos < cp->ypos1) ? cp->ypos : cp->ypos1;
      rows = abs(cp->ypos - cp->ypos1) + 1;

x = XERRORBOX + (CHRW << 1);
      y = YERRORBOX + CHRH;
      open_box(fs);
      print_8x16("Enter Filespec For Lotus File:", xprint, yprint,
FGDI, BGDI);
if((stream = fopen(get_filespec(xprint, yprint + (CHRH << 1)),"w")) ==
NULL)
              {
              open_box(eb);
              print_8x16("------- E R R O R -------", x, y, FGDI,
BGDI);
              print_8x16("The File Cannot Be Opened",
                                        x, y += CHRH << 1, FGDI,
BGDI);
              print_8x16("Press ANY Key To Continue",
                                        x, y += CHRH << 1, FGDI,
```

```
BGDI);
                get_key();
                close_box(eb);
                close_box(fs);
                return(ERROR);
        }
        close_box(fs);
        y = ystart;
        while(rows--)
        {
                pmem = xy_to_ad(xstart, y++);
                i = *pmem++;
                pbuf = itoa(i, buf, radix);
                fprintf(stream, "\"Line %d:\" %s\n", line++, pbuf);
                cols = xwidth;
                while(--cols)
                {
```

- Table 2 p.137-

```
                        i = *pmem++;
                        pbuf = itoa(i, buf, radix);
                        fprintf(stream, "\"\" %s\n", pbuf);
                }
        }
        fclose(stream);
        return(0);
}
/******************************************************************
        This function reads the keyboard and returns: 0 if no keys
        have been pressed, or the character if a key has been pressed.
        Extended codes are returned with the high order bit on.
******************************************************************/

/*
        Tony Scandura          07-03-85          10-15-87
*/ include <dos.h>
include <stdio.h> readkey()
{
        int i;

if (kbhit())
        {
                if (i = getch())
                        return (i);
                else
                        return (getch() | 0x80);
        }
        return(0);
} get_key()
{
        int i;

while(!(i = readkey()));
        return(i);
}
/****************************************************
        These functions are for stereotatic imaging
****************************************************/

/*
        Tony Scandura    11-19-91
*/ include <stdio.h>
```

- Table 2 p.138-

```c
#include <math.h>
#include "trident.h"
#include "ccd.h"

#define XINPUT (200)
#define YINPUT (256)
#define XANS (380)
#define YANS (256)
#define PI (3.1415927)

static float f1_ref[3], f2_ref[3], f1_shd[3], f2_shd[3];
static float l1_ref[3], l2_ref[3], l1_shd[3], l2_shd[3];
static float src[3], rot_angle = 30.0 * PI / 180.0;
static double xfin, yfin, zfin;
static float scale, dz, z_pinpt, y_pinpt, angle, c_perp, c_dist;
static int f1i_shd[2], f2i_shd[2];
static int l1i_ref[2], l2i_ref[2], l1i_shd[2], l2i_shd[2];
static int xknife, yknife, y_srcy;
static struct genbox box = {XINPUT, YINPUT, 78, 3};
static struct genbox ansbox = {XANS, YANS, 34, 6};
extern struct curwindow altcursor;
extern char *stereo_filespec, *fin_filespec, *tmp_filespec;
extern int crt_mode, stereo_mode;

get_stereo_settings()
{
        static struct menwindow menu =
        {
                25, 6, " -- Mode Change Menu --", "F1: \xf1 15 Degree Rotation",
                "F2: \xf1 7.5 Degree Rotation", "F3: Recalculate Results",
                "F4: Turn Stereo Mode Off", "F5: Main Menu/No Changes"
        };
        struct menwindow *wp;

wp = &menu;
        switch(get_menu_ptr(wp, TRUE, FALSE))
        {
                case 0:
                        rot_angle = 30.0 * PI / 180.0;
                        break;
                case 1:
                        rot_angle = 15.0 * PI / 180.0;
                        break;
                case 2:
                        calc_results(FALSE);
                        break;
                case 3:
                        stereo_mode = 0;
                        break;

- Table 2 p.139- case 4:
                        break;
        }
} do_stereo()
{
        int i;
        char buf[64], *get_new_name(), *strrchr(), *pchr;
        static struct menwindow menu =
        {
                12, 5, " Select One", "F1: Continue", "F2: Process",
                "F3: Retake", "F4: Abort"
        };
        static struct menwindow menu1 =
        {
                10, 3, "Select One", "F1: Retake", "F2: Abort"
```

```
};
struct menwindow *wp = &menu, *wp1 = &menu1;

clear_image(0);
clear_image(1);
crt_mode = ERROR;
do
        if(int_image(fin_filespec) == ERROR)
        {
                crt_mode = 1;
                return;
        }
while((i = get_menu_ptr(wp, TRUE, FALSE)) == 2);
switch(i)
{
        case 0:
                break;
        case 1:
                chg_contrast();
                break;
        case 3:
                crt_mode = 1;
                return;
                break;
}
crt_mode = 1;
dup_image();
clear_image(0);
copy_image(fin_filespec, tmp_filespec);
crt_mode = ERROR;
do
{
        if(int_image(fin_filespec) == ERROR)
                switch(get_menu_ptr(wp1, TRUE, FALSE))
```

- Table 2 p.140-

```
                {
                        case 0:
                                i = 2;
                                continue;
                        case 1:
                                crt_mode = 1;
                                return;
                }
        i = get_menu_ptr(wp, TRUE, FALSE);
}
while(i == 2);
switch(i)
{
        case 0:
                break;
        case 1:
                chg_contrast();
                break;
        case 3:
                crt_mode = 1;
                return;
                break;
}
calc_results(TRUE);

get_new_name(buf);
pchr = strrchr(buf, '\\');
*(pchr + 1) = '_';
*(pchr + 2) = 'S';
if(exist_file(buf) != ERROR)
        if(copy_image(tmp_filespec, buf) != ERROR)
                save_annotation(buf);

*(pchr + 2) = 'T';
if(exist_file(buf) != ERROR)
```

```c
            If(copy_image(fin_filespec, buf) != ERROR)
                    save_stereo(buf);

crt_mode = 1;
}
calibrate()
{
        static struct menwindow menu =
        {
                19, 7, "  - Calibration -", "F1: Enter Constants",
                        "F2: Scale Factor", "F3: Find Source", "F4: Find
Center",
                        "F5: Save Parameters", "F6: Main Menu"
        };
        struct menwindow *wp = &menu;

- Table 2 p.141- while(1)
        {
                switch(get_menu_ptr(wp, TRUE. FALSE))
                {
                case 0:
                        get_constants();
                        break;
                case 1:
                        get_scale_fact();
                        break;
                case 2:
                        find_source();
                        break;
                case 3:
                        find_center();
                        break;
                case 4:
                        save_calibration();
                        break;
                case 5:
                        return;
                        break;
                }
        }
} get_constants()
{
        int xinput, yinput, xans, yans;
        char buf[80], *gr_gets();
        struct genbox *bp = &box;

xinput = XINPUT + (CHRW << 1);
        yinput = YINPUT + CHRH;
        xans = XANS + (CHRW << 1);
        yans = YANS + CHRH;
        open_box(bp);
        print_8x16("Enter distance from phosphor plane to fiducial
plane: (mm)",
                        xinput, yinput, FGDI, BGDI);
        sscanf(gr_gets(buf, xinput + (59 << 3), yinput, 7), "%f", &dz);
        print_8x16("Enter distance from phosphor plane to fixture
pinpoint: (mm) ",
                        xinput, yinput, FGDI, BGDI);
        sscanf(gr_gets(buf, xinput + (61 << 3), yinput, 7), "%f",
&z_pinpt);
        print_8x16("Enter X and Y coordinates of left fiducial cross
hair: (mm) ",
                        xinput, yinput, FGDI, BGDI);
        sscanf(gr_gets(buf, xinput + (60 << 3), yinput, 13),
                                "%f%*c%f", fl_ref,

- Table 2 p.142-
```

```
f1_ref + 1);
        print_8x16("Enter X and Y coordinates of right fiducial cross
hair: (mm) ",
                          xinput, yinput, FGDI, BGDI);
        sscanf(gr_gets(buf, xinput + (61 << 3), yinput, 13),
                                       "%f%*c%f", f2_ref,
f2_ref + 1);
        print_8x16("Enter a value for P perpendicular and N distance:
(mm)        ",
                          xinput, yinput, FGDI, BGDI);
        sscanf(gr_gets(buf, xinput + (55 << 3), yinput, 13),
                                       "%f%*c%f", &c_perp,
&c_dist);
        close_box(bp);
        bp = &ansbox;
        open_box(bp);
        sprintf(buf, "Phosphor to fiducial =%8.3f",dz);
        print_8x16(buf, xans, yans, FGDI, BGDI);
        sprintf(buf, "Phosphor to pinpoint =%8.3f",z_pinpt);
        print_8x16(buf, xans, yans += CHRH, FGDI, BGDI);
        sprintf(buf, "Fiducial 1 xy =%7.3f,%7.3f", *f1_ref, *(f1_ref +
1));
        print_8x16(buf, xans, yans += CHRH, FGDI, BGDI);
        sprintf(buf, "Fiducial 2 xy =%7.3f,%7.3f", *f2_ref, *(f2_ref +
1));
        print_8x16(buf, xans, yans += CHRH, FGDI, BGDI);
        *(f1_ref + 2) = *(f2_ref + 2) = -dz;
        get_key();
        close_box(bp);
} get_scale_fact()
{
        int i, x1, y1, x2, y2, x3, y3, x4, y4, oldx, oldy;
        int xinput, yinput;
        char buf[64];
        struct curwindow *altcp = &altcursor;
        struct genbox *bp = &box;

xinput = XINPUT + (CHRW << 1);
        yinput = YINPUT + CHRH;
        oldx = altcp->xpos;
        oldy = altcp->ypos;
        altcp->xpos = 145;
        altcp->ypos = 219;
        move_cursor(altcp, TRUE, LEFT_IMG);
        x1 = altcp->xpos;
        y1 = altcp->ypos;
        altcp->xpos = 365;
        altcp->ypos = 219;
        move_cursor(altcp, TRUE, LEFT_IMG);
```

- Table 2 p.143 -

```
        x2 = altcp->xpos;
        y2 = altcp->ypos;
        altcp->xpos = 146;
        altcp->ypos = 439;
        move_cursor(altcp, TRUE, LEFT_IMG);
        x3 = altcp->xpos;
        y3 = altcp->ypos;
        altcp->xpos = 365;
        altcp->ypos = 439;
        move_cursor(altcp, TRUE, LEFT_IMG);
        x4 = altcp->xpos;
        y4 = altcp->ypos;
        if(abs(x3-x1) > 1 || abs(x4-x2) > 1 || abs(y2-y1) > 1 ||
abs(y4-y3) > 1)
                pr_error(11);
        scale = (abs(x2-x1) + abs(x4-x3) + abs(y3-y1) + abs(y4-y2)) /
```

```
112.0;
        open_box(bp);
        sprintf(buf, "The scale factor is: %.3f pixels per milli-meter",
scale);
        print_8x16(buf, xinput + 100, yinput, FGDI, BGDI);
        get_key();
        close_box(bp);
        altcp->xpos = oldx;
        altcp->ypos = oldy;
} find_source()
{
        int xinput, yinput, oldx, oldy;
        struct curwindow *altcp = &altcursor;
        struct genbox *bp = &box;
        char buf[64];

xinput = XINPUT + (CHRW << 1);
        yinput = YINPUT + CHRH;
        oldx = altcp->xpos;
        oldy = altcp->ypos;

altcp->xpos = 8;
        altcp->ypos = 80;
        move_cursor(altcp, TRUE, LEFT_IMG);
        xknife = altcp->xpos;
        yknife = altcp->ypos;
        altcp->xpos = 256;
        altcp->ypos = 144;
        move_cursor(altcp, TRUE, LEFT_IMG);
        *f2i_shd = altcp->xpos;
        *(f2i_shd + 1) = altcp->ypos;
        altcp->xpos = 256;
        altcp->ypos = 512;
```

- Table 2 p.144-

```
        move_cursor(altcp, TRUE, LEFT_IMG);
        *f1i_shd = altcp->xpos;
        *(f1i_shd + 1) = altcp->ypos;
        altcp->xpos = 256;
        altcp->ypos = 328;
        move_cursor(altcp, TRUE, LEFT_IMG);

*f1_shd = (*f1i_shd - xknife) / scale;
        *(f1_shd + 1) = (*(f1i_shd + 1) - yknife) / scale;
        *f2_shd = (*f2i_shd - xknife) / scale;
        *(f2_shd + 1) = (*(f2i_shd + 1) - yknife) / scale;
        *(f1_shd + 2) = *(f2_shd + 2) = 0.0;
        y_pinpt = (altcp->ypos - yknife) / scale;

altcp->xpos = oldx;
        altcp->ypos = oldy;
        calc_pos(*f1_shd, *(f1_shd + 1), *(f1_shd + 2),
                *f1_ref, *(f1_ref + 1), *(f1_ref + 2),
                *f2_shd, *(f2_shd + 1), *(f2_shd + 2),
                *f2_ref, *(f2_ref + 1), *(f2_ref + 2), src);
        open_box(bp);
        sprintf(buf, "The X-Ray source coordinates are: (%.3f, %.3f,
%.3f)",
                                        *src, *(src + 1), *(src
+ 2));
        print_8x16(buf, xinput + 60, yinput, FGDI, BGDI);
        get_key();
        close_box(bp);
        open_box(bp);
        y_srcy = *(src + 1) * scale + yknife + 0.5;
        sprintf(buf, "The Y cursor value for locating pinpoint is: %d",
```

```
y_srcy);
        print_8x16(buf, xinput + 104, yinput, FGDI, BGDI);
        get_key();
        close_box(bp);
} find_center()
{
        int xinput, yinput, xans, yans;
        char buf[80], *gr_gets();
        float tmp1, tmp2;
        struct genbox *bp = &box;

xinput = XINPUT + (CHRW << 1);
        yinput = YINPUT + CHRH;
        xans = XANS + (CHRW << 1);
        yans = YANS + CHRH;
        open_box(bp);
        print_8x16("Enter angle for which the pinpoint coincides with Y
origin:",
```

- Table 2 p.145-

```
                                xinput, yinput, FGDI, BGDI);
        sscanf(gr_gets(buf, xinput + (60 << 3), yinput, 6), "%f",
&angle);
        close_box(bp);
        if(angle != 0)
        {
                angle *= PI / 180.0;
                tmp2 = y_pinpt - *(src + 1);
                tmp1 = fabs(tmp2) * (z_pinpt - *(src + 2)) / (angle *
-(*(src + 2)));
                c_perp = tmp1 * angle / 2;
                if(tmp2 < 0.0)
                        c_perp *= -1.0;
                c_dist = z_pinpt - tmp1;
        }
        bp = &ansbox;
        open_box(bp);
        sprintf(buf, "Rotation angle pinpt =%8.3f", angle * 180.0 / PI);
        print_8x16(buf, xans, yans, FGDI, BGDI);
        sprintf(buf, "Cnt perp to src perp =%8.3f",c_perp);
        print_8x16(buf, xans, yans += CHRH + 8, FGDI, BGDI);
        sprintf(buf, "Cnt perp dist to ori =%8.3f", c_dist);
        print_8x16(buf, xans, yans += CHRH + 8, FGDI, BGDI);
        get_key();
        close_box(bp);
} save_calibration()
{
        FILE *stream;

if((stream = fopen(stereo_filespec, "w")) == NULL)
        {
                pr_error(0);
                return(ERROR);
        }
        fprintf(stream,
                "%f %f %f %f %f %f %f %f %f %f %f %f %f %f %f %f %f %f
%f %f %f %f",
                        *f1_ref, *(f1_ref + 1), *(f1_ref + 2), *f2_ref,
*(f2_ref + 1),
                        *(f2_ref + 2), *f1_shd, *(f1_shd + 1), *(f1_shd
+ 2), *f2_shd,
                        *(f2_shd + 1), *(f2_shd + 2), *src, *(src + 1),
*(src + 2),
                        scale, dz, z_pinpt, y_pinpt, angle, c_perp,
c_dist);
        fprintf(stream, " %i %i %i %i %i %i %i",
                        *f1i_shd, *(f1i_shd + 1), *f2i_shd, *(f2i_shd +
```

```
1),
                    xknife, yknife, y_srcy);

- Table 2 p.146- fclose(stream);
        return(0);
} rec_calibration()
{
        FILE *stream;

if((stream = fopen(stereo_filespec, "r")) == NULL)
        {
                pr_error(0);
                return(ERROR);
        }
        fscanf(stream,
                "%f %f %f %f %f %f %f %f %f %f %f %f %f %f %f %f %f %f
%f %f %f %f",
                        f1_ref, f1_ref + 1, f1_ref + 2, f2_ref, f2_ref + 1,
f2_ref + 2, f1_shd,
                        f1_shd + 1, f1_shd + 2, f2_shd, f2_shd + 1, f2_shd + 2,
src, src + 1,
                        src + 2, &scale, &dz, &z_pinpt, &y_pinpt, &angle,
&c_perp, &c_dist);
        fscanf(stream, " %i %i %i %i %i %i %i",
                        f1i_shd, f1i_shd + 1, f2i_shd, f2i_shd + 1, &xknife,
&yknife, &y_srcy);
        fclose(stream);
        return(0);
} calc_xyz()
{
        float tmp1, tmp2, buf1[3], buf0[3];
        double tx();

tmp1 = 2 * sin(rot_angle / 2.0) * hypot(c_dist, c_perp);
        tmp2 = rot_angle / 2.0 + asin(c_perp / hypot(c_dist, c_perp));
        calc_pos(*l1_shd, *(l1_shd + 1), *(l1_shd + 2), 0.0, 0.0, *(src
+ 2),
                tx(1.0, 0.0, 0.0, *l2_shd, *(l2_shd + 1), *(l2_shd + 2), 0.0),
                tx(0.0, cos(rot_angle), cos(PI / 2.0 + rot_angle), *l2_shd,
*(l2_shd + 1),
                        *(l2_shd + 2), -tmp1 * cos(tmp2)),
                tx(0.0, cos(3.0 * PI / 2.0 + rot_angle), cos(rot_angle),
*l2_shd,
                        *(l2_shd + 1), *(l2_shd +2), -tmp1 * sin(tmp2)),
                tx(1.0, 0.0, 0.0, 0.0, 0.0, *(src + 2), 0.0),
                tx(0.0, cos(rot_angle), cos(PI / 2.0 + rot_angle), 0.0, 0.0,
*(src + 2),
                        -tmp1 * cos(tmp2)),
                tx(0.0, cos(3 * PI / 2 + rot_angle), cos(rot_angle), 0.0,
                        0.0, *(src + 2), -tmp1 * sin(tmp2)), buf1);

- Table 2 p.147- calc_pos(*l1_ref, *(l1_ref + 1), *(l1_ref + 2), 0.0, 0.0, *(src
+ 2),
                tx(1.0, 0.0, 0.0, *l2_ref, *(l2_ref + 1), *(l2_ref +2), 0.0),
                tx(0.0, cos(rot_angle), cos(PI / 2.0 + rot_angle), *l2_ref,
*(l2_ref + 1),
                        *(l2_ref + 2), -tmp1 * cos(tmp2)),
                tx(0.0, cos(3.0 * PI / 2.0 + rot_angle), cos(rot_angle),
*l2_ref,
                        *(l2_ref + 1), *(l2_ref + 2), -tmp1 * sin(tmp2)),
                tx(1.0, 0.0, 0.0, 0.0, 0.0, *(src + 2), 0.0),
                tx(0.0, cos(rot_angle), cos(PI / 2.0 + rot_angle), 0.0, 0.0,
```

```
                  *(src + 2),
                         -tmp1 * cos(tmp2)),
                 tx(0.0, cos(3.0 * PI / 2.0 + rot_angle), cos(rot_angle), 0.0,
                         0.0, *(src + 2), -tmp1 * sin(tmp2)), buf0);

yfin = tx(1.0, 0.0, 0.0, *buf1 - *buf0, *(buf1 + 1) - *(buf0 +
1),
                         *(buf1 + 2) - *(buf0 + 2), 0.0) * -1.0 -
2.0;
        xfin = tx(0.0, cos(rot_angle / 2.0), cos(3.0 * PI / 2.0 +
rot_angle / 2.0),
                         *buf1 - *buf0, *(buf1 + 1) - *(buf0 + 1), *(buf1
+ 2) - *(buf0 +2),
                         0.0);
        zfin = tx(0.0, cos(PI / 2.0 + rot_angle / 2.0), cos(rot_angle /
2.0),
                         *buf1 - *buf0, *(buf1 + 1) - *(buf0 + 1), *(buf1
+ 2) - *(buf0 +2),
                         0.0);
} double tx(l1, l2, l3, x, y, z, x0)
double l1, l2, l3, x, y, z, x0;
{
        return(l1 * x + l2 * y + l3 * z + x0);
} calc_pos(x1, y1, z1, x2, y2, z2, x3, y3, z3, x4, y4, z4, buffer)
double x1, y1, z1, x2, y2, z2, x3, y3, z3, x4, y4, z4;
float *buffer;
{
        float c1, c2, t1, t2, u1, u2, j, k;

c1 = -(x2-x1) * (x1 - x3) - (y2 - y1) * (y1 - y3) - (z2 - z1) *
(z1 - z3);
        c2 = -(x4-x3) * (x1 - x3) - (y4 - y3) * (y1 - y3) - (z4 - z3) *
(z1 - z3);
        t1 = (x2-x1) * (x2 - x1) + (y2 - y1) * (y2 - y1) + (z2 - z1) *
(z2 - z1);
        t2 = (x2-x1) * (x4 - x3) + (y2 - y1) * (y4 - y3) + (z2 - z1) *
```

– Table 2 p.148 –

```
(z4 - z3);
        u1 = -(x4-x3) * (x2 - x1) - (y4 - y3) * (y2 - y1) - (z4 - z3) *
(z2 - z1);
        u2 = -(x4-x3) * (x4 - x3) - (y4 - y3) * (y4 - y3) - (z4 - z3) *
(z4 - z3);
        j = (c1 * u2 - c2 * u1) / (t1 * u2 - t2 * u1);
        k = (t1 * c2 - t2 * c1) / (t1 * u2 - t2 * u1);

*buffer++ = (x1 + j * (x2 - x1) + x3 + k * (x4 - x3)) / 2;
        *buffer++ = (y1 + j * (y2 - y1) + y3 + k * (y4 - y3)) / 2;
        *buffer   = (z1 + j * (z2 - z1) + z3 + k * (z4 - z3)) / 2;
} save_stereo(fspec)
char *fspec;
{
        FILE *stream;
        char buffer[64], *strcat();

sscanf(fspec, "%[^.]", buffer);
        strcat(buffer, ".ste");
        if((stream = fopen(buffer, "w")) == NULL)
        {
                pr_error(0);
                return(ERROR);
        }
        fprintf(stream, "%d %d %d %d %d %d %d %d %f %f %f",
                                *l1i_ref, *(l1i_ref + 1),
*l2i_ref, *(l2i_ref + 1),
                                        *l1i_shd, *(l1i_shd + 1),
```

```
         *12i_shd, *(12i_shd + 1),
                                                    xfin, yfin, zfin);
              fclose(stream);
              return(0);
} rec_stereo(fspec)
char *fspec;
{
         FILE *stream;
         char buffer[64], *strcat();
         int i, fp;

sscanf(fspec, "%[^.]", buffer);
         strcat(buffer, ".ste");
         if((stream = fopen(buffer, "r")) == NULL)
         {
              pr_error(0);
              return(ERROR);
         }
         fscanf(stream, "%d %d %d %d %d %d %d %d %f %f %f",

- Table 2 p.149-

11i_ref, 11i_ref + 1, 12i_ref,
12i_ref + 1,
                                                    11i_shd, 11i_shd + 1, 12i_shd,
12i_shd + 1,
                                                    &xfin, &yfin, &zfin);
              fclose(stream);
              return(0);
} pr_stereo_result()
{
         int xans = 676, yans = 0;
         char buf[64];
         struct genbox *bp = &box;

bp = &ansbox;
         sprintf(buf, "Final X value =%8.3f", xfin);
         print_8x16(buf, xans, yans, FGDI, 0);
         sprintf(buf, "Final Y value =%8.3f", yfin);
         print_8x16(buf, xans, yans += CHRH + 8, FGDI, 0);
         sprintf(buf, "Final Z value =%8.3f", zfin);
         print_8x16(buf, xans, yans += CHRH + 8, FGDI, 0);
         wr_cur_dot(*11i_ref, *(11i_ref + 1));
         wr_cur_dot(*12i_ref + BINSIZE, *(12i_ref + 1));
         wr_cur_dot(*11i_shd, *(11i_shd + 1));
         wr_cur_dot(*12i_shd + BINSIZE, *(12i_shd + 1));
} calc_results(ref_flag)
int ref_flag;
{
         int i, oldx, oldy;
         struct curwindow *altcp = &altcursor;

oldx = altcp->xpos;
         oldy = altcp->ypos;
         if(ref_flag)
         {
              altcp->xpos = XIMAGEBIN + 493;
              altcp->ypos = YIMAGEBIN + 256;
              move_cursor(altcp, FALSE, LEFT_IMG);
              *11i_ref = altcp->xpos;
              *(11i_ref + 1) = altcp->ypos;
         }
         altcp->xpos = XIMAGEBIN + 256;
         altcp->ypos = YIMAGEBIN + 256;
         move_cursor(altcp, FALSE, LEFT_IMG);
         *11i_shd = altcp->xpos;
```

```
        *(11i_shd + 1) = altcp->ypos;
        if(ref_flag)
        {
```

- Table 2 p.150-

```
                altcp->xpos = XIMAGEBIN + 1005;
                altcp->ypos = YIMAGEBIN + 256;
                move_cursor(altcp, FALSE, RIGHT_IMG);
                *l2i_ref = altcp->xpos - BINSIZE;
                *(l2i_ref + 1) = altcp->ypos;
        }
        altcp->xpos = XIMAGEBIN + 768;
        altcp->ypos = YIMAGEBIN + 256;
        move_cursor(altcp, FALSE, RIGHT_IMG);
        *l2i_shd = altcp->xpos - BINSIZE;
        *(l2i_shd + 1) = altcp->ypos;

*l1_shd = (*l1i_shd - xknife) / scale - *src;
        *(l1_shd + 1) = (*(l1i_shd + 1) - yknife) / scale - *(src + 1);
        *l2_shd = (*l2i_shd - xknife) / scale - *src;
        *(l2_shd + 1) = (*(l2i_shd + 1) - yknife) / scale - *(src + 1);
        *l1_ref = (*l1i_ref - xknife) / scale - *src;
        *(l1_ref + 1) = (*(l1i_ref + 1) - yknife) / scale - *(src + 1);
        *l2_ref = (*l2i_ref - xknife) / scale - *src;
        *(l2_ref + 1) = (*(l2i_ref + 1) - yknife) / scale - *(src + 1);
        *(l1_shd + 2) = *(l2_shd + 2) = *(l1_ref + 2) = *(l2_ref + 2) =
0.0;

calc_xyz();
        pr_stereo_result();

altcp->xpos = oldx;
        altcp->ypos = oldy;
}
/******************************************************************
*
        Collection of BIOS routines to communicate with the video
display
******************************************************************
/

/*
        Tony Scandura            10-25-90
*/ include <dos.h>
include "trident.h"

cursor(column, row)
int column, row;
{
        union REGS inregs;

inregs.h.ah = 0x02;
        inregs.h.bh = 0;
        inregs.h.dh = row;
```

- Table 2 p.151-

```
        inregs.h.dl = column;

int86(0x10, &inregs, &inregs);
} reset_vid_mode()
{
        set_vid_mode(get_vid_mode());
} clscreen()
{
        union REGS inregs, outregs;
```

```
        cursor(0,0);
        inregs.h.ah = 0x09;
        inregs.h.al = 0x20;
        inregs.x.bx = 0x0007;
        inregs.x.cx = 2000;

int86(0x10, &inregs, &outregs);
} blink(pstring)
char *pstring;
{
        wr_ch_atr(pstring, BLINK, 0);
} wr_tty(pstring, intensity)
char *pstring;
int intensity;
{
        union REGS inregs, outregs;

inregs.h.ah = 0x0e;
        inregs.h.bh = 0;
        inregs.h.bl = intensity;

while(inregs.h.al = *pstring++)
                int86(0x10, &inregs, &outregs);
}

/*
        fgnd_int:       foreground (graphics)(if bit 7 = 1 XORed, except
256 color)
                                attribute (text)
        bgrd_int:       background (256 color)
                                video page (all others) (background = 0
in other graphic modes)

- Table 2 p.152-

*/
wr_ch_atr(pstring, fgnd_int, bgrd_int)
char *pstring;
int fgnd_int, bgrd_int;
{
        union REGS inregs, outregs;
        int row, column;

inregs.h.ah = 0x03;
        inregs.h.bh = 0x00;
        int86(0x10, &inregs, &outregs);
        row = outregs.h.dh;
        column = outregs.h.dl;

inregs.h.bh = bgrd_int;
        inregs.h.bl = fgnd_int;
        inregs.x.cx = 1;

while(inregs.h.al = *pstring++)
        {
                switch(inregs.h.al)
                {
                        case '\b':
                        case '\r':
                        case '\n':
                                inregs.h.ah = 0x0e;
                                int86(0x10, &inregs, &outregs);
                                inregs.h.ah = 0x03;
                                inregs.h.bh = 0x00;
                                int86(0x10, &inregs, &outregs);
                                row = outregs.h.dh;
                                column = outregs.h.dl;
                                break;
```

```
                default:
                        inregs.h.ah = 0x09;
                        int86(0x10, &inregs, &outregs);
                        cursor(++column, row);
                }
        }
} wr_one_ch(achar, number, fgnd_int, bgrd_int)
char achar;
int number, fgnd_int, bgrd_int;
{
        union REGS inregs, outregs;
        int row, column;

inregs.h.ah = 0x03;
        inregs.h.bh = 0x00;
        int86(0x10, &inregs, &outregs);

- Table 2 p.153- row = outregs.h.dh;
        column = outregs.h.dl;

inregs.h.bh = bgrd_int;
        inregs.h.bl = fgnd_int;
        inregs.x.cx = number;
        inregs.h.al = achar;
        switch(inregs.h.al)
        {
                case '\b':
                case '\r':
                case '\n':
                        inregs.h.ah = 0x0e;
                        int86(0x10, &inregs, &outregs);
                        break;
                default:
                        inregs.h.ah = 0x09;
                        int86(0x10, &inregs, &outregs);
                        cursor(++column, row);
        }
}
get_vid_mode()
{
        union REGS inregs;

inregs.h.ah = 0x0f;
        int86(0x10, &inregs, &inregs);
        return(inregs.h.al);
} set_gs_summing(disable)
int disable;
{
        union REGS inregs;

inregs.h.ah = 0x12;
        inregs.h.bl = 0x33;
        inregs.h.al = disable;
        int86(0x10, &inregs, &inregs);
} set_df_pallet(disable)
int disable;
{
        union REGS inregs;

inregs.h.ah = 0x12;
        inregs.h.bl = 0x31;
        inregs.h.al = disable;
        int86(0x10, &inregs, &inregs);

- Table 2 p.154-
```

```
} set_vid_mode(mode)
int mode;
{
        union REGS inregs;

inregs.h.ah = 0x00;
        inregs.h.al = mode;
        int86(0x10, &inregs, &inregs);
} reset_grayscales()
{
        int i;
        union REGS inregs;
        unsigned char buf[768];
        unsigned char far *pbuf;
        struct SREGS segregs;

pbuf = buf;
        for(i = 0; i < 256; i++)
        {
                *pbuf++ = i >> 2;
                *pbuf++ = i >> 2;
                *pbuf++ = i >> 2;
        }
        pbuf = buf;
        load_grayscale(pbuf);
}
/*      BIOS versions - Too slow set_vid_seg(segment)
int segment;
{
        union REGS inregs;

inregs.x.ax = 0x007f;
        inregs.h.bh = 0x09;
        inregs.h.bl = segment;
        int86(0x10, &inregs, &inregs);
} load_grayscale(pbuf)
unsigned char far *pbuf;
{
        union REGS inregs;
        struct SREGS segregs;

inregs.h.ah = 0x10;
        inregs.h.al = 0x12;
```

- Table 2 p.155-

```
        inregs.x.bx = 0x0000;
        inregs.x.cx = 0x0100;
        inregs.x.dx = FP_OFF(pbuf);
        segregs.es = FP_SEG(pbuf);
        int86(0x10, &inregs, &inregs);
}
*/
/************************************************************
        This program implements the cursor readout function
************************************************************/

/*
        Tony Scandura            03/07/90
*/ include <stdio.h>
include "ccd.h"
#include "keys.h"
```

```c
#define CUR_AVE_SIZE (9)
#define CURSOR_HLUM (200)
#define CURSOR_LLUM (8)
#define XCURBOX (XIMAGEBIN + BINSIZE + 8)
#define YCURBOX (YDISPLAYPOS)
#define XCURSORMAX (XIMAGEBIN + BINSIZE - 5)
#define YCURSORMAX (YIMAGEBIN + BINSIZE - 5)
#define XCURSORMIN (XIMAGEBIN + 4)
#define YCURSORMIN (YIMAGEBIN + 4)

extern struct curwindow altcursor;
extern int mincontrast, maxcontrast, invert_flag;

xycursor(cp)
struct curwindow *cp;
{
        static struct menwindow menu =
        {
                22, 5, "   - Cursor  Menu -", "F1: Read Single Pixel",
                "F2: Read Average Of 9", "F3: Region Of Interest", "F4:   - Main  Menu -"
        };
        struct menwindow *wp;
        struct curwindow *altcp;

wp = &menu;
        altcp = &altcursor;

while(1)
        {
                switch(get_menu_ptr(wp, TRUE, FALSE))
                {

- Table 2 p.156- case 0:
                                altcp->ave = FALSE;
                                move_cursor(altcp, TRUE, LEFT_IMG);
                                wr_cursor(altcp->pixdata[0], altcp->xpos, altcp->ypos);
                                break;
                        case 1:
                                altcp->ave = TRUE;
                                move_cursor(altcp, TRUE, LEFT_IMG);
                                wr_cursor(altcp->pixdata[0], altcp->xpos, altcp->ypos);
                                break;
                        case 2:
                                region_of_int(cp);
                                break;
                        case 3:
                        case 4:
                                return;
                                break;
                }
        }
} move_cursor(cp, print_flag, lr)
struct curwindow *cp;
int print_flag, lr;
{
        int i, prev_key, nrepeats, increment, value, realvalue, maxmin;
        int xprint = XCURBOX + (CHRW << 1), yprint = YCURBOX + CHRH, xmax, xmin;
        char buffer[32];
        static struct genbox box = {XCURBOX, YCURBOX, 34, 3};
        struct genbox *bp;
        bp = &box;

xmin = (lr) ? XCURSORMIN + BINSIZE : XCURSORMIN;
        xmax = (lr) ? XCURSORMAX + BINSIZE : XCURSORMAX;
        rd_cursor(cp->pixdata[0], cp->xpos, cp->ypos);
```

```c
        if(print_flag)
        {
                open_box(bp);
                value = cursor_value(cp->pixdata[0], cp->ave);
                maxmin = maxcontrast - mincontrast + 1;
                realvalue = (invert_flag) ? 255 - value : value;
                realvalue = ((long)realvalue * maxmin) / 255L +
mincontrast;
                sprintf(buffer, "Pixel at %3d, %3d = %3d (%4d)",
                                                cp->xpos, cp->ypos,
value, realvalue);
                print_8x16(buffer, xprint, yprint, FGDI, BGDI);
        }
```

- Table 2 p.157-

```c
        wr_cur_dot(cp->xpos, cp->ypos);

while ((i = get_key()) != '\r')
        {
                if(i == prev_key)
                        increment = (nrepeats++ > 10) ? 8 : 4;
                else
                {
                        increment = 4;
                        nrepeats = 0;
                }
                prev_key = i;
                wr_cursor(cp->pixdata[0], cp->xpos, cp->ypos);
                switch (i)
                {
                        case UP_ARROW:
                                cp->ypos--;
                                break;
                        case DOWN_ARROW:
                                cp->ypos++;
                                break;
                        case RIGHT_ARROW:
                                cp->xpos++;
                                break;
                        case LEFT_ARROW:
                                cp->xpos--;
                                break;
                        case PG_UP:
                                cp->xpos++, cp->ypos--;
                                break;
                        case PG_DOWN:
                                cp->xpos++, cp->ypos++;
                                break;
                        case HOME_KEY:
                                cp->xpos--, cp->ypos--;
                                break;
                        case END_KEY:
                                cp->xpos--, cp->ypos++;
                                break;
                        case '6':
                                cp->xpos += increment;
                                break;
                        case '4':
                                cp->xpos -= increment;
                                break;
                        case '2':
                                cp->ypos += increment;
                                break;
                        case '8':
                                cp->ypos -= increment;
                                break;
```

- Table 2 p.158-

```
                        case '9':
                                cp->ypos -= increment, cp->xpos += increment;
                                break;
                        case '3':
                                cp->ypos += increment, cp->xpos += increment;
                                break;
                        case '7':
                                cp->ypos -= increment, cp->xpos -= increment;
                                break;
                        case '1':
                                cp->ypos += increment, cp->xpos -= increment;
                                break;
                }
                cp->xpos = (cp->xpos < xmin) ? xmin : cp->xpos;
                cp->xpos = (cp->xpos > xmax) ? xmax : cp->xpos;
                cp->ypos = (cp->ypos < YCURSORMIN) ? YCURSORMIN : cp->ypos;
                cp->ypos = (cp->ypos > YCURSORMAX) ? YCURSORMAX : cp->ypos;

rd_cursor(cp->pixdata[0], cp->xpos, cp->ypos);
                wr_cur_dot(cp->xpos, cp->ypos);
                if(print_flag)
                {
                        value = cursor_value(cp->pixdata[0], cp->ave);
                        realvalue = (invert_flag) ? 255 - value : value;
                        realvalue = ((long)realvalue * maxmin) / 255L + mincontrast;
                        sprintf(buffer, "Pixel at %3d, %3d = %3d (%4d)",
                                                cp->xpos, cp->ypos, value, realvalue);
                        print_8x16(buffer, xprint, yprint, FGDI, BGDI);
                }
        }
        if(print_flag)
                close_box(bp);
} wr_cursor(cursor_data, x, y)
int *cursor_data;
int x, y;
{
        wr_px_xy (x++, y, *cursor_data++);
        wr_px_xy (x, y++, *cursor_data++);
        wr_px_xy (x--, y, *cursor_data++);
        wr_px_xy (x--, y, *cursor_data++);
        wr_px_xy (x, y--, *cursor_data++);
        wr_px_xy (x, y--, *cursor_data++);
```

- Table 2 p.159-

```
        wr_px_xy (x++, y, *cursor_data++);
        wr_px_xy (x++, y, *cursor_data++);
        wr_px_xy (x--, y--, *cursor_data++);
        wr_px_xy (x, y, *cursor_data++);
        wr_px_xy (x += 2, y, *cursor_data++);
        wr_px_xy (x, y += 2, *cursor_data++);
        wr_px_xy (x, y += 2, *cursor_data++);
        wr_px_xy (x -= 2, y, *cursor_data++);
        wr_px_xy (x -= 2, y, *cursor_data++);
        wr_px_xy (x, y -= 2, *cursor_data++);
        wr_px_xy (x, y -= 2, *cursor_data++);
        wr_px_xy (x += 2, --y, *cursor_data++);
        wr_px_xy (x += 3, y, *cursor_data++);
        wr_px_xy (x, y += 3, *cursor_data++);
        wr_px_xy (x, y += 3, *cursor_data++);
        wr_px_xy (x -= 3, y, *cursor_data++);
        wr_px_xy (x -= 3, y, *cursor_data++);
        wr_px_xy (x, y -= 3, *cursor_data++);
```

```
        wr_px_xy (x, y -= 3, *cursor_data++);
        wr_px_xy (x += 3, --y, *cursor_data++);
        wr_px_xy (x += 4, y, *cursor_data++);
        wr_px_xy (x, y += 4, *cursor_data++);
        wr_px_xy (x, y += 4, *cursor_data++);
        wr_px_xy (x -= 4, y, *cursor_data++);
        wr_px_xy (x -= 4, y, *cursor_data++);
        wr_px_xy (x, y -= 4, *cursor_data++);
        wr_px_xy (x, y -= 4, *cursor_data++);
        wr_px_xy (x += 4, --y, *cursor_data++);
        wr_px_xy (x += 5, y, *cursor_data++);
        wr_px_xy (x, y += 5, *cursor_data++);
        wr_px_xy (x, y += 5, *cursor_data++);
        wr_px_xy (x -= 5, y, *cursor_data++);
        wr_px_xy (x -= 5, y, *cursor_data++);
        wr_px_xy (x, y -= 5, *cursor_data++);
        wr_px_xy (x, y -= 5, *cursor_data++);
        wr_px_xy (x += 5, --y, *cursor_data++);
        wr_px_xy (x += 6, y, *cursor_data++);
        wr_px_xy (x, y += 6, *cursor_data++);
        wr_px_xy (x, y += 6, *cursor_data++);
        wr_px_xy (x -= 6, y, *cursor_data++);
        wr_px_xy (x -= 6, y, *cursor_data++);
        wr_px_xy (x, y -= 6, *cursor_data++);
        wr_px_xy (x, y -= 6, *cursor_data++);
} rd_cursor(cursor_data, x, y)
int *cursor_data;
int x, y;
{
        *cursor_data++ = rd_px_xy (x++, y);
        *cursor_data++ = rd_px_xy (x, y++);
```

- Table 2 p.160 -

```
        *cursor_data++ = rd_px_xy (x--, y);
        *cursor_data++ = rd_px_xy (x--, y);
        *cursor_data++ = rd_px_xy (x, y--);
        *cursor_data++ = rd_px_xy (x, y--);
        *cursor_data++ = rd_px_xy (x++, y);
        *cursor_data++ = rd_px_xy (x++, y);
        *cursor_data++ = rd_px_xy (x--, y--);
        *cursor_data++ = rd_px_xy (x, y);
        *cursor_data++ = rd_px_xy (x += 2, y);
        *cursor_data++ = rd_px_xy (x, y += 2);
        *cursor_data++ = rd_px_xy (x, y += 2);
        *cursor_data++ = rd_px_xy (x -= 2, y);
        *cursor_data++ = rd_px_xy (x -= 2, y);
        *cursor_data++ = rd_px_xy (x, y -= 2);
        *cursor_data++ = rd_px_xy (x, y -= 2);
        *cursor_data++ = rd_px_xy (x += 2, --y);
        *cursor_data++ = rd_px_xy (x += 3, y);
        *cursor_data++ = rd_px_xy (x, y += 3);
        *cursor_data++ = rd_px_xy (x, y += 3);
        *cursor_data++ = rd_px_xy (x -= 3, y);
        *cursor_data++ = rd_px_xy (x -= 3, y);
        *cursor_data++ = rd_px_xy (x, y -= 3);
        *cursor_data++ = rd_px_xy (x, y -= 3);
        *cursor_data++ = rd_px_xy (x += 3, --y);
        *cursor_data++ = rd_px_xy (x += 4, y);
        *cursor_data++ = rd_px_xy (x, y += 4);
        *cursor_data++ = rd_px_xy (x, y += 4);
        *cursor_data++ = rd_px_xy (x -= 4, y);
        *cursor_data++ = rd_px_xy (x -= 4, y);
        *cursor_data++ = rd_px_xy (x, y -= 4);
        *cursor_data++ = rd_px_xy (x, y -= 4);
        *cursor_data++ = rd_px_xy (x += 4, --y);
        *cursor_data++ = rd_px_xy (x += 5, y);
        *cursor_data++ = rd_px_xy (x, y += 5);
        *cursor_data++ = rd_px_xy (x, y += 5);
        *cursor_data++ = rd_px_xy (x -= 5, y);
```

```c
        *cursor_data++ = rd_px_xy (x -= 5, y);
        *cursor_data++ = rd_px_xy (x, y -= 5);
        *cursor_data++ = rd_px_xy (x, y -= 5);
        *cursor_data++ = rd_px_xy (x += 5, --y);
        *cursor_data++ = rd_px_xy (x += 6, y);
        *cursor_data++ = rd_px_xy (x, y += 6);
        *cursor_data++ = rd_px_xy (x, y += 6);
        *cursor_data++ = rd_px_xy (x -= 6, y);
        *cursor_data++ = rd_px_xy (x -= 6, y);
        *cursor_data++ = rd_px_xy (x, y -= 6);
        *cursor_data++ = rd_px_xy (x, y -= 6);
} wr_cur_dot(x, y)
int x, y;
```

- Table 2 p.161 -

```c
{
        wr_px_xy (x++, y, CURSOR_HLUM);
        wr_px_xy (x, y++, CURSOR_LLUM);
        wr_px_xy (x--, y, CURSOR_HLUM);
        wr_px_xy (x--, y, CURSOR_LLUM);
        wr_px_xy (x, y--, CURSOR_HLUM);
        wr_px_xy (x, y--, CURSOR_LLUM);
        wr_px_xy (x++, y, CURSOR_HLUM);
        wr_px_xy (x++, y, CURSOR_LLUM);
        wr_px_xy (x--, y--, CURSOR_HLUM);
        wr_px_xy (x, y, CURSOR_LLUM);
        wr_px_xy (x += 2, y, CURSOR_HLUM);
        wr_px_xy (x, y += 2, CURSOR_LLUM);
        wr_px_xy (x, y += 2, CURSOR_HLUM);
        wr_px_xy (x -= 2, y, CURSOR_LLUM);
        wr_px_xy (x -= 2, y, CURSOR_HLUM);
        wr_px_xy (x, y -= 2, CURSOR_LLUM);
        wr_px_xy (x, y -= 2, CURSOR_HLUM);
        wr_px_xy (x += 2, --y, CURSOR_LLUM);
        wr_px_xy (x += 3, y, CURSOR_HLUM);
        wr_px_xy (x, y += 3, CURSOR_LLUM);
        wr_px_xy (x, y += 3, CURSOR_HLUM);
        wr_px_xy (x -= 3, y, CURSOR_LLUM);
        wr_px_xy (x -= 3, y, CURSOR_HLUM);
        wr_px_xy (x, y -= 3, CURSOR_LLUM);
        wr_px_xy (x, y -= 3, CURSOR_HLUM);
        wr_px_xy (x += 3, --y, CURSOR_LLUM);
        wr_px_xy (x += 4, y, CURSOR_HLUM);
        wr_px_xy (x, y += 4, CURSOR_LLUM);
        wr_px_xy (x, y += 4, CURSOR_HLUM);
        wr_px_xy (x -= 4, y, CURSOR_LLUM);
        wr_px_xy (x -= 4, y, CURSOR_HLUM);
        wr_px_xy (x, y -= 4, CURSOR_LLUM);
        wr_px_xy (x, y -= 4, CURSOR_HLUM);
        wr_px_xy (x += 4, --y, CURSOR_LLUM);
        wr_px_xy (x += 5, y, CURSOR_HLUM);
        wr_px_xy (x, y += 5, CURSOR_LLUM);
        wr_px_xy (x, y += 5, CURSOR_HLUM);
        wr_px_xy (x -= 5, y, CURSOR_LLUM);
        wr_px_xy (x -= 5, y, CURSOR_HLUM);
        wr_px_xy (x, y -= 5, CURSOR_LLUM);
        wr_px_xy (x, y -= 5, CURSOR_HLUM);
        wr_px_xy (x += 5, --y, CURSOR_LLUM);
        wr_px_xy (x += 6, y, CURSOR_HLUM);
        wr_px_xy (x, y += 6, CURSOR_LLUM);
        wr_px_xy (x, y += 6, CURSOR_HLUM);
        wr_px_xy (x -= 6, y, CURSOR_LLUM);
        wr_px_xy (x -= 6, y, CURSOR_HLUM);
        wr_px_xy (x, y -= 6, CURSOR_LLUM);
        wr_px_xy (x, y -= 6, CURSOR_HLUM);
}
```

- Table 2 p.162 -

```
cursor_value(cursor_data, average)
int *cursor_data, average;
{
        int i, size, value = 0;

i = size = (average) ? CUR_AVE_SIZE : 1;
        while(i--)
                value += *cursor_data++;
        return(value / size);
} region_of_int(cp)
struct curwindow *cp;
{
        int *data;

static struct menwindow menu =
        {
                17, 4, " -  ROI  Menu  -", "F1: Entire Image", "F2: Mark A Block",
                "F3: Previous Menu"
        };
        struct menwindow *wp;

wp = &menu;

while(1)
        {
                switch(get_menu_ptr(wp, TRUE, FALSE))
                {
                case 0:
                        cp->xpos = XIMAGEBIN;
                        cp->ypos = YIMAGEBIN;
                        cp->xpos1 = XIMAGEBIN + BINSIZE - 1;
                        cp->ypos1 = YIMAGEBIN + BINSIZE - 1;
                        rd_cursor(cp->pixdata[0], cp->xpos, cp->ypos);
                        return;
                        break;
                case 1:
                        cp->xpos = (cp->xpos < XCURSORMIN) ? XCURSORMIN : cp->xpos;
                        cp->xpos = (cp->xpos > XCURSORMAX) ? XCURSORMAX : cp->xpos;
                        cp->ypos = (cp->ypos < YCURSORMIN) ? YCURSORMIN : cp->ypos;
                        cp->ypos = (cp->ypos > YCURSORMAX) ? YCURSORMAX : cp->ypos;
                        cp->ave = FALSE;
                        move_cursor(cp, TRUE, LEFT_IMG);
                        cp->xpos1 = cp->xpos;
                        cp->ypos1 = cp->ypos;

- Table 2 p.163- data = cp->pixdata[0];
                        cp->pixdata[0] = cp->pixdata[1];
                        move_cursor(cp, TRUE, LEFT_IMG);
                        cp->pixdata[1] = data;
                        wr_cursor(cp->pixdata[0], cp->xpos, cp->ypos);
                        wr_cursor(cp->pixdata[1], cp->xpos1, cp->ypos1);
                        return;
                        break;
                case 2:
                        return;
                        break;
                }
        }
}
memmodel.mac

;**
:
```

; This macro library generates the appropriate GROUP, SEGMENT,
  and ASSUME statements for the memory model being used.
;
;**
MSDOS   EQU   2
;**
;
; The following symbols define the 8086 memory mode being used.  Set
  LPROG
; to 1 for a large program segment (greater than 64K-bytes), and set
  LDATA
; to 1 for a large data segment.
;
;**
LPROG   EQU   0
LDATA   EQU   0
;**
;
; The following symbols are established via LPROG and LDATA as follows:
;
;       S8086   set for small model (small prog, small data)
;       D8086   set for model with large data, small prog
;       P8086   set for model with large prog, small data
;       L8086   set for large model
;
;**
        IF    (LPROG EQ 0) AND (LDATA EQ 0)
S8086   EQU   1
D8086   EQU   0
P8086   EQU   0
L8086   EQU   0
        ENDIF

- Table 2 p.164-

IF    (LPROG EQ 0) AND (LDATA NE 0)
S8086   EQU   0
D8086   EQU   1
P8086   EQU   0
L8086   EQU   0
        ENDIF

IF    (LPROG NE 0) AND (LDATA EQ 0)
S8086   EQU   0
D8086   EQU   0
P8086   EQU   1
L8086   EQU   0
        ENDIF

IF    (LPROG NE 0) AND (LDATA NE 0)
S8086   EQU   0
D8086   EQU   0
P8086   EQU   0
L8086   EQU   1
        ENDIF

;**
;
; The DSEG and PSEG macros are defined to generate the appropriate
  GROUP,
; SEGMENT, and ASSUME statements for the memory model being used.  The
  ENDDS
; and ENDPS macros are then used to end the segments.
;
;**
DSEG    MACRO
_DATA   SEGMENT WORD PUBLIC 'DATA'
        ASSUME DS:DGROUP, SS:DGROUP, ES:DGROUP
        ENDM
ENDDS   MACRO
_DATA   ENDS
        ENDM

```
         IF     S8086
_TEXT   SEGMENT WORD PUBLIC 'CODE'
_TEXT   ENDS
_DATA   SEGMENT WORD PUBLIC 'DATA'
_DATA   ENDS
CONST   SEGMENT WORD PUBLIC 'CONST'
CONST   ENDS
_BSS    SEGMENT WORD PUBLIC 'BSS'
_BSS    ENDS
DGROUP  GROUP   CONST, _BSS, _DATA
PSEG    MACRO
_TEXT   SEGMENT WORD PUBLIC 'CODE'
        ASSUME  CS:_TEXT, DS:DGROUP, SS:"DGROUP, ES:DGROUP
```

— Table 2 p.165—

```
        ENDM
ENDPS   MACRO
_TEXT   ENDS
        ENDM
        ENDIF

IF     D8086
PSEG    MACRO
_DATA   SEGMENT WORD PUBLIC 'DATA'
_DATA   ENDS
CONST   SEGMENT WORD PUBLIC 'CONST'
CONST   ENDS
_BSS    SEGMENT WORD PUBLIC 'BSS'
_BSS    ENDS
DGROUP  GROUP   CONST, _BSS, _DATA
_TEXT   SEGMENT BYTE PUBLIC 'CODE'
        ASSUME  CS:_TEXT, DS:DGROUP, SS:DGROUP, ES:DGROUP
        ENDM
ENDPS   MACRO
_TEXT   ENDS
        ENDM
        ENDIF

IF     P8086
PSEG    MACRO
_CODE   SEGMENT BYTE
        ASSUME  CS:_CODE
        ENDM
ENDPS   MACRO
_CODE   ENDS
        ENDM
        ENDIF

IF     L8086
PSEG    MACRO
_PROG   SEGMENT BYTE
        ASSUME  CS:_PROG
        ENDM
ENDPS   MACRO
_PROG   ENDS
        ENDM
        ENDIF
```

— Table 2 p.166—

What is claimed is:

1. An X-ray table assembly for supporting a female patient in a prone position for mammography procedures, comprising:

a base having a front portion and a rear portion, a rear pedestal upstanding from the rear protion of said base, a substantially flat and horizontal patient-supporting platform which is supported cantilever-fashion from a rear longitudinal edge by said rear pedestal, having a free unsupported front edge, a right end, a left end, and a concavely-dished shallow torso-receiving recess extending across its central portion from said pedestal to said front edge, means centrally positioned in said platform recess, mid-way between said right end and said left end, forming an open breast-receiving aperture for pendulant presentation of the patient's breast therethrough below the level of the platform, wherther the patient's head is positioned to the right or to the left of said aperture, means forming right and left underside recesses in said platform flanking said breast-receiving aperture and said torso-receiving recess, a C-arm pivotally mounted on the pedestal beneath the platform for angular movement about a vertical pivot axis aligned with said aperture and having a near end supporting an image receptor, and a remote end supporting an X-ray tubehead forming an X-ray source, said C-arm being dimensioned for pivotal movement through a arc of more than 180° around the breast-receiving aperture, positioning the X-ray source in any of an infinite number of source positions ranging from the direction of one end of said platform through a lateral position remote from said rear pedestal to the direction of the other end of said platform, with the tubehead having an upper end positionable in either of said underside recesses above the level of said breast-receiving aperture, thereby facilitating X-ray source positioning around more than a 360° range of positions, with the patient's head positioned toward either the right end or the left end of the platform, a fixed compression plate independent of said C-arm, positioned under said platform near said vertical pivot axis for abutting contact with the patient's presented breast, a movable compression paddle positioned under said platform near said first compression plate for gentle clamping of said presented breast between said compression plate and said paddle independent of said pivotally mounted C-arm, and X-ray responsive image-forming means mounted on said image receptor.

2. An X-ray table assembly for supporting a female patient in a prone position for mammography procedures, comprising:

a base having a front portion and a rear portion, a rear pedestal upstanding from said rear portion of the base, a substantially flat, horizontal, elongated patient-supporting platform which is centrally supported cantilever-fashion from a rear longitudinal edge by said rear pedestal and having a free unsupported front edge, and unsupported right and left lateral ends, means centrally positioned in said platform between said ends, forming an open breast-receiving aperture for pendulant presentation of the patient's breast therethrough below the level of the platform, a C-arm having a remote end supporting an X-ray tubehead forming an X-ray source, and a near end supporting an image receptor, pivotally mounted on the rear pedestal beneath the platform for angular movement through an angular range of more than 180° about a vertical pivot axis aligned with said aperture, positioning the X-ray source in any of an infinite number of source positions ranging from the direction of one end of said platform through a lateral position remote from said rear pedestal to the direction of the other end of said platform, thereby facilitating X-ray source positioning around more than a 360° range of positions, with the patient's head positioned toward either the right end or the left end of the platform, a fixed compression plate independent of said C-arm, positioned under said platform near said vertical pivot axis for abutting contact with the patient's presented breast, a movable compression paddle independent of said C-arm, positioned under said platform near said first compression plate for clamping of said presented breast between said compression plate and said paddle independent of said pivotally mounted C-arm, and X-ray responsive image-forming means mounted on said image receptor, whereby free access is provided for attending personnel to the upper, the lateral and the lower surfaces of the patient's pendulant breast over a range of more than 180°, unimpeded by the rear supporting pedestal.

3. The X-ray table assembly defined in claim 2, wherein said elongated platform is provided with two extensible and retractable footrests, each movably positioned respectively at one lateral end of said platform, the elongated platform being dimensioned to support an adult prone female patient with her legs supported by one said footrest, and alternatively to support the patient lying in the opposite direction with her legs supported by the other said footrest.

4. The X-ray table assembly defined in claim 2 wherein the rear pedestal is vertically extensible and retractable, providing vertically adjustable level positioning for the platform.

5. The X-ray table assembly defined in claim 1, wherein the pivotal mounting of the C-arm on the rear pedestal incorporates vertical adjustment means for raising and lowering the C-arm in the direction of said vertical pivot axis between lower positions, and an uppermost position in which the tubehead's upper end extends into either of said shallow underside recesses above the level of said breast-receiving aperture.

6. The X-ray table assembly defined in claim 2, wherein the pivotal mounting of the C-arm on the rear pedestal provides angular pivoting movement of the C-arm about the vertical pivot axis through an arc of approximately 210° from a first position on the rear pedestal side of the longitudinal centerline of the platform adjacent a first lateral end of the platform, forwardly beneath the front edge of the platform through a second front position remote from the pedestal to a third position on the rear pedestal side of the longitudinal centerline of the platform adjacent the second lateral end of the platform opposite to said first end, and wherein said elongated platform accommodates a patient lying prone thereon with her feet at either end, whereby X-ray examination from any X-ray tubehead source position within said approximately 210° arc can be conducted from either side of the patient as required.

7. The X-ray table assembly defined in claim 2, wherein the pivotal mounting of the C-arm on the pedestal provides angular pivoting movement of the C-arm about the vertical pivot axis between a pair of source positions angularly offset from a central stereo axis by equal acute angles, providing X-ray images of the patient's target breast tissue, held stationary between the clamping compression plate and paddle, produced by X-rays from each of the pair of source positions, with the X-ray beam from each source position being perpendicular to the image forming means mounted in said image receptor on said C-arm by reason of the anchored support of said image receptor opposite said X-ray tubehead on the same supporting C-arm.

8. The X-ray table assembly defined in claim 7, wherein the clamping compression plate and paddle remain fixed while the X-ray tubehead and the image receptor both permanently supported on the C-arm, move angularly together in the same angular direction about the vertical pivot axis as the tubehead moves on the C-arm between the two source positions.

9. The X-ray table assembly defined in claim 8, wherein the clamping compression plate and paddle are mounted on a compression arm mounted on the rear pedestal for pivotal movement about the same pivot axis independent of the C-arm, and wherein a needle guide is also mounted on the same compression arm, positioned for performing needle biopsies on breast tissue clamped between plate and paddle.

10. The X-ray table assembly defined in claim 2, further including X-ray responsive image-forming means mounted on said image receptor, including a charge coupled device (CCD) camera for converting visible light into an electronic signal, a phosphor plate producing a visible light image on its proximal surface in response to arriving X-radiation impinging thereon, light-directing means positioned to direct said phosphor plate's visible light image on said proximal surface toward the CCD camera, computing means connected to the CCD camera for receipt of its electronic signal and for producing an imaging signal representative of at least a portion of the received CCD camera electronic signal, and means connected to the computer imaging signal, for displaying the imaging signal.

11. The X-ray table assembly defined in claim 10, wherein the light-directing means is a diagonally positioned pellicle mirror substantially transparent to X-rays interposed in the path of said arriving X-radiation, with its undersurface coated with a visible light-reflecting film and positioned to reflect said phosphor plate's proximal surface visible light image toward the CCD camera, and wherein the phosphor plate, the pellicle mirror and the CCD camera are all enclosed in a compact light-tight optical system housing positioned closely adjacent to said clamping plates, whereby passage of the visible light, produced on the proximal surface of the phosphor plate, through the thickness of the phosphor plate and consequent diffusion or blurring of the visible light image are avoided.

12. The X-ray table assembly defined in claim 11 wherein said light-tight housing is provided with an X-ray transparent portion interposed in the path of said arriving X-radiation, thus allowing it to pass through said X-ray transparent pellicle mirror toward said phosphor plate.

13. The X-ray table assembly defined in claim 11, further including a second mirror positioned to reflect the visible light on the proximal surface of said phosphor plate from said pellicle mirror toward said CCD camera, whereby the optical system is folded along a bent optic axis for enhanced compactness.

14. An X-ray table assembly as defined in claim 11, wherein the computing means for producing an imaging signal representative of at least a portion of the received CCD camera electronic image includes means for generating a proportional remapping of at least a portin of the CCD camera electronic signal, and further includes means for modifying at least aportion of the imaging signal.

15. An X-ray table as defined in claim 14, wherein the modifying means includes means for varying the contrast associated with the imaging signal.

16. An X-ray table as defined in claim 15, wherein the means for varying the contrast includes means for selecting a range of luminance values of the electronic signal for which the modifying means generates a proportional remapping of at least a portion of the CCD camera electronic signal.

17. An X-ray table as defined in claim 16, wherein the modifying means includes means for sliding the range of luminance values with respect to all possible values of the CCD camera electronic signal.

18. An X-ray table as defined in claim 17, wherein the modifying means further includes means for automatically determining the range of luminance values from the CCD electronic signal for which the imaging signal proportionately remaps the CCD electronic signal.

19. An X-ray table as defined in claim 14, wherein the modifying means include means for modifying the imaging signal formed upon a neighborhood of CCD camera electronic signal values corresponding to the imaging signal.

20. An X-ray table assembly for supporting a female patient in a prone position for mammography procedures, comprising:
  a base,
  a pedestal upstanding from said base,
  a substantially flat and horizontal patient-supporting platform which is supported cantilever-fashion from a rear longitudinal edge by said pedestal and having a free unsupported front edge,
  means centrally positioned in said platform forming an open breast-receiving aperture for pendulant presentation of the patient's breast therethrough below the level of the platform,
  a C-arm pivotally mounted on the pedestal beneath the platform for angular movement about a vertical pivot axis aligned with said aperture and having a remote end supporting an X-ray tubehead forming an X-ray source, and a near end supporting an image receptor,
  a fixed compression plate positioned under said platform near said vertical pivot axis for abutting contact with the patient's presented breast, a movable compression paddle positioned under said platform near said first compression plate for clamping of said presented breast between said compression plates independent of said pivotally mounted C-arm, and X-ray responsive image-forming means mounted on said image receptor, including a charge coupled device (CCD) camera for converting visible light into an electronic signal, a phosphor plate producing on its proximal surface a visible light image in response to arriving X-radiation impinging thereon, light-directing means positioned to direct said phosphor plate's proximal surface visible light image toward the CCD camera, computing means connected to the CCD camera for receipt of its electronic signal and for producing an imaging signal representative of at least a portion of the received CCD camera electronic signal, and means connected to the computer imaging signal, for displaying the imaging signal, wherein the light-directing means is a diagonally positioned X-ray transparent pellicle mirror interposed in the path of said arriving X-radiation, with its undersurface positioned to reflect said phosphor plate's image toward the CCD camera, and wherein the phosphor plate, the pellicle mirror and the CCD camera are all enclosed in a compact light-tight optical system housing positioned closely adjacent to said clamping plates.

21. The X-ray table assembly defined in claim 20, wherein the light-directing means is a diagonally positioned pellicle mirror interposed in the path of said arriving X-radiation, with its undersurface positioned to reflect said phosphor plate's image toward the CCD camera, and wherein the phosphor plate, the pellicle mirror and the CCD camera are all enclosed in a compact light-tight optical system housing positioned closely adjacent to said clamping plates.

22. The X-ray table assembly defined in claim 21 wherein said light-tight housing is provided with an X-ray transparent portion interposed in the path of said arriving X-radiation, thus allowing it to pass through said X-ray transparent pellicle mirror toward said phosphor plate.

23. The X-ray table assembly defined in claim 21, further including a second mirror positoned to reflect the image of said phosphor plate from said pellicle mirror toward said CCD camera, whereby the optical system is folded along a bent optic axis for enhanced compactness.

24. An X-ray table assembly as defined in claim 21, wherein the computing means for producing an imaging signal representative of at least a portion of the received CCD camera electronic image includes means for generating a proportional remapping of at least aportion of the CCD camera electronic signal, and further includes means for modifying at least a portion of the imaging signal.

25. An X-ray table as defined in claim 24, wherein the modifying menas includes means for varying the contrast associated with the imaging signal.

26. An X-ray table as defined in claim 25, wherein the means for varying the contrast includes means for selecting a range of luminance values of the electronic signal for which the modifying means generates a proportional remapping of at least a portion of the CCD camera electronic signal.

27. An X-ray table as defined in claim 26, wherein the modifying means includes means for sliding the range of luminance values with respect to all possible values of the CCD camera electronic signal.

28. An X-ray table as defined in claim 27, wherein the modifying means further includes means for automatically determining the range of luminance values from the CCD electronic signal for which the imaging signal proportionately remaps the CCD electronic signal.

29. An X-ray table as defined in claim 24, wherein the modifying means include means for modifying the imaging signal formed upon a neighborhood of CCD camera electronic signal values corresponding to the imaging signal.

30. A compact CCD imaging assembly for converting arriving X-radiation to a digital image signal output, comprising:
a hollow camera housing positioned in the path of the arriving X-radiation and having an X-ray transparent wall member presented to receive and transmit the arriving X-radiation to the interior of the housing,
a phosphor plate positioned inside the housing in the path of the arriving X-radiation, producing on its proximal surface a visible light image corresponding to the intensity variations exhibited by the arriving X-radiation,
a thin pellicle film diagonally positioned between the transparent wall member and the phosphor plate, substantially transparent to X-radiation and having its underside bearing a light reflective coating,
and a CCD camera aligned to receive visible light produced by said phosphor plate and reflected by said reflective coating.

31. The CCD imaging assembly defined in claim 30, further including a second reflective mirror interposed between said diagonal pellicle film and said CCD camera, whereby the optic axis extending from said phosphor plate via said pellicle film to said CCD camera can be folded for compact positioning inside said housing.

32. An X-ray table assembly for supporting a female patient in a prone position for mammography procedures, comprising:
a base having a front portion and a rear portion,
a rear pedestal upstanding from said rear portion of the base,
a substantially flat, horizontal, elongated patient-supporting platform which is centrally supported cantilever-fashion from a rear longitudinal edge by said rear pedestal and having a free unsupported front edge, and unsupported right and left lateral ends,
means centrally positioned in said platform between said ends, forming an open breast-receiving aperture for pendulant presentation of the patient's breast therethrough below the level of the platform,
a C-arm having a remote end supporting an X-ray tubehead forming an X-ray source, and a near end supporting an image receptor, pivotally mounted on the rear pedestal beneath the platform for angular movement through an angular range of more than 180° about a vertical pivot axis aligned with said aperture, positioning the X-ray source in any of an infinite number of source positions ranging from the direction of one end of said platform through a lateral position remote from said rear pedestal to the direction of the other end of said platform, thereby facilitating X-ray source positioning around more than a 360° range of positions, with the patient's head positioned toward either the right end or the left end of the platform, a fixed compression plate independent of said C-arm, positioned under said platform near said vertical pivot axis for abutting contact with the patient's presented breast, a movable compression paddle independent of said C-arm, positioned under said platform near said first compression plate for clamping of said presented breast between said compression plate and said paddle independent of said pivotally mounted C-arm, and X-ray responsive image-forming means mounted on said image receptor, with the central part of the free unsupported front edge of the patient-supporting platform being formed as a detachable segment, removable from the platform to provide a cutaway bight near said aperture accommodating the patient's arm in a relaxed position, whereby the patient's presented breast is freely pendulant in an undistorted position beneath the platform, whereby free access is provided for attending personnel to the upper, the lateral and the lower surfaces of the patient's pendulant breast over a range of more than 180°, unimpeded by the rear supporting pedestal.

* * * * *